(12) United States Patent
Fujino et al.

(10) Patent No.: US 8,212,112 B2
(45) Date of Patent: Jul. 3, 2012

(54) GENE PARTICIPATING IN LOW TEMPERATURE GERMINABILITY IN RICE AND UTILIZATION OF THE SAME

(75) Inventors: Kenji Fujino, Hokkaido (JP); Hiroshi Sekiguchi, Hokkaido (JP)

(73) Assignee: Hokuren Federation of Agricultural Cooperatives, Hokkaido (JP)

(*) Notice: Subject to any disclaimer, the term of this patent is extended or adjusted under 35 U.S.C. 154(b) by 0 days.

(21) Appl. No.: 12/676,473

(22) PCT Filed: Sep. 5, 2008

(86) PCT No.: PCT/JP2008/066110
§ 371 (c)(1),
(2), (4) Date: Jul. 6, 2010

(87) PCT Pub. No.: WO2009/031664
PCT Pub. Date: Mar. 12, 2009

(65) Prior Publication Data
US 2011/0119790 A1    May 19, 2011

(30) Foreign Application Priority Data
Sep. 7, 2007 (JP) ................................. 2007-233461

(51) Int. Cl.
*A01H 5/00* (2006.01)
*A01H 5/10* (2006.01)
*C12N 15/29* (2006.01)
*C12N 15/63* (2006.01)

(52) U.S. Cl. ................ 800/289; 800/298; 800/320.2; 435/468; 536/23.1

(58) Field of Classification Search ........................ None
See application file for complete search history.

(56) References Cited

U.S. PATENT DOCUMENTS
2007/0044171 A1* 2/2007 Kovalic et al. .............. 800/278

FOREIGN PATENT DOCUMENTS
JP          2003-180362          7/2003

OTHER PUBLICATIONS

Fujino et al (PNAS, Aug. 26, 2008, vol. 15 No. 34 12623-12628).*
Gao et al (PNAS 2004 (101)25,9205-9210.*
International Search Report for WO/2009/031664 mailed Oct. 14, 2008.
Ohyanagi H. et al., Locus NM_001055203, Definition *Oryza sativa* (japonica cultivar group) Os03g0103300 (Os03g0103300) mRNA, complete cds., NCBI accession NM_001055203, GI: 115450134, Oct. 3, 2006 updated [online], http://www.ncbi.nlm.nih.gov/entrez/sutils/girevhist.cgi?val=NM_001055203.
Kenji Fujino et al., "Ine Teion Hatsugasei QTL no Koseido Mapping", Breeding research, 2006, vol. 8, separate vol. 1, 153.
Fujino K et al., Mapping of quantitative trait loci controlling low-temperature germinability in rice (*Oryza sativa* L.)., Theor. Appl. Genet., 2004, vol. 108, p. 794-799.
Kenji Fujino, Hiroshi Sekiguchi, "Stress-ka ni Okeru Ine Shushi Hatsugasei no QTL Kaiseki", Breeding research, Mar. 2007, vol. 9, separate vol. 1, p. 117.
International Rice Genome Sequencing Project, The map-based sequence of the rice genome., Nature, 2005, vol. 436, p . 793-800.
Ohyanagi H et al., The rice annotation project database (RAP-DB): hub for *Oryza sativa* spp. japonica genome information., Nucl. Acids Res., 2006, vol. 34, p. D741-D744.
Fujino K et al., Molecular identification of a major quantitative trait locus, qLTG3-1, controlling low-temperature germinability in rice., Proc. Natl. Acad. Sci. USA, Aug. 26, 2008, vol. 105, No. 34, p. 12623-12628.
Fujino K et al., Locus AB369214, Definition *Oryza sativa* Japonica Group qLTG3-1 gene, complete cds, cultivar: Italica Livorno., NCBI accession AB369214, GI: 193788020, Jul. 2, 2008 uploaded [online], http://www.ncbi.nlm.nih.gov/entrez/sutils/girevhist. cgi?val=AB369214.
Kenji Fujino et al., "Ine Teion Hatsugasei Idenshi qLTG-3-1 no Tanris", Breeding research, Sep. 22, 2007, vol. 9, separate vol. 2, p. 46.
Hiroshi Sekiguchi et al., "Italia Yurai Ine Keito 'Italica Livorno' o Mochiita Ine Teion Hatsugasei Idenshi no Tanri", Japan Society of Breeding • Crop Science Society of Japan Hokkaido Danwakai Kaiho, Dec. 2007, vol. 48, pp. 107 to 108.
Kenji Fujino et al., "Positional Cloning ni yoru Ine no Teion Hatsugasei ni Kakawaru Idenshi no tanri", Dai 49 Kai Proceedings of the Annual Meeting of the Japanese Society of Plant Physiologists, Mar. 15, 2008, p. 166 (2aE02(256)).
Ikushugaku Kenkyu 5 (Suppl. 2), p. 212 (2003).
Ikushugaku Kenkyu 8 (Suppl. 1), p. 153 (2006).
Ikushugaku Kenkyu 9 (Suppl. 1), p. 117 (2007).

* cited by examiner

*Primary Examiner* — Anne Kubelik
*Assistant Examiner* — Lee A Visone
(74) *Attorney, Agent, or Firm* — Suzannah K. Sundby; Smith, Gambrell & Russell, LLP

(57) ABSTRACT

The present invention provides a gene participating in the low temperature germinability in rice and utilization of the same, and the invention relates to a gene for a low temperature germinability which is an isolated qLTG-3-1 gene from the rice line Italica Livorno, has low temperature germinability and has the base sequence of SEQ ID NO: 1; an amino acid sequence encoded by the gene; a transgenic plant transformed with the gene for the low temperature germinability to improve the low temperature germinability; a method of analyzing low temperature germinability, including analyzing the low temperature germinability of a cultivar by comparing the base sequence of the gene for the low temperature germinability with the genotype of the cultivar; a method of improving the low temperature germinability of rice, including transforming the gene for the low temperature germinability into a rice cultivar to improve the low temperature germinability of the cultivar under low temperature conditions; and a method of analyzing the low temperature germinability of a rice cultivar by utilizing the expression of the gene for the low temperature germinability.

11 Claims, 38 Drawing Sheets

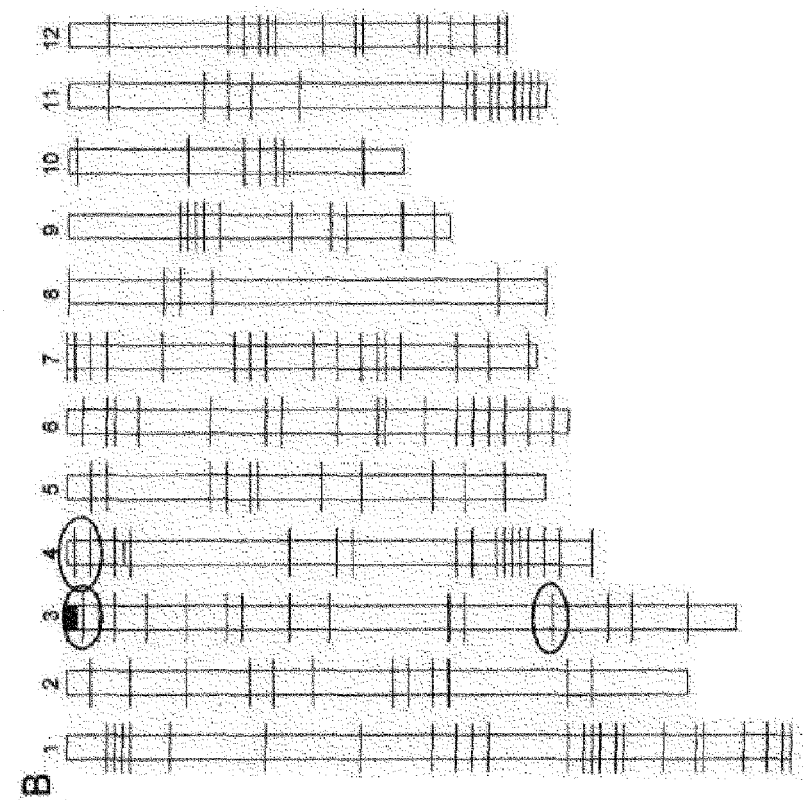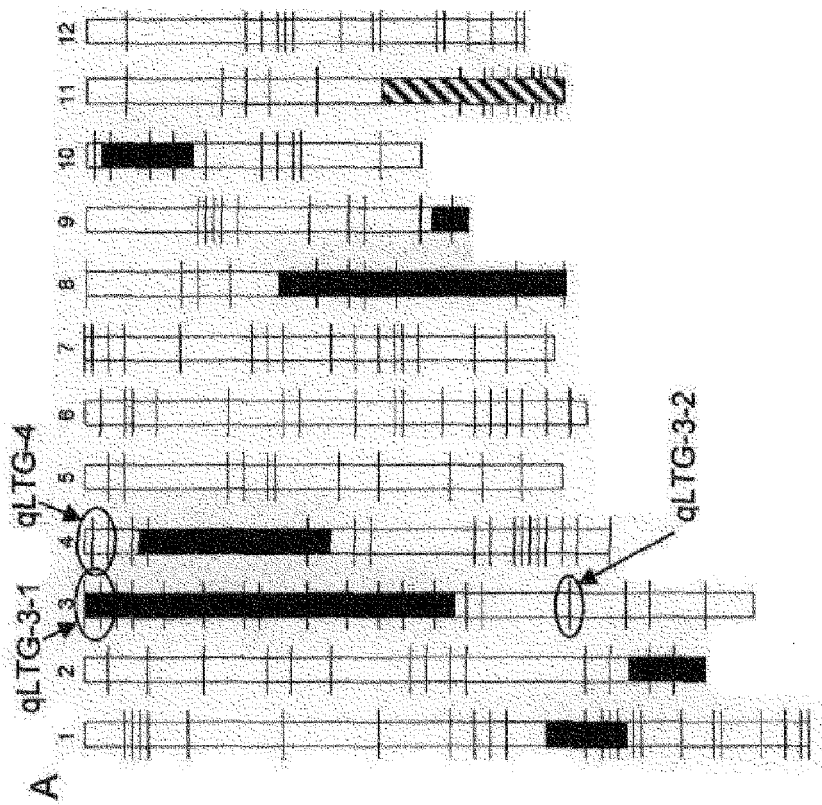
Fig. 1

Nipponbare: H

1   MATKAGVIAT LIALNLLFFT FSDACGCQCG SCPSPGGGGG GGGGGGGGGG   50
51  GRGGGGGSGG GSGGGGGSGG GGSGGGGSGG GGSGGGGGGG SGGGGGGGRC   100
101 PIDTLKLGVC ANVLNGLINV QLGTPPRQPC CSLIQGLADL EAAVCLCTAL   150
151 RANILGINLN LPINLSLLVN YCGRSVPSGF QCSN

```
Italica Livorno    1  MATKAGVIATLLALNLLFFTFSDACGCQCGSCPSPGGGGGGGGGGGGGGGGGGSGGGGSGG    80
Hayamasari         1  MATKAGVIATLLALNRWRWRWRWRAWRWWRERRRFRWRRKRRRRRKRRRRGRRKMPDRH    80
Nipponbare         1  MATKAGVIATLLALNLHFFTFSDACGCQCGSCPSPGGGGGGGGGGRGGGGSGGGGSGGGGSGG    80

Italica Livorno   81  GGSGGGGGGSGGGGGGGGRCPIDTLKLGVCANVLNGLINVQLGTPPRQPCCSLIQGLADLEAAVCLCTALRANILGINLN  160
Hayamasari        81  AEAGGVRERAEWADKRAAGDAAAAAVLQPHPGPRRP*                                            117
Nipponbare        81  GGSGGGGGGSGGGGGGGGRCPIDTLKLGVCANVLNGLINVQLGTPPRQPCCSLIQGLADLEAAVCLCTALRANILGINLN  160

Italica Livorno  161  LPINLSLLVNYCGRSVPSGFQCSN*  185
Nipponbare       161  LPINLSLLVNYCGRSVPSGFQCSN*  185
```

```
CA103536So   1 ----------VSLFLLLDLLLFAAANAC-------
CA183659So   1 -MAKKVAVVATLLALNLLLFGFADAC---------
CA411379La   1 MASKVSSSLALFLTLNLLFFTLVSSCGTCDQP
CA592494Hv   1 -MARKAAVIATLLALNLLFFTVADSC---------
CB882819Hv   1 -MAKKAAVIATLLALNLLFFTFADAC---------
CD038041Ah   1 ----------IALFLIVNILFFSLVSACGTCPGP
CD912168Ta   1 -MAKKAAVIATLLALNLLFFTFADAC---------
CJ711399Ta   1 -MATKAAVIATLLALNLLFFTLADDC---------
CK209890Ta   1 -MAKKVQVIATLLALNLLFFTFANAT---------
CV435103St   1 ---TEASLVTLFLSFNLLFFAIVTAT---------
CV540220Pv   1 ----------LALFLTLNILFFALVSSCGTCPGN
DN910955Cs   1 ----------IALFFCLNLLFFSLVTACGSCSHP
DV469548Bd   1 -MAKKAAAIATLLALNLLFFTFSDAC---------
DV474442Bd   1 -MAKKVELIVALLALNLLFFTFSDAS---------
DV488964Bd   1 ----------LALNLLLFSVTSAC-----------
DY618062Mt   1 MASKTCSSLAIFLTINILFFTLVSSCGTCGSG
EC878574Zm   1 ---------VPLFLVLNLLLFAAANAC--------
EE030610Zm   1 --STMAKKVATLLALNLLFFAFADAC---------
AJ937849Nt   1 --MASKTRASVALFLSLNLLFLVIVS---------
BP895081Le   1 ---TKASLLILFLSLNLLFFAIVTAT---------
BQ452738Gm   1 ---------------INILFFALASACGTCPSP
qLTG_3_1     1 -MATKAGVIATLLALNLLFFTFSDAC---------
consensus    1                    ..   ...........  ..
```

AxxLALNLLFFxxxxxAC

Fig. 9

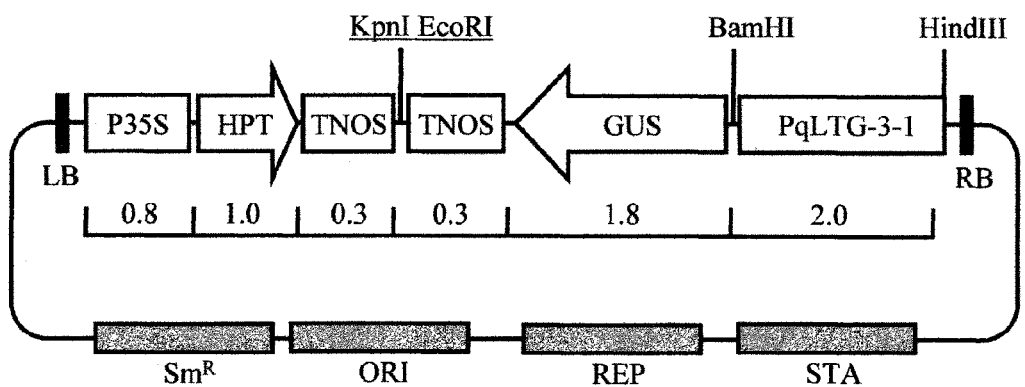

promoter 2kb+GUS

P35S; Cauliflower mosaic virus 35S promoter
HPT; Hygromycin phosphotransferase gene
TNOS; Terminator from the *NOS* gene
PqLTG-3-1; Promoter region of qLTG-3-1
GUS; β-glucronidase gene
$Sm^R$; Bacterial streptomycin resistance gene
ORI; ColE1 replication origin from plasmid pBR322
REP; Replication region of plasmid pVS1
STA; Stability region of plasmid pVS1
LB; Left T-DNA border
RB; Right T-DNA border

Fig. 20

```
                  ************************************************ ******************** *******
qLTG-3-1    1  ATGGCGACGAAAGCTGGGGTGATCGCCACGCTCCTGGCCCTGAACCTCCTCTTCTTCACCTTCTCCGACGCGTGCGGCTG  80
Haplotype1  1  ATGGCGACGAAAGCTGGGGTGATCGCCACGCTCCTGGCCCTGAACCTCCTCTTCTTCACCTTCTCCGACGCGTGCGGCTG  80
Haplotype2  1  ATGGCGACGAAAGCTGGGGTGATCGCCACGCTCCTGGCCCTGAACCTCCTCTTCTTCACCTTCTCCGACGCGTGCGGCTG  80
Haplotype3  1  ATGGCGACGAAAGCTGGGGTGATCGCCACGCTCCTGGCCCTGAACCTCCTCTTCTTCACCTTCTCCGACGCGTGCGGCTG  80
Haplotype4  1  ATGGCGACGAAAGCTGGGGTGATCGCCACGCTCCTGGCCCTGAACCTCCTCTTCTTCACCTTCTCCGACGCGTGCGGCTG  80
Haplotype5  1  ATGGCGACGAAAGCTGGGGTGATCGCCACGCTCCTGGCCCTGAACCTCCACTTCTTCACCTTCTCCGACGCGTGCGGCTG  80
Haplotype6  1  ATGGCGACGAAAGCTGGGGTGATCGCCACGCTCCTGGCCCTGAACCTCCTCTTCTTCACCTTCTCCGACGCGTGCGGCTG  80
Haplotype7  1  ATGGCGACGAAAGCTGGGGTGATCGCCACGCTCCTGGCCCTGAACCTCCTCTTCTTCACCTTCTCCGACGCGTGCGGCTG  80
Haplotype8  1  ATGGCGACGAAAGCTGGGGTGATCGCCACGCTCCTGGCCCTGAACCTCCTCTTCTTCACCTTCTCCGACGCGTGCGGCTG  80
Haplotype9  1  ATGGCGACGAAAGCTGGGGTGATCGCCACGCTCCTGGCCCTGAACCTCCTCTTCTTCACCTTCTCCGACGCGTGCGGCTG  80
Haplotype10 1  ATGGCGACGAAAGCTGGGGTGATCGCCACGCTCCTGGCCCTGAACCTCCTCTTCTTCACCTTCTCCGACGCGTGCGGCTG  80
W0106       1  ATGGCGACGAAAGCTGGGGTGATCGCCACGCTCCTGGCCCTGAACCTCCTCTTCTTCACCTTCTCCGACGCGTGCGGCTG  80
W0652       1  ATGGCGACGAAAGCTGGGGTGATCGCCACGCTCCTGGCCCTGAACCTCCTCTTCTTCACCTTCTCCGACGCGTGCGGCTG  80
W1169       1  ATGGCGACGAAAGCTGGGGTGATCGCCACGCTCCTGGCCCTGAACCTCCTCTTCTTCACCTTCTCCGACGCGTGCGGCTG  80
W1413       1  ATGGCGACGAAAGCTGGGGTGATCGCCACGCTCCTGGCCCTGAACCTCCTCTTCTTCACCTTCTCCGACGCCTGCGGCTG  80
W1508       1  ATGGCGACGAAAGCTGGGGTGATCGCCACGCTCCTGGCCCTGAACCTCCTCTTCTTCACCTTCTCCGACGCCTGCGGCTG  80
```

Fig. 26

```
                       ************************************    ** ******               *
qLTG-3-1     81  CCAGTGCGGCTCATGCCCTAGTCCCGGCGGAGGAGGC------------GGTGGCGGTGGCGGTGGCGGTGGCGGTGGTG 148
Haplotype1   81  CCAGTGCGGCTCATGCCCTAGTCCCGGCGGAGGAGGC------------GGTGGCGGTGGCGGTGGCGGTGGCGGTGGTG 148
Haplotype2   81  CCAGTGCGGCTCATGCCCTAGTCCCGGCGGAGGAGGC------------GGTGGCGGTGGCGGTGGCGGTGGCGGTGGTG 148
Haplotype3   81  CCAGTGCGGCTCATGCCCTAGTCCCGGCGGAGGAGGC------------GGTGGCGGTGGCGGTGGCGGTGGCGGTGGTG 148
Haplotype4   81  CCAGTGCGGCTCATGCCCTAGTCCCGGCGGAGGAGGC------------GGTGGCGGTGGCGGTGGCGGTGGCGGTGGTG 148
Haplotype5   81  CCAGTGCGGCTCATGCCCTAGTCCCGGCGGAGGAGGC------------GGTGGCGGTGGCGGTGGCGGTGGCGGTGGTG 148
Haplotype6   81  CCAGTGCGGCTCATGCCCTAGTCCCGGCGGAGGAGGC------------GGTGGCGGT--------------------GGTG 130
Haplotype7   81  CCAGTGCGGCTCATGCCCTAGTCCCGGCGGAGGAGGC------------GGTGGCGGT--------------------GGTG 130
Haplotype8   81  CCAGTGCGGCTCATGCCCTAGTCCCGGCGGAGGAGGC------------GGTGGCGGT--------------------GGTG 130
Haplotype9   81  CCAGTGCGGCTCATGCCCTAGTCCCGGCGGAGGAGGC------------GGTGGCGGT--------------------GGTG 130
Haplotype10  81  CCAGTGCGGCTCATGCCCTAGTCCCGGCGGAGGAGGC------------GGTGGCGGT--------------------GGTG 130
W0106        81  CCAGTGCGGCTCATGCCCTAGTCCCGGCGGAGGAGGC------------GGTGGCGGTGGCGGTGGCGGT--------GGTG 142
W0652        81  CCAGTGCGGCTCATGCCCTAGTCCCGGCGGAGGAGGC------------GGTGGCGGTGGCGGTGGCGGT--------GGTG 142
W1169        81  CCAGTGCGGCTCATGCCCTAGTCCCGGCGGAGGAGGC------------GGTGGCGGT--------------------GGTG 130
W1413        81  CCAGTGCGGCTCATGCCCTAGTCCCGGCGGAGGAGGCGGAGGCGGAGGCGGAGGCGGTGGCGGTGGCGGTGGC------G 154
W1508        81  CCAGTGCGGCTCATGCCCTAGTCCCGGCGGAGGAGGC------------GGTGGCGGTGGC----------------G 130
```

Fig. 27

```
               **********  **  *****  ************
qLTG-3-1    149 GAGGGCGTGGAGGTGGTGGCGGGAGCGGCGGAGGTTCAGGT————————————————————————— 189
Haplotype1  149 GAGGGCGTGGAGGTGGTGGCGGGAGCGGCGGAGGTTCAGGT————————————————————————— 189
Haplotype2  149 GAGGGCGTGGAGGTGGTGGCGGGAGCGGCGGAGGTTCAGGT————————————————————————— 189
Haplotype3  149 GAGGGCGTGGAGGTGGTGGCGGGAGCGGCGGAGGTTCAGGT————————————————————————— 189
Haplotype4  149 GAGGGCGTGGAGGTGGTGGCGGGAGCGGCGGAGGTTCAGGT————————————————————————— 189
Haplotype5  149 GAGGGCGTGGAGGTGGTGGCGGGAGCGGCGGAGGTTCAGGT————————————————————————— 189
Haplotype6  131 GAGGGCGTGGAGGTGGTGGCGGGAGCGGCGGA—————————————————————————————————— 162
Haplotype7  131 GAGGGCGTGGAGGTGGTGGCGGGAGCGGCGGA—————————————————————————————————— 162
Haplotype8  131 GAGGGCGTGGAGGTGGTGGCGGGAGCGGCGGA—————————————————————————————————— 162
Haplotype9  131 GAGGGCGTGGAGGTGGTGGCGGGAGCGGCGGAGGTTCAGGTGGGGGTTCAGGTGGTGGAGGAAGCGGAGGCGGAGGT—— 207
Haplotype10 131 GAGGGCGTGGAGGTGGTGGCGGGAGCGGCGGA—————————————————————————————————— 162
W0106       143 GAGGGCGTGGAGGTGGTGGCGGGAGCGGCGGAGGTTCAGGTGGGGGTTCAGGTGGTGGAGGAAGCGGAGGCGGAGGT—— 219
W0652       143 GAGGGCGTGGAGGTGGTGGCGGGAGCGGCGGAGGTTCAGGTGGGGGTTCAGGTGGTGGAGGAAGCGGAGGCGGAGGTCA 222
W1169       131 GAGGGCGTGGAGGAGGTGGCGGGAGCGGCGGAGGTTCAGGTGGGGGTTCAGGTGGTGGACGAAGCGGAGGCGGAGGTCA 210
W1413       155 GAGGGCGTGGAGGTGGTGGCGGGAGCGGCGGAGGTTCAGGTGGGGGTTCTGGCGGTGGTGGA————————————————— 216
W1508       131 GAGGGCGTGGGGGTGGTGGTGGGAGCGGCGGAGGTTCAGGT————————————————————————— 171
```

Fig. 28

```
qLTG-3-1    189 ————————————————GGA————————GGCGGC————GGTTCAGGTGGAGGA————————————GGAAGCGGCGGCGGAGG 230
Haplotype1  189 ————————————————GGA————————GGCGGC————GGTTCAGGTGGAGGA————————————GGAAGCGGCGGCGGAGG 230
Haplotype2  189 ————————————————GGA————————GGCGGC————GGTTCAGGTGGAGGA————————————GGAAGCGGCGGCGGAGG 230
Haplotype3  189 ————————————————GGA————————GGCGGC————GGTTCAGGTGGAGGA————————————GGAAGCGGCGGCGGAGG 230
Haplotype4  189 ————————————————GGA————————GGCGGC————GGTTCAGGTGGAGGA————————————GGAAGCGGCGGCGGAGG 230
Haplotype5  189 ————————————————GGA————————GGCGGC————GGTTCAGGTGGAGGA————————————GGAAGCGGCGGCGGAGG 230
Haplotype6  162 ————————GGCGGAGGTGGA————————GGCGGC————GGTTCAGGTGGAGGA————————————GGAAGCGGCGGCGGAGG 212
Haplotype7  162 ————————GGCGGAGGTGGA————————GGCGGC————GGTTCAGGTGGAGGA————————————GGAAGCGGCGGCGGAGG 212
Haplotype8  162 ————————GGCGGAGGTGGA————————GGCGGC————GGTTCAGGTGGAGGA————————————GGAAGCGGCGGCGGAGG 212
Haplotype9  207 ————————————————GGA————————GGCGGC————GGTTCAGGTGGAGGA————————————GGAAGCGGCGGCGGAGG 248
Haplotype10 162 ————————GGCGGAGGTGGA————————GGCGGC————GGTTCAGGTGGAGGA————————————GGAAGCGGCGGCGGAGG 212
W0106       219 ————————————————GGA————————GGCGGC————GGTTCAGGTGGAGGA————————————GGAAGCGGCGGCGGAGG 260
W0652       223 GGCGGAGGT———————————————GGA————————GGCGGC————GGTTCAGGTGGAGGA————————————GGAAGCGGCGGCGGAGG 272
W1169       211 GGCGGAGGT———————————————GGA————————GGCGGC————GGTTCAGGTGGAGGA————————————GGAAGCGGCGGCGGAGG 260
W1413       216 ————————————————GGA————————AGCGGCGGAGGTTCAGGTGGAGGATCAGGTGGTGGAGGAAGCGGAGGCGGAGG 272
W1508       171 ————————————————GGTGGAGGAAGCGGC————GGAGGTTCAGGTGGAGGATCAGGTGGTGGAGGAAGC————GGCGGAGG 230
```

Fig. 29

```
qLTG-3-1    231 TTCA------------------------------GGCGGTGGAGGAAGCGGAGGC------------G 256
Haplotype1  231 TTCA------------------------------GGCGGTGGAGGAAGCGGAGGC------------G 256
Haplotype2  231 TTCA------------------------------GGCGGTGGAGGAAGCGGAGGC------------G 256
Haplotype3  231 TTCA------------------------------GGCGGTGGAGGAAGCGGAGGC------------G 256
Haplotype4  231 TTCA------------------------------GGCGGTGGAGGAAGCGGAGGC------------G 256
Haplotype5  231 TTCA------------------------------GGCGGTGGAGGAAGCGGAGGC------------G 256
Haplotype6  213 TTCA------------------------------GGCGGTGGAGGAAGCGGAGGC------------G 238
Haplotype7  213 TTCA------------------------------GGCGGTGGAGGAAGCGGAGGC------------G 238
Haplotype8  213 TTCA------------------------------GGCGGTGGAGGAAGCGGAGGC------------G 238
Haplotype9  249 TTCA------------------------------GGCGGTGGAGGAAGCGGAGGC------------G 274
Haplotype10 213 TTCA------------------------------GGCGGTGGAGGAAGCGGAGGC------------G 238
W0106       261 TTCA------------------------------GGCGGTGGAGGAAGCGGAGGC------------G 286
W0652       273 TTCA------------------------------GGCGGTGGAGGAAGCGGAGGC------------G 298
W1169       261 TTCA------------------------------GGCGGTGGAGGAAGCGGAGGC------------G 286
W1413       273 TTCA------------------------------GGCGGT------------------------- 282
W1508       231 TTCAGGTGGAGGATCAGGTGGTGGAGGAAGCGGAGGCGGAGGTTCAGGCGGT----GGAAGCGGAGGCGGTGGAGGAAGCG 307
```

Fig. 30

```
                      *****************       ***        **************************
qLTG-3-1    257 GCGGAGGAGGAGGAAGCGGCGGCGGCGGG----------GGA------------GGAGGAAGATGCCCGATCGACACGCTG 315
Haplotype1  257 GCGGAGGAGGAGGAAGCGGCGGCGGCGGG----------GGA------------GGAGGAAGATGCCCGATCGACACGCTG 315
Haplotype2  257 GCGGAGGAGGAGGAAGCGGCGGCGGCGGG----------GGA------------GGAGGAAGATGCCCGATCGACACGCTG 315
Haplotype3  257 GCGGAGGAGGAGGAAGCGGCGGCGGCGGG----------GGA------------GGAGGAAGATGCCCGATCGACACGCTG 315
Haplotype4  257 GCGGAGGAGGAGGAAGCGGCGGCGGCGGG----------GGA------------GGAGGAAGATGCCCGATCGACACGCTG 315
Haplotype5  257 GCGGAGGAGGAGGAAGCGGCGGCGGCGGG----------GGA------------GGAGGAAGATGCCCGATCGACACGCTG 315
Haplotype6  239 GCGGAGGAGGAGGAAGCGGCGGCGGCGGG----------GGA------------GGAGGAAGATGCCCGATCGACACGCTG 297
Haplotype7  239 GCGGAGGAGGAGGAAGCGGCGGCGGCGGG----------GGA------------GGAGGAAGATGCCCGATCGACACGCTG 297
Haplotype8  239 GCGGAGGAGGAGGAAGCGGCGGCGGCGGG----------GGA------------GGAGGAAGATGCCCGATCGACACGCTG 297
Haplotype9  275 GCGGAGGAGGAGGAAGCGGCGGCGGCGGG----------GGA------------GGAGGAAGATGCCCGATCGACACGCTG 333
Haplotype10 239 GCGGAGGAGGAGGAAGCGGCGGCGGCGGG----------GGA------------GGAGGAAGATGCCCGATCGACACGCTG 297
W0106       287 GCGGAGGAGGAGGAAGCGGCGGCGGCGGG----------GGA------------GGAGGAAGATGCCCGATCGACACGCTG 345
W0652       299 GCGGAGGAGGAGGAAGCGGCGGCGGCGGG----------GGA------------GGAGGAAGATGCCCGATCGACACGCTG 357
W1169       287 GCGGAGGAGGAGGAAGCGGCGGCGGCGGG----------GGA------------GGAGGAAGATGCCCGATCGACACGCTG 345
W1413       282 -----------GGAAGCGGCGGCGGCGGGTCAGGTGGCGGCGGA---------GGCGGAGGAAGATGCCCGATCGACACGCTG 345
W1508       308 GCGGAGGAGGAGGAAGCGGCGGCGGCGGG----------GGAGGAGGAAGCGGAGGAAGATGCCCGATCGACACGCTG 375
```

Fig. 31

```
                    ******************************  ***************************************************** *****
qLTG-3-1     316 AAGCTGGGGGTGTGCGCGAACGTGCTGAATGGGCTGATAAACGTGCAGCTGGGGACGCCGCCGCGGCAGCCGTGTTGCAG 395
Haplotype1   316 AAGCTGGGGGTGTGCGCGAACGTGCTGAATGGGCTGATAAACGTGCAGCTGGGGACGCCGCCGCGGCAGCCGTGTTGCAG 395
Haplotype2   316 AAGCTGGGGGTGTGCGCGAACGTGCTGAATGGGCTGATAAACGTGCAGCTGGGGACGCCGCCGCGGCAGCCGTGTTGCAG 395
Haplotype3   316 AAGCTGGGGGTGTGCGCGAACGTGCTGAATGGGCTGATAAACGTGCAGCTGGGGACGCCGCCGCGGCAGCCGTGTTGCAG 395
Haplotype4   316 AAGCTGGGGGTGTGCGCGAACGTGCTGAATGGGCTGATAAACGTGCAGCTGGGGACGCCGCCGCGGCAGCCGTGTTGCAG 395
Haplotype5   316 AAGCTGGGGGTGTGCGCGAACGTGCTGAATGGGCTGATAAACGTGCAGCTGGGGACGCCGCCGCGGCAGCCGTGTTGCAG 395
Haplotype6   298 AAGCTGGGGGTGTGCGCGAACGTGCTGAATGGGCTGATAAACGTGCAGCTGGGGACGCCGCCGCGGCAGCCGTGTTGCAG 377
Haplotype7   298 AAGCTGGGGGTGTGCGCGAACGTGCTGAATGGGCTGATAAACGTGCAGCTGGGGACGCCGCCGCGGCAGCCGTGTTGCAG 377
Haplotype8   298 AAGCTGGGGGTGTGCGCGAACGTGCTGAATGGGCTGATAAACGTGCAGCTGGGGACGCCGCCGCGGCAGCCGTGTTGCAG 377
Haplotype9   334 AAGCTGGGGGTGTGCGCGAACGTGCTGAATGGGCTGATAAACGTGCAGCTGGGGACGCCGCCGCGGCAGCCGTGTTGCAG 413
Haplotype10  298 AAGCTGGGGGTGTGCGCGAACGTGCTGAATGGGCTGATAAACGTGCAGCTGGGGACGCCGCCGCGGCAGCCGTGTTGCAG 377
W0106        346 AAGCTGGGGGTGTGCGCGAACGTGCTGAATGGGCTGATAAACGTGCAGCTGGGGACGCCGCCGCGGCAGCCGTGTTGCAG 425
W0652        358 AAGCTGGGGGTGTGCGCGAACGTGCTGAATGGGCTGATAAACGTGCAGCTGGGGACGCCGCCGCGGCAGCCGTGTTGCAG 437
W1169        346 AAGCTGGGGGTGTGCGCGAACGTGCTGAATGGGCTGATAAACGTGCAGCTGGGGACGCCGCCGCGGCAGCCGTGTTGCAG 425
W1413        346 AAGCTGGGGGTGTGCGCGAACGTGCTGAACGGGCTGATAAACGTGCAGCTGGGGACGCCGCCGCGGCAGCCGTGCTGCAG 425
W1508        376 AAGCTGGGGGTGTGCGCGAACGTGCTGAATGGGCTGATAAACGTGCAGCTGGGGACGCCGCCGCGGCAGCCGTGCTGCAG 455
```

Fig. 32

```
                ************ **************************************************************
qLTG-3-1    396 CCTCATCCAGGGCCTCGCCGACCTTGAGGCCGCCGTGTGCCTCTGCACCGCCCTCCGCGCCAACATCCTTGGCATCAACC 475
Haplotype1  396 CCTCATCCAGGGCCTCGCCGACCTTGAGGCCGCCGTGTGCCTCTGCACCGCCCTCCGCGCCAACATCCTTGGCATCAACC 475
Haplotype2  396 CCTCATCCAGGGCCTCGCCGACCTTGAGGCCGCCGTGTGCCTCTGCACCGCCCTCCGCGCCAACATCCTTGGCATCAACC 475
Haplotype3  396 CCTCATCCAGGGCCTCGCCGACCTTGAGGCCGCCGTGTGCCTCTGCACCGCCCTCCGCGCCAACATCCTTGGCATCAACC 475
Haplotype4  396 CCTCATCCAGGGCCTCGCCGACCTTGAGGCCGCCGTGTGCCTCTGCACCGCCCTCCGCGCCAACATCCTTGGCATCAACC 475
Haplotype5  396 CCTCATCCAGGGCCTCGCCGACCTTGAGGCCGCCGTGTGCCTCTGCACCGCCCTCCGCGCCAACATCCTTGGCATCAACC 475
Haplotype6  378 CCTCATCCAGGGCCTCGCCGACCTTGAGGCCGCCGTGTGCCTCTGCACCGCCCTCCGCGCCAACATCCTTGGCATCAACC 457
Haplotype7  378 CCTCATCCAGGGCCTCGCCGACCTTGAGGCCGCCGTGTGCCTCTGCACCGCCCTCCGCGCCAACATCCTTGGCATCAACC 457
Haplotype8  378 CCTCATCCAGGGCCTCGCCGACCTTGAGGCCGCCGTGTGCCTCTGCACCGCCCTCCGCGCCAACATCCTTGGCATCAACC 457
Haplotype9  414 CCTCATCCAGGGCCTCGCCGACCTTGAGGCCGCCGTGTGCCTCTGCACCGCCCTCCGCGCCAACATCCTTGGCATCAACC 493
Haplotype10 378 CCTCATCCAGGGCCTCGCCGACCTTGAGGCCGCCGTGTGCCTCTGCACCGCCCTCCGCGCCAACATCCTTGGCATCAACC 457
W0106       426 CCTCATCCAGGGCCTCGCCGACCTTGAGGCCGCCGTGTGCCTCTGCACCGCCCTCCGCGCCAACATCCTTGGCATCAACC 505
W0652       438 CCTCATCCAGGGCCTCGCCGACCTTGAGGCCGCCGTGTGCCTCTGCACCGCCCTCCGCGCCAACATCCTTGGCATCAACC 517
W1169       426 CCTCATCCAGGGCCTCGCCGACCTTGAGGCCGCCGTGTGCCTCTGCACCGCCCTCCGCGCCAACATCCTTGGCATCAACC 505
W1413       426 CCTCATCCAGGGGCTCGCCGACCTTGAGGCCGCCGTGTGCCTCTGCACCGCCCTCCGCGCCAACATCCTTGGCATCAACC 505
W1508       456 CCTCATCCAGGGGCTCGCCGACCTTGAGGCCGCCGTGTGCCTCTGCACCGCCCTCCGCGCCAACATCCTTGGCATCAACC 535
```

Fig. 33

```
              ****************************************************** *****  **********************
qLTG-3-1    476 TCAACCTCCCCATCAACCTCAGCCTCCTCGTCAACTACTGCGGCCGCTCCGTCCCCTCCGGCTTCCAGTGCAGCAACTAA 555
Haplotype1  476 TCAACCTCCCCATCAACCTCAGCCTCCTCGTCAACTACTGCGGCCGCTCCGTCCCCTCCGGCTTCCAGTGCAGCAACTAA 555
Haplotype2  476 TCAACCTCCCCATCAACCTCAGCCTCCTCGTCAACTACTGCGGCCGCTCCGTCCCCTCCGGCTTCCAGTGCAGCAACTAA 555
Haplotype3  476 TCAACCTCCCCATCAACCTCAGCCTCCTCGTCAACTACTGCGGCCGCTCCGTCCCCTCCGGCTTCCAGTGCAGCAACTAA 555
Haplotype4  476 TCAACCTCCCCATCAACCTCAGCCTCCTCGTCAACTACTGCGGCCGCTCCGTCCCCTCCGGCTTCCAGTGCAGCAACTAA 555
Haplotype5  476 TCAACCTCCCCATCAACCTCAGCCTCCTCGTCAACTACTGCGGCCGCTCCGTCCCCTCCGGCTTCCAGTGCAGCAACTAA 555
Haplotype6  458 TCAACCTCCCCATCAACCTCAGCCTCCTCGTCAACTACTGCGGCCGCTCCGTCCCCTCCGGCTTCCAGTGCAGCAACTAA 537
Haplotype7  458 TCAACCTCCCCATCAACCTCAGCCTCCTCGTCAACTACTGCGGCCGCTCCGTCCCCTCCGGCTTCCAGTGCAGCAACTAA 537
Haplotype8  458 TCAACCTCCCCATCAACCTCAGCCTCCTCGTCAACTACTGCGGCCGCTCCGTCCCCTCCGGCTTCCAGTGCAGCAACTAA 537
Haplotype9  494 TCAACCTCCCCATCAACCTCAGCCTCCTCGTCAACTACTGCGGCCGCTCCGTCCCCTCCGGCTTCCAGTGCAGCAACTAA 573
Haplotype10 458 TCAACCTCCCCATCAACCTCAGCCTCCTCGTCAACTACTGCGGCCGCTCCGTCCCCTCCGGCTTCCAGTGCAGCAACTAA 537
W0106       506 TCAACCTCCCCATCAACCTCAGCCTCCTCGTCAACTACTGCGGCCGCTCCGTCCCCTCCGGCTTCCAGTGCAGCAACTAA 585
W0652       518 TCAACCTCCCCATCAACCTCAGCCTCCTCGTCAACTACTGCGGCCGCTCCGTCCCCTCCGGCTTCCAGTGCAGCAACTAA 597
W1169       506 TCAACCTCCCCATCAACCTCAGCCTCCTCGTCAACTACTGCGGCCGCTCCGTCCCCTCCGGCTTCCAGTGCAGCAACTAA 585
W1413       506 TCAACCTCCCCATCAACCTCAGCCTCCTCGTCAACTACTGCGGCCGCTCTGTCCCTTCCGGCTTCCAGTGCAGCAACTAG 585
W1508       536 TCAACCTCCCCATCAACCTCAGCCTCCTCGTCAACTACTGCGGCCGCTCTGTCCCTTCCGGCTTCCAGTGCAGCAACTAG 615
```

Fig. 34

```
                  ***************  ***************************         **********
qLTG-3-1     1    MATKAGVIATLLALNLLFFTFSDACGCQCGSCPSPGGGGGGGGGGGGGGGG---RGGGGGSGGGSGGG------------ 65
Haplotype1   1    MATKAGVIATLLALNLLFFTFSDACGCQCGSCPSPGGGGGGGGGGGGGGGG---RGGGGGSGGGSGGG------------ 65
Haplotype2   1    MATKAGVIATLLALNLLFFTFSDACGCQCGSCPSPGGGGGGGGGGGGGGGG---RGGGGGSGGGSGGG------------ 65
Haplotype3   1    MATKAGVIATLLALNLLFFTFSDACGCQCGSCPSPGGGGGGGGGGGGGGGG---RGGGGGSGGGSGGG------------ 65
Haplotype4   1    MATKAGVIATLLALNLLFFTFSDACGCQCGSCPSPGGGGGGGGGGGGGGGG---RGGGGGSGGGSGGG------------ 65
Haplotype5   1    MATKAGVIATLLALNLHFFTFSDACGCQCGSCPSPGGGGGGGGGGGGGGGG---RGGGGGSGGGSGGG------------ 65
Haplotype6   1    MATKAGVIATLLALNLLFFTFSDACGCQCGSCPSPGGGGGGGGGG--------RGGGGGSGGG-----------G 56
Haplotype7   1    MATKAGVIATLLALNLLFFTFSDACGCQCGSCPSPGGGGGGGGGG--------RGGGGGSGGG-----------G 56
Haplotype8   1    MATKAGVIATLLALNLLFFTFSDACGCQCGSCPSPGGGGGGGGGG--------RGGGGGSGGG-----------G 56
Haplotype9   1    MATKAGVIATLLALNLLFFTFSDACGCQCGSCPSPGGGGGGGGGG--------RGGGGGSGGGSGGGSGGGGSGGGG--- 69
Haplotype10  1    MATKAGVIATLLALNLLFFTFSDACGCQCGSCPSPGGGGGGGGGG--------RGGGGGSGGG-----------G 56
W0106        1    MATKAGVIATLLALNLLFFTFSDACGCQCGSCPSPGGGGGGGGGGGGGGGG----RGGGGGSGGGSGGGSGGGGSGGGG---- 73
W0652        1    MATKAGVIATLLALNLLFFTFSDACGCQCGSCPSPGGGGGGGGGGGGGGGG----RGGGGGSGGGSGGGSGGGGSGGGGSGG 76
W1169        1    MATKAGVIATLLALNLLFFTFSDACGCQCGSCPSPGGGGGGGGGGGG--------RGGGGGSGGGSGGGSGGGRSGGGGSGG 72
W1413        1    MATKAGVIATLLALNLLFFTFSDACGCQCGSCPSPGGGGGGGGGGGGGGGGGGGGRGGGGGSGGGSGGGSGGGG----GSGG 76
W1508        1    MATKAGVIATLLALNLLFFTFSDACGCQCGSCPSPGGGGGGGGGGGG--------RGGGGGSGGGSGGG----GSGGG-SGG 67
```

Fig. 35

```
             ****  * ****         *****          *******      ********************
qLTG-3-1    65 ----GGSGGGGSGGGGS----------GGGGSGG---------GGGGGSGGGGGGG----RCPIDTLKLGVCANVLNGLINVQL 122
Haplotype1  65 ----GGSGGGGSGGGGS----------GGGGSGG---------GGGGGSGGGGGGG----RCPIDTLKLGVCANVLNGLINVQL 122
Haplotype2  65 ----GGSGGGGSGGGGS----------GGGGSGG---------GGGGGSGGGGGGG----RCPIDTLKLGVCANVLNGLINVQL 122
Haplotype3  65 ----GGSGGGGSGGGGS----------GGGGSGG---------GGGGGSGGGGGGG----RCPIDTLKLGVCANVLNGLINVQL 122
Haplotype4  65 ----GGSGGGGSGGGGS----------GGGGSGG---------GGGGGSGGGGGGG----RCPIDTLKLGVCANVLNGLINVQL 122
Haplotype5  65 ----GGSGGGGSGGGGS----------GGGGSGG---------GGGGGSGGGGGGG----RCPIDTLKLGVCANVLNGLINVQL 122
Haplotype6  57 GGGGGSGGGGSGGGGS-----------GGGGSGG---------GGGGGSGGGGGGG----RCPIDTLKLGVCANVLNGLINVQL 116
Haplotype7  57 GGGGGSGGGGSGGGGS-----------GGGGSGG---------GGGGGSGGGGGGG----RCPIDTLKLGVCANVLNGLINVQL 116
Haplotype8  57 GGGGGSGGGGSGGGGS-----------GGGGSGG---------GGGGGSGGGGGGG----RCPIDTLKLGVCANVLNGLINVQL 116
Haplotype9  69 -GGGGSGGGGSGGGGS-----------GGGGSGG---------GGGGGSGGGGGGG----RCPIDTLKLGVCANVLNGLINVQL 128
Haplotype10 57 GGGGGSGGGGSGGGGS-----------GGGGSGG---------GGGGGSGGGGGGG----RCPIDTLKLGVCANVLNGLINVQL 116
W0106       73 -GGGGSGGGGSGGGGS-----------GGGGSGG---------GGGGGSGGGGGGG----RCPIDTLKLGVCANVLNGLINVQL 132
W0652       77 GGGGGSGGGGSGGGGS-----------GGGGSGG---------GGGGGSGGGGGGG----RCPIDTLKLGVCANVLNGLINVQL 136
W1169       73 GGGGGSGGGGSGGGGS-----------GGGGSGG---------GGGGGSGGGGGGG----RCPIDTLKLGVCANVLNGLINVQL 132
W1413       77 G----SGGG-SGGGGSGGGGSGGGSGGGGS------------------GGGGGGG----RCPIDTLKLGVCANVLNGLINVQL 132
W1508       68 G-----SGGGGS-GGGSGGSGGGGSGGGGSGGGSGGGGSGGGGGSGGGGGGGSGGRCPIDTLKLGVCANVLNGLINVQL 142
```

Fig. 36

```
                        ************************************************************
qLTG-3-1     123 GTPPRQPCCSLIQGLADLEAAVCLCTALRANILGINLNLPINLSLLVNYCGRSVPSGFQCSN* 185
Haplotype1   123 GTPPRQPCCSLIQGLADLEAAVCLCTALRANILGINLNLPINLSLLVNYCGRSVPSGFQCSN* 185
Haplotype2   123 GTPPRQPCCSLIQGLADLEAAVCLCTALRANILGINLNLPINLSLLVNYCGRSVPSGFQCSN* 185
Haplotype3   123 GTPPRQPCCSLIQGLADLEAAVCLCTALRANILGINLNLPINLSLLVNYCGRSVPSGFQCSN* 185
Haplotype4   123 GTPPRQPCCSLIQGLADLEAAVCLCTALRANILGINLNLPINLSLLVNYCGRSVPSGFQCSN* 185
Haplotype5   123 GTPPRQPCCSLIQGLADLEAAVCLCTALRANILGINLNLPINLSLLVNYCGRSVPSGFQCSN* 185
Haplotype6   117 GTPPRQPCCSLIQGLADLEAAVCLCTALRANILGINLNLPINLSLLVNYCGRSVPSGFQCSN* 179
Haplotype7   117 GTPPRQPCCSLIQGLADLEAAVCLCTALRANILGINLNLPINLSLLVNYCGRSVPSGFQCSN* 179
Haplotype8   117 GTPPRQPCCSLIQGLADLEAAVCLCTALRANILGINLNLPINLSLLVNYCGRSVPSGFQCSN* 179
Haplotype9   129 GTPPRQPCCSLIQGLADLEAAVCLCTALRANILGINLNLPINLSLLVNYCGRSVPSGFQCSN* 191
Haplotype10  117 GTPPRQPCCSLIQGLADLEAAVCLCTALRANILGINLNLPINLSLLVNYCGRSVPSGFQCSN* 179
W0106        133 GTPPRQPCCSLIQGLADLEAAVCLCTALRANILGINLNLPINLSLLVNYCGRSVPSGFQCSN* 195
W0652        137 GTPPRQPCCSLIQGLADLEAAVCLCTALRANILGINLNLPINLSLLVNYCGRSVPSGFQCSN* 199
W1169        133 GTPPRQPCCSLIQGLADLEAAVCLCTALRANILGINLNLPINLSLLVNYCGRSVPSGFQCSN* 195
W1413        133 GTPPRQPCCSLIQGLADLEAAVCLCTALRANILGINLNLPINLSLLVNYCGRSVPSGFQCSN* 195
W1508        143 GTPPRQPCCSLIQGLADLEAAVCLCTALRANILGINLNLPINLSLLVNYCGRSVPSGFQCSN* 205
```

Fig. 37

SEQUENCE LISTING

```
<160> NUMBER OF SEQ ID NOS: 173

<210> SEQ ID NO 1
<211> LENGTH: 555
<212> TYPE: DNA
<213> ORGANISM: Oriza

<400> SEQUENCE: 1
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300 ccgatcgaca cgctgaagct ggggtgtgc gcgaacgtgc tgaatgggct gataaacgtg      360
cagctgggga cgccgccgcg gcagccgtgt tgcagcctca tccagggcct cgccgacctt    420
gaggccgccg tgtgcctctg caccgccctc cgcgccaaca tccttggcat caacctcaac    480
ctccccatca acctcagcct cctcgtcaac tactgcggcc gctccgtccc ctccggcttc    540
cagtgcagca actaa                                                      555

<210> SEQ ID NO 2
<211> LENGTH: 555
<212> TYPE: DNA
<213> ORGANISM: Oriza

<400> SEQUENCE: 2
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300 ccgatcgaca cgctgaagct ggggtgtgc gcgaacgtgc tgaatgggct gataaacgtg      360
cagctgggga cgccgccgcg gcagccgtgt tgcagcctca tccagggcct cgccgacctt    420
gaggccgccg tgtgcctctg caccgccctc cgcgccaaca tccttggcat caacctcaac    480
ctccccatca acctcagcct cctcgtcaac tactgcggcc gctccgtccc ctccggcttc    540
cagtgcagca actaa                                                      555

<210> SEQ ID NO 3
<211> LENGTH: 555
<212> TYPE: DNA
<213> ORGANISM: Oriza
```

<400> SEQUENCE: 3

```
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300
ccgatcgaca cgctgaagct ggggtgtgc gcgaacgtgc tgaatgggct gataaacgtg      360
cagctgggga cgccgccgcg gcagccgtgt tgcagcctca tccagggcct cgccgacctt     420
gaggccgccg tgtgcctctg caccgccctc cgcgccaaca tccttggcat caacctcaac     480
ctccccatca acctcagcct cctcgtcaac tactgcggcc gctccgtccc ctccggcttc     540
cagtgcagca actaa                                                      555
```

<210> SEQ ID NO 4
<211> LENGTH: 555
<212> TYPE: DNA
<213> ORGANISM: Oriza

<400> SEQUENCE: 4

```
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300
ccgatcgaca cgctgaagct ggggtgtgc gcgaacgtgc tgaatgggct gataaacgtg      360
cagctgggga cgccgccgcg gcagccgtgt tgcagcctca tccagggcct cgccgacctt     420
gaggccgccg tgtgcctctg caccgccctc cgcgccaaca tccttggcat caacctcaac     480
ctccccatca acctcagcct cctcgtcaac tactgcggcc gctccgtccc ctccggcttc     540
cagtgcagca actaa                                                      555
```

<210> SEQ ID NO 5
<211> LENGTH: 555
<212> TYPE: DNA
<213> ORGANISM: Oriza

<400> SEQUENCE: 5

```
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300
ccgatcgaca cgctgaagct ggggtgtgc gcgaacgtgc tgaatgggct gataaacgtg      360
cagctgggga cgccgccgcg gcagccgtgt tgcagcctca tccagggcct cgccgacctt     420
gaggccgccg tgtgcctctg caccgccctc cgcgccaaca tccttggcat caacctcaac     480
ctccccatca acctcagcct cctcgtcaac tactgcggcc gctccgtccc ctccggcttc     540
cagtgcagca actaa                                                      555
```

<210> SEQ ID NO 6

```
<211> LENGTH: 555
<212> TYPE: DNA
<213> ORGANISM: Oriza

<400> SEQUENCE: 6
atggcgacga aagctggggt gatcgccacg ctcctggccc tgaacctcca cttcttcacc    60
ttctccgacg cgtgcggctg ccagtgcggc tcatgccctc gtcccggcgg aggaggcggt   120
ggcggtggcg gtggcggtgg cggtggtgga gggcgtggag gtggtggcgg gagcggcgga   180
ggttcaggtg gaggcggcgg ttcaggtgga ggaggaagcg gcggcggagg ttcaggcggt   240
ggaggaagcg gaggcggcgg aggaggagga agcggcggcg gcggggagg aggaagatgc   300 ccgatcgaca cgctgaagct gggggtgtgc gcgaacgtgc tgaatgggct gataaacgtg   360
cagctgggga cgccgccgcg gcagccgtgt tgcagcctca tccagggcct cgccgacctt   420
gaggccgccg tgtgcctctg caccgccctc cgcgccaaca tccttggcat caacctcaac   480
ctccccatca acctcagcct cctcgtcaac tactgcggcc gctccgtccc ctccggcttc   540
cagtgcagca actaa                                                    555

<210> SEQ ID NO 7
<211> LENGTH: 537
<212> TYPE: DNA
<213> ORGANISM: Oriza

<400> SEQUENCE: 7
atggcgacga aagctggggt gatcgccacg ctcctggccc tgaacctcct cttcttcacc    60
ttctccgacg cgtgcggctg ccagtgcggc tcatgccctc gtcccggcgg aggaggcggt   120
ggcggtggtg gagggcgtgg aggtggtggc gggagcggcg gaggcggagg tggaggcggc   180
ggttcaggtg gaggaggaag cggcggcgga ggttcaggcg gtggaggaag cggaggcggc   240
ggaggaggag gaagcggcgg cggcggggga ggaggaagat gcccgatcga cacgctgaag   300
ctgggggtgt gcgcgaacgt gctgaatggg ctgataaacg tgcagctggg gacgccgccg   360
cggcagccgt gttgcagcct catccagggc ctcgccgacc ttgaggccgc cgtgtgcctc   420
tgcaccgccc tccgcgccaa catccttggc atcaacctca acctccccat caacctcagc   480
ctcctcgtca actactgcgg ccgctccgtc ccctccggct ccagtgcag caactaa      537

<210> SEQ ID NO 8
<211> LENGTH: 537
<212> TYPE: DNA
<213> ORGANISM: Oriza

<400> SEQUENCE: 8
atggcgacga aagctggggt gatcgccacg ctcctggccc tgaacctcct cttcttcacc    60
ttctccgacg cgtgcggctg ccagtgcggc tcatgccctc gtcccggcgg aggaggcggt   120
ggcggtggtg gagggcgtgg aggtggtggc gggagcggcg gaggcggagg tggaggcggc   180
ggttcaggtg gaggaggaag cggcggcgga ggttcaggcg gtggaggaag cggaggcggc   240
ggaggaggag gaagcggcgg cggcggggga ggaggaagat gcccgatcga cacgctgaag   300
ctgggggtgt gcgcgaacgt gctgaatggg ctgataaacg tgcagctggg gacgccgccg   360
cggcagccgt gttgcagcct catccagggc ctcgccgacc ttgaggccgc cgtgtgcctc   420
tgcaccgccc tccgcgccaa catccttggc atcaacctca acctccccat caacctcagc   480
ctcctcgtca actactgcgg ccgctccgtc ccctccggct ccagtgcag caactaa      537

<210> SEQ ID NO 9
```

```
<211> LENGTH: 537
<212> TYPE: DNA
<213> ORGANISM: Oriza

<400> SEQUENCE: 9
atggcgacga aagctggggt gatcgccacg ctcctggccc tgaacctcct cttcttcacc    60
ttctccgacg cgtgcggctg ccagtgcggc tcatgcccta gtcccggcgg aggaggcggt   120
ggcggtggtg gagggcgtgg aagtggtggc gggagcggcg gaggcggagg tgaggcggc    180
ggttcaggtg gaggaggaag cggcggcgga ggttcaggcg gtggaggaag cggaggcggc   240
ggaggaggag gaagcggcgg cggcggggga ggaggaagat gcccgatcga cacgctgaag   300
ctgggggtgt gcgcgaacgt gctgaatggg ctgataaacg tgcagctggg gacgccgccg   360
cggcagccgt gttgcagcct catccagggc ctcgccgacc ttgaggccgc cgtgtgcctc   420
tgcaccgccc tccgcgccaa catccttggc atcaacctca acctccccat caacctcagc   480
ctcctcgtca actactgcgg ccgctccgtc ccctccggct tccagtgcag caactaa      537

<210> SEQ ID NO 10
<211> LENGTH: 573
<212> TYPE: DNA
<213> ORGANISM: Oriza

<400> SEQUENCE: 10
atggcgacga aagctggggt gatcgccacg ctcctggccc tgaacctcct cttcttcacc    60
ttctccgacg cgtgcggctg ccagtgcggc tcatgcccta gtcccggcgg aggaggcggt   120
ggcggtggtg gagggcgtgg aagtggtggc gggagcggcg gaggttcagg tgggggttca   180
ggtggtggag gaagcggagg cggaggtgga ggcggcggtt caggtggagg aggaagcggc   240
ggcggaggtt caggcggtgg aggaagcgga ggcggcggag gaggaggaag cggcggcggc   300
gggggaggag gaagatgccc gatcgacacg ctgaagctgg gggtgtgcgc gaacgtgctg   360
aatgggctga taaacgtgca gctggggacg ccgccgcggc agccgtgttg cagcctcatc   420
cagggcctcg ccgaccttga ggccgccgtg tgcctctgca ccgccctccg ccaacatc    480
cttggcatca acctcaacct ccccatcaac ctcagcctcc tcgtcaacta ctgcggccgc   540
tccgtcccct ccggcttcca gtgcagcaac taa                                573

<210> SEQ ID NO 11
<211> LENGTH: 537
<212> TYPE: DNA
<213> ORGANISM: Oriza

<400> SEQUENCE: 11
atggcgacga aagctggggt gatcgccacg ctcctggccc tgaacctcct cttcttcacc    60
ttctccgacg cgtgcggctg ccagtgcggc tcatgcccta gtcccggcgg aggaggcggt   120
ggcggtggtg gagggcgtgg aagtggtggc gggagcggcg gaggcggagg tgaggcggc    180
ggttcaggtg gaggaggaag cggcggcgga ggttcaggcg gtggaggaag cggaggcggc   240
ggaggaggag gaagcggcgg cggcggggga ggaggaagat gcccgatcga cacgctgaag   300
ctgggggtgt gcgcgaacgt gctgaatggg ctgataaacg tgcagctggg gacgccgccg   360
cggcagccgt gttgcagcct catccagggc ctcgccgacc ttgaggccgc cgtgtgcctc   420
tgcaccgccc tccgcgccaa catccttggc atcaacctca acctccccat caacctcagc   480
ctcctcgtca actactgcgg ccgctccgtc ccctccggct tccagtgcag caactaa      537

<210> SEQ ID NO 12
```

```
<211> LENGTH: 585
<212> TYPE: DNA
<213> ORGANISM: Oriza

<400> SEQUENCE: 12
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg tggagggcgt ggaggtggtg gcgggagcgg cggaggttca     180
ggtgggggtt caggtggtgg aggaagcgga ggcggaggtg gaggcggcgg ttcaggtgga     240
ggaggaagcg gcggcggagg ttcaggcggt ggaggaagcg gaggcggcgg aggaggagga     300
agcggcggcg gcggggagg aggaagatgc cgatcgaca cgctgaagct ggggtgtgc        360
gcgaacgtgc tgaatgggct gataaacgtg cagctgggga cgccgccgcg gcagccgtgt     420
tgcagcctca tccagggcct cgccgacctt gaggccgccg tgtgcctctg caccgccctc     480
cgcgccaaca tccttggcat caacctcaac ctccccatca acctcagcct cctcgtcaac     540
tactgcggcc gctccgtccc ctccggcttc cagtgcagca actaa                     585

<210> SEQ ID NO 13
<211> LENGTH: 597
<212> TYPE: DNA
<213> ORGANISM: Oriza

<400> SEQUENCE: 13
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg tggagggcgt ggaggtggtg gcgggagcgg cggaggttca     180
ggtgggggtt caggtggtgg aggaagcgga ggcggaggtt caggcggagg tggaggcggc     240
ggttcaggtg gaggaggaag cggcggcgga ggttcaggcg gtggaggaag cggaggcggc     300
ggaggaggag gaagcggcgg cggcggggga ggaggaagat gcccgatcga cacgctgaag     360
ctggggtgt gcgcgaacgt gctgaatggg ctgataaacg tgcagctggg gacgccgccg       420
cggcagccgt gttgcagcct catccagggc ctcgccgacc ttgaggccgc cgtgtgcctc     480
tgcaccgccc tccgcgccaa catccttggc atcaacctca acctccccat caacctcagc     540
ctcctcgtca actactgcgg ccgctccgtc ccctccggct ccagtgcag caactaa          597

<210> SEQ ID NO 14
<211> LENGTH: 585
<212> TYPE: DNA
<213> ORGANISM: Oriza

<400> SEQUENCE: 14
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggtg gagggcgtgg aggaggtggc gggagcggcg gaggttcagg tgggggttca     180
ggtggtggac gaagcggagg cggaggttca ggcggaggtg gaggcggcgg ttcaggtgga     240
ggaggaagcg gcggcggagg ttcaggcggt ggaggaagcg gaggcggcgg aggaggagga     300
agcggcggcg gcggggagg aggaagatgc cgatcgaca cgctgaagct ggggtgtgc        360
gcgaacgtgc tgaatgggct gataaacgtg cagctgggga cgccgccgcg gcagccgtgt     420
tgcagcctca tccagggcct cgccgacctt gaggccgccg tgtgcctctg caccgccctc     480
cgcgccaaca tccttggcat caacctcaac ctccccatca acctcagcct cctcgtcaac     540
```

-continued

```
tactgcggcc gctccgtccc ctccggcttc cagtgcagca actaa            585
```

```
<210> SEQ ID NO 15
<211> LENGTH: 585
<212> TYPE: DNA
<213> ORGANISM: Oriza

<400> SEQUENCE: 15
atggcgacga aagctggggt gatcgccacg ctcctggccc tgaacctcct cttcttcacc    60
ttctccgacg cctgcggctg ccagtgcggc tcatgcccta gtcccggcgg aggaggcgga   120
ggcggaggcg gaggcggtgg cggtggcggt ggcggaggcg tggaggtgg tggcgggagc    180
ggcggaggtt caggtggggg ttctggcggt ggtggaggaa gcggcggagg ttcaggtgga   240
ggatcaggtg gtggaggaag cggaggcgga ggttcaggcg gtggaagcgg cggcggcggg   300
tcaggtggcg gcggaggcgg aggaagatgc ccgatcgaca cgctgaagct ggggtgtgc    360
gcgaacgtgc tgaacgggct gataaacgtg cagctgggga cgccgccgcg gcagccgtgc   420
tgcagcctca tccaggggct cgccgacctt gaggccgccg tgtgcctctg caccgccctc   480
cgcgccaaca tccttggcat caacctcaac ctccccatca acctcagcct cctcgtcaac   540
tactgcggcc gctctgtccc ttccggcttc cagtgcagca actag             585
```

```
<210> SEQ ID NO 16
<211> LENGTH: 615
<212> TYPE: DNA
<213> ORGANISM: Oriza

<400> SEQUENCE: 16
atggcgacga aagctggggt gatcgccacg ctcctggccc tgaacctcct cttcttcacc    60
ttctccgacg cctgcggctg ccagtgcggc tcatgcccta gtcccggcgg aggaggcggt   120
ggcggtggcg gagggcgtgg gggtggtggt gggagcggcg aggttcagg tggtggagga    180
agcggcggag gttcaggtgg aggatcaggt ggtggaggaa gcggcggagg ttcaggtgga   240
ggatcaggtg gtggaggaag cggaggcgga ggttcaggcg gtggaagcgg aggcggtgga   300
ggaagcggcg gaggaggagg aagcggcggc ggcggggag gaggaagcgg aggaagatgc   360
ccgatcgaca cgctgaagct ggggtgtgc gcgaacgtgc tgaatgggct gataaacgtg    420
cagctgggga cgccgccgcg gcagccgtgc tgcagcctca tccaggggct cgccgacctt   480
gaggccgccg tgtgcctctg caccgccctc cgcgccaaca tccttggcat caacctcaac   540
ctccccatca acctcagcct cctcgtcaac tactgcggcc gctctgtccc ttccggcttc   600
cagtgcagca actag                                              615
```

```
<210> SEQ ID NO 17
<211> LENGTH: 184
<212> TYPE: PRT
<213> ORGANISM: Oriza

<400> SEQUENCE: 17

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly Gly
            35                  40                  45

Gly Gly Gly Arg Gly Gly Gly Gly Ser Gly Gly Gly Ser Gly Gly
        50                  55                  60
```

```
Gly Gly Gly Ser Gly Gly Gly Ser Gly Gly Gly Ser Gly Gly
 65                  70                  75                  80

Gly Gly Ser Gly Gly Gly Gly Gly Ser Gly Gly Gly Gly Gly
                 85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Arg Gln
            115                 120                 125

Pro Cys Cys Ser Leu Ile Gln Gly Leu Ala Asp Leu Glu Ala Ala Val
        130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 18
<211> LENGTH: 184
<212> TYPE: PRT
<213> ORGANISM: Oriza

<400> SEQUENCE: 18

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly Gly
            35                  40                  45

Gly Gly Gly Arg Gly Gly Gly Gly Ser Gly Gly Gly Ser Gly Gly
         50                  55                  60

Gly Gly Gly Ser Gly Gly Gly Ser Gly Gly Gly Ser Gly Gly
 65                  70                  75                  80

Gly Gly Ser Gly Gly Gly Gly Gly Ser Gly Gly Gly Gly Gly
                 85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Arg Gln
            115                 120                 125

Pro Cys Cys Ser Leu Ile Gln Gly Leu Ala Asp Leu Glu Ala Ala Val
        130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 19
<211> LENGTH: 184
<212> TYPE: PRT
<213> ORGANISM: Oriza

<400> SEQUENCE: 19

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
```

```
            20                  25                  30

Pro Ser Pro Gly Gly Gly Gly Gly Gly Gly Gly Gly Gly
        35                  40                  45

Gly Gly Gly Arg Gly Gly Gly Gly Ser Gly Gly Ser Gly Gly
    50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
                85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Arg Gln
        115                 120                 125

Pro Cys Cys Ser Leu Ile Gln Gly Leu Ala Asp Leu Glu Ala Ala Val
        130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 20
<211> LENGTH: 184
<212> TYPE: PRT
<213> ORGANISM: Oriza

<400> SEQUENCE: 20

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Gly
        35                  40                  45

Gly Gly Gly Arg Gly Gly Gly Gly Ser Gly Gly Ser Gly Gly
    50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
                85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Arg Gln
        115                 120                 125

Pro Cys Cys Ser Leu Ile Gln Gly Leu Ala Asp Leu Glu Ala Ala Val
        130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 21
<211> LENGTH: 184
<212> TYPE: PRT
```

<213> ORGANISM: Oriza

<400> SEQUENCE: 21

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Gly Gly Gly Gly
        35                  40                  45

Gly Gly Gly Arg Gly Gly Gly Gly Ser Gly Gly Ser Gly Gly
    50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
            85                  90                  95

Gly Gly Arg Cys Pro Ile Asp Thr Leu Lys Leu Gly Val Cys Ala Asn
        100                 105                 110

Val Leu Asn Gly Leu Ile Asn Val Gln Leu Gly Thr Pro Pro Arg Gln
            115                 120                 125

Pro Cys Cys Ser Leu Ile Gln Gly Leu Ala Asp Leu Glu Ala Ala Val
        130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 22
<211> LENGTH: 184
<212> TYPE: PRT
<213> ORGANISM: Oriza

<400> SEQUENCE: 22

Met Ala Thr Lys Ala Gly Val Ile Ala Thr Leu Leu Ala Leu Asn Leu
1               5                   10                  15

His Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Gly Gly Gly Gly
        35                  40                  45

Gly Gly Gly Arg Gly Gly Gly Gly Ser Gly Gly Ser Gly Gly
    50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
            85                  90                  95

Gly Gly Arg Cys Pro Ile Asp Thr Leu Lys Leu Gly Val Cys Ala Asn
        100                 105                 110

Val Leu Asn Gly Leu Ile Asn Val Gln Leu Gly Thr Pro Pro Arg Gln
            115                 120                 125

Pro Cys Cys Ser Leu Ile Gln Gly Leu Ala Asp Leu Glu Ala Ala Val
        130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

```
Pro Ser Gly Phe Gln Cys Ser Asn
            180

<210> SEQ ID NO 23
<211> LENGTH: 178
<212> TYPE: PRT
<213> ORGANISM: Oriza

<400> SEQUENCE: 23

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Arg Gly Gly
        35                  40                  45

Gly Gly Gly Ser Gly Gly Gly Gly Gly Gly Gly Ser Gly Gly
        50                  55                  60

Gly Gly Ser Gly Gly Gly Ser Gly Gly Gly Ser Gly Gly Gly
65                  70                  75                  80

Gly Gly Gly Gly Ser Gly Gly Gly Gly Gly Arg Cys Pro Ile
                85                  90                  95

Asp Thr Leu Lys Leu Gly Val Cys Ala Asn Val Leu Asn Gly Leu Ile
            100                 105                 110

Asn Val Gln Leu Gly Thr Pro Pro Arg Gln Pro Cys Cys Ser Leu Ile
        115                 120                 125

Gln Gly Leu Ala Asp Leu Glu Ala Ala Val Cys Leu Cys Thr Ala Leu
    130                 135                 140

Arg Ala Asn Ile Leu Gly Ile Asn Leu Asn Leu Pro Ile Asn Leu Ser
145                 150                 155                 160

Leu Leu Val Asn Tyr Cys Gly Arg Ser Val Pro Ser Gly Phe Gln Cys
                165                 170                 175

Ser Asn

<210> SEQ ID NO 24
<211> LENGTH: 178
<212> TYPE: PRT
<213> ORGANISM: Oriza

<400> SEQUENCE: 24

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Arg Gly Gly
        35                  40                  45

Gly Gly Gly Ser Gly Gly Gly Gly Gly Gly Gly Ser Gly Gly
        50                  55                  60

Gly Gly Ser Gly Gly Gly Ser Gly Gly Gly Ser Gly Gly Gly
65                  70                  75                  80

Gly Gly Gly Gly Ser Gly Gly Gly Gly Gly Arg Cys Pro Ile
                85                  90                  95

Asp Thr Leu Lys Leu Gly Val Cys Ala Asn Val Leu Asn Gly Leu Ile
            100                 105                 110

Asn Val Gln Leu Gly Thr Pro Pro Arg Gln Pro Cys Cys Ser Leu Ile
        115                 120                 125

Gln Gly Leu Ala Asp Leu Glu Ala Ala Val Cys Leu Cys Thr Ala Leu
```

```
                130                 135                 140
Arg Ala Asn Ile Leu Gly Ile Asn Leu Asn Leu Pro Ile Asn Leu Ser
145                 150                 155                 160

Leu Leu Val Asn Tyr Cys Gly Arg Ser Val Pro Ser Gly Phe Gln Cys
                165                 170                 175

Ser Asn

<210> SEQ ID NO 25
<211> LENGTH: 178
<212> TYPE: PRT
<213> ORGANISM: Oriza

<400> SEQUENCE: 25

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Arg Gly Gly
            35                  40                  45

Gly Gly Gly Ser Gly Gly Gly Gly Gly Gly Gly Ser Gly Gly
50                  55                  60

Gly Gly Ser Gly Gly Gly Ser Gly Gly Gly Ser Gly Gly
65                  70                  75                  80

Gly Gly Gly Gly Ser Gly Gly Gly Gly Gly Arg Cys Pro Ile
                85                  90                  95

Asp Thr Leu Lys Leu Gly Val Cys Ala Asn Val Leu Asn Gly Leu Ile
                100                 105                 110

Asn Val Gln Leu Gly Thr Pro Pro Arg Gln Pro Cys Cys Ser Leu Ile
                115                 120                 125

Gln Gly Leu Ala Asp Leu Glu Ala Ala Val Cys Leu Cys Thr Ala Leu
130                 135                 140

Arg Ala Asn Ile Leu Gly Ile Asn Leu Asn Leu Pro Ile Asn Leu Ser
145                 150                 155                 160

Leu Leu Val Asn Tyr Cys Gly Arg Ser Val Pro Ser Gly Phe Gln Cys
                165                 170                 175

Ser Asn

<210> SEQ ID NO 26
<211> LENGTH: 190
<212> TYPE: PRT
<213> ORGANISM: Oriza

<400> SEQUENCE: 26

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Arg Gly Gly
            35                  40                  45

Gly Gly Gly Ser Gly Gly Ser Gly Gly Ser Gly Gly Gly Gly
50                  55                  60

Ser Gly Gly Gly Gly Gly Gly Ser Gly Gly Gly Gly Ser Gly
65                  70                  75                  80

Gly Gly Ser Gly Gly Gly Ser Gly Gly Gly Gly Gly
                85                  90                  95

Ser Gly Gly Gly Gly Gly Gly Gly Arg Cys Pro Ile Asp Thr Leu Lys
```

```
                    100                 105                 110
Leu Gly Val Cys Ala Asn Val Leu Asn Gly Leu Ile Asn Val Gln Leu
            115                 120                 125

Gly Thr Pro Pro Arg Gln Pro Cys Cys Ser Leu Ile Gln Gly Leu Ala
        130                 135                 140

Asp Leu Glu Ala Ala Val Cys Leu Cys Thr Ala Leu Arg Ala Asn Ile
145                 150                 155                 160

Leu Gly Ile Asn Leu Asn Leu Pro Ile Asn Leu Ser Leu Leu Val Asn
                165                 170                 175

Tyr Cys Gly Arg Ser Val Pro Ser Gly Phe Gln Cys Ser Asn
            180                 185                 190

<210> SEQ ID NO 27
<211> LENGTH: 178
<212> TYPE: PRT
<213> ORGANISM: Oriza

<400> SEQUENCE: 27

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Arg Gly Gly
        35                  40                  45

Gly Gly Gly Ser Gly Gly Gly Gly Gly Gly Gly Ser Gly Gly
    50                  55                  60

Gly Gly Ser Gly Gly Gly Ser Gly Gly Gly Ser Gly Gly Gly
65                  70                  75                  80

Gly Gly Gly Gly Ser Gly Gly Gly Gly Gly Arg Cys Pro Ile
                85                  90                  95

Asp Thr Leu Lys Leu Gly Val Cys Ala Asn Val Leu Asn Gly Leu Ile
            100                 105                 110

Asn Val Gln Leu Gly Thr Pro Pro Arg Gln Pro Cys Cys Ser Leu Ile
        115                 120                 125

Gln Gly Leu Ala Asp Leu Glu Ala Ala Val Cys Leu Cys Thr Ala Leu
    130                 135                 140

Arg Ala Asn Ile Leu Gly Ile Asn Leu Asn Leu Pro Ile Asn Leu Ser
145                 150                 155                 160

Leu Leu Val Asn Tyr Cys Gly Arg Ser Val Pro Ser Gly Phe Gln Cys
                165                 170                 175

Ser Asn

<210> SEQ ID NO 28
<211> LENGTH: 194
<212> TYPE: PRT
<213> ORGANISM: Oriza

<400> SEQUENCE: 28

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Gly Gly
        35                  40                  45

Gly Arg Gly Gly Gly Gly Ser Gly Gly Gly Ser Gly Gly Gly Ser
    50                  55                  60
```

```
Gly Gly Gly Gly Ser Gly Gly Gly Gly Gly Ser Gly Gly
65                  70                  75                  80

Gly Gly Ser Gly Gly Gly Ser Gly Gly Ser Gly Gly
            85                  90                  95

Gly Gly Gly Gly Ser Gly Gly Gly Gly Arg Cys Pro Ile
            100                 105                 110

Asp Thr Leu Lys Leu Gly Val Cys Ala Asn Val Leu Asn Gly Leu Ile
                115                 120                 125

Asn Val Gln Leu Gly Thr Pro Pro Arg Gln Pro Cys Cys Ser Leu Ile
            130                 135                 140

Gln Gly Leu Ala Asp Leu Glu Ala Ala Val Cys Leu Cys Thr Ala Leu
145                 150                 155                 160

Arg Ala Asn Ile Leu Gly Ile Asn Leu Asn Leu Pro Ile Asn Leu Ser
                165                 170                 175

Leu Leu Val Asn Tyr Cys Gly Arg Ser Val Pro Ser Gly Phe Gln Cys
                180                 185                 190

Ser Asn

<210> SEQ ID NO 29
<211> LENGTH: 198
<212> TYPE: PRT
<213> ORGANISM: Oriza

<400> SEQUENCE: 29

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly
            35                  40                  45

Gly Arg Gly Gly Gly Gly Ser Gly Gly Ser Gly Gly Ser
    50                  55                  60

Gly Gly Gly Gly Ser Gly Gly Gly Ser Gly Gly Gly Gly
65                  70                  75                  80

Gly Ser Gly Gly Gly Ser Gly Gly Gly Ser Gly Gly Gly
                85                  90                  95

Ser Gly Gly Gly Gly Gly Ser Gly Gly Gly Gly Gly Gly
            100                 105                 110

Arg Cys Pro Ile Asp Thr Leu Lys Leu Gly Val Cys Ala Asn Val Leu
                115                 120                 125

Asn Gly Leu Ile Asn Val Gln Leu Gly Thr Pro Pro Arg Gln Pro Cys
            130                 135                 140

Cys Ser Leu Ile Gln Gly Leu Ala Asp Leu Glu Ala Ala Val Cys Leu
145                 150                 155                 160

Cys Thr Ala Leu Arg Ala Asn Ile Leu Gly Ile Asn Leu Asn Leu Pro
                165                 170                 175

Ile Asn Leu Ser Leu Leu Val Asn Tyr Cys Gly Arg Ser Val Pro Ser
                180                 185                 190

Gly Phe Gln Cys Ser Asn
            195

<210> SEQ ID NO 30
<211> LENGTH: 194
<212> TYPE: PRT
<213> ORGANISM: Oriza

<400> SEQUENCE: 30
```

```
Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Arg Gly Gly
            35                  40                  45

Gly Gly Gly Ser Gly Gly Ser Gly Gly Ser Gly Gly Arg
50                  55                  60

Ser Gly Gly Gly Ser Gly Gly Gly Gly Gly Ser Gly Gly
65                  70                  75                  80

Gly Gly Ser Gly Gly Gly Ser Gly Gly Gly Ser Gly Gly
            85                  90                  95

Gly Gly Gly Gly Ser Gly Gly Gly Gly Gly Arg Cys Pro Ile
                100                 105                 110

Asp Thr Leu Lys Leu Gly Val Cys Ala Asn Val Leu Asn Gly Leu Ile
            115                 120                 125

Asn Val Gln Leu Gly Thr Pro Pro Arg Gln Pro Cys Cys Ser Leu Ile
        130                 135                 140

Gln Gly Leu Ala Asp Leu Glu Ala Val Cys Leu Cys Thr Ala Leu
145                 150                 155                 160

Arg Ala Asn Ile Leu Gly Ile Asn Leu Asn Leu Pro Ile Asn Leu Ser
                165                 170                 175

Leu Leu Val Asn Tyr Cys Gly Arg Ser Val Pro Ser Gly Phe Gln Cys
            180                 185                 190

Ser Asn

<210> SEQ ID NO 31
<211> LENGTH: 194
<212> TYPE: PRT
<213> ORGANISM: Oriza

<400> SEQUENCE: 31

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly
            35                  40                  45

Gly Gly Gly Gly Gly Arg Gly Gly Gly Gly Ser Gly Gly Ser
50                  55                  60

Gly Gly Ser Gly Gly Gly Gly Ser Gly Gly Ser Gly Gly
65                  70                  75                  80

Gly Ser Gly Gly Gly Gly Ser Gly Gly Gly Ser Gly Gly Ser
            85                  90                  95

Gly Gly Gly Gly Ser Gly Gly Gly Gly Gly Arg Cys Pro Ile
                100                 105                 110

Asp Thr Leu Lys Leu Gly Val Cys Ala Asn Val Leu Asn Gly Leu Ile
            115                 120                 125

Asn Val Gln Leu Gly Thr Pro Pro Arg Gln Pro Cys Cys Ser Leu Ile
        130                 135                 140

Gln Gly Leu Ala Asp Leu Glu Ala Val Cys Leu Cys Thr Ala Leu
145                 150                 155                 160

Arg Ala Asn Ile Leu Gly Ile Asn Leu Asn Leu Pro Ile Asn Leu Ser
                165                 170                 175
```

Leu Leu Val Asn Tyr Cys Gly Arg Ser Val Pro Ser Gly Phe Gln Cys
            180                 185                 190

Ser Asn

<210> SEQ ID NO 32
<211> LENGTH: 203
<212> TYPE: PRT
<213> ORGANISM: Oriza

<400> SEQUENCE: 32

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Arg Gly Gly
        35                  40                  45

Gly Gly Gly Ser Gly Gly Ser Gly Gly Gly Ser Gly Gly
    50                  55                  60

Ser Gly Gly Gly Ser Gly Gly Gly Ser Gly Gly Ser Gly Gly
65                  70                  75                  80

Gly Ser Gly Gly Gly Ser Gly Gly Gly Ser Gly Gly Ser
                85                  90                  95

Gly Gly Gly Gly Ser Gly Gly Gly Ser Gly Gly Gly
            100                 105                 110

Gly Gly Gly Ser Gly Gly Arg Cys Pro Ile Asp Thr Leu Lys Leu Gly
        115                 120                 125

Val Cys Ala Asn Val Leu Asn Gly Leu Ile Asn Val Gln Leu Gly Thr
130                 135                 140

Pro Pro Arg Gln Pro Cys Cys Ser Leu Ile Gln Gly Leu Ala Asp Leu
145                 150                 155                 160

Glu Ala Ala Val Cys Leu Cys Thr Ala Leu Arg Ala Asn Ile Leu Gly
                165                 170                 175

Ile Leu Asn Leu Pro Ile Asn Leu Ser Leu Leu Val Asn Tyr Cys Gly
            180                 185                 190

Arg Ser Val Pro Ser Gly Phe Gln Cys Ser Asn
        195                 200

<210> SEQ ID NO 33
<211> LENGTH: 39
<212> TYPE: DNA
<213> ORGANISM: Artificial Sequence
<220> FEATURE:
<223> OTHER INFORMATION: Primer based on Oriza

<400> SEQUENCE: 33
cgcggatccc ttcgtaattc agcagggccg ggcaaataa                                   39

<210> SEQ ID NO 34
<211> LENGTH: 44
<212> TYPE: DNA
<213> ORGANISM: Artificial Sequence
<220> FEATURE:
<223> OTHER INFORMATION: Primer based on Oriza

<400> SEQUENCE: 34
aatgagctcg tgttgtgaaa acaaacagct agtatgtatg tgtg                             44

<210> SEQ ID NO 35
<211> LENGTH: 32
<212> TYPE: DNA

```
<213> ORGANISM: Artificial Sequence
<220> FEATURE:
<223> OTHER INFORMATION: Primer based on Oriza

<400> SEQUENCE: 35
gttaagcttc ttcgtaattc agcagggccg gg                              32

<210> SEQ ID NO 36
<211> LENGTH: 32
<212> TYPE: DNA
<213> ORGANISM: Artificial Sequence
<220> FEATURE:
<223> OTHER INFORMATION: Primer based on Oriza

<400> SEQUENCE: 36
cgaggatccg cccacccacc gcactgcacc tg                              32

<210> SEQ ID NO 37
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 37
ttgcctcccg caggtatatt a                                          21

<210> SEQ ID NO 38
<211> LENGTH: 25
<212> TYPE: DNA
<213> ORGANISM: Artificial Sequence
<220> FEATURE:
<223> OTHER INFORMATION: Primer based on Oriza

<400> SEQUENCE: 38
ccagctacca catcacttaa ctaac                                      25

<210> SEQ ID NO 39
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 39
aggttggttt ttatgggacg                                            20

<210> SEQ ID NO 40
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 40
ggcttttggt agcttagctg                                            20

<210> SEQ ID NO 41
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 41
cagctaagct accaaaagcc ca                                         22
```

```
<210> SEQ ID NO 42
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 42
ttatcagccc attcagcacg tt                                              22

<210> SEQ ID NO 43
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 43
gctcgctagc agagtacttg g                                               21

<210> SEQ ID NO 44
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 44
aacgtgctga atgggctgat                                                 20

<210> SEQ ID NO 45
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 45
ccgatggatc gaacaagagc                                                 20

<210> SEQ ID NO 46
<211> LENGTH: 27
<212> TYPE: DNA
<213> ORGANISM: Artificial Sequence
<220> FEATURE:
<223> OTHER INFORMATION: Primer based on Oriza

<400> SEQUENCE: 46
tgatatattc tagtacgatg aatctgg                                         27

<210> SEQ ID NO 47
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 47
agacaaaccc ttgatttccg tg                                              22

<210> SEQ ID NO 48
<211> LENGTH: 23
<212> TYPE: DNA
<213> ORGANISM: Artificial Sequence
<220> FEATURE:
<223> OTHER INFORMATION: Primer based on Oriza
```

<400> SEQUENCE: 48
gaacgtgctg aatgggctga taa    23

<210> SEQ ID NO 49
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 49
cgatggatcg aacaagagct a    21

<210> SEQ ID NO 50
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 50
atgtgatgct tgttggtgcg ta    22

<210> SEQ ID NO 51
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 51
ttgatgtcgt tcatctggac g    21

<210> SEQ ID NO 52
<211> LENGTH: 23
<212> TYPE: DNA
<213> ORGANISM: Artificial Sequence
<220> FEATURE:
<223> OTHER INFORMATION: Primer based on Oriza

<400> SEQUENCE: 52
ttcctgctgc agaaggtgct gaa    23

<210> SEQ ID NO 53
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 53
gagccatgct tatgcttacc ta    22

<210> SEQ ID NO 54
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 54
aagatccgca tccacgactt c    21

<210> SEQ ID NO 55
<211> LENGTH: 21
<212> TYPE: DNA

<213> ORGANISM: Artificial Sequence
<220> FEATURE:
<223> OTHER INFORMATION: Primer based on Oriza

<400> SEQUENCE: 55
gttcagctgc ttgatggcct c         21

<210> SEQ ID NO 56
<211> LENGTH: 25
<212> TYPE: DNA
<213> ORGANISM: Artificial Sequence
<220> FEATURE:
<223> OTHER INFORMATION: Primer based on Oriza

<400> SEQUENCE: 56
acgaattgag gaggcagcat ctatg         25

<210> SEQ ID NO 57
<211> LENGTH: 25
<212> TYPE: DNA
<213> ORGANISM: Artificial Sequence
<220> FEATURE:
<223> OTHER INFORMATION: Primer based on Oriza

<400> SEQUENCE: 57
gagcaagttc ttgcataccc aactc         25

<210> SEQ ID NO 58
<211> LENGTH: 28
<212> TYPE: DNA
<213> ORGANISM: Artificial Sequence
<220> FEATURE:
<223> OTHER INFORMATION: Primer based on Oriza

<400> SEQUENCE: 58
gacaagggac cagctccaga cattggag         28

<210> SEQ ID NO 59
<211> LENGTH: 28
<212> TYPE: DNA
<213> ORGANISM: Artificial Sequence
<220> FEATURE:
<223> OTHER INFORMATION: Primer based on Oriza

<400> SEQUENCE: 59
caggagcagc aatctgctca tccatggc         28

<210> SEQ ID NO 60
<211> LENGTH: 28
<212> TYPE: DNA
<213> ORGANISM: Artificial Sequence
<220> FEATURE:
<223> OTHER INFORMATION: Primer based on Oriza

<400> SEQUENCE: 60
atttcttccc ctacctcagc tgggttcc         28

<210> SEQ ID NO 61
<211> LENGTH: 28
<212> TYPE: DNA
<213> ORGANISM: Artificial Sequence
<220> FEATURE:
<223> OTHER INFORMATION: Primer based on Oriza

<400> SEQUENCE: 61
ctctatgagt gcctcccaca ctagcatc         28

```
<210> SEQ ID NO 62
<211> LENGTH: 28
<212> TYPE: DNA
<213> ORGANISM: Artificial Sequence
<220> FEATURE:
<223> OTHER INFORMATION: Primer based on Oriza

<400> SEQUENCE: 62
gagatcgtcg acgtcctcat catgtacc                                      28

<210> SEQ ID NO 63
<211> LENGTH: 28
<212> TYPE: DNA
<213> ORGANISM: Artificial Sequence
<220> FEATURE:
<223> OTHER INFORMATION: Primer based on Oriza

<400> SEQUENCE: 63
agatgttgac gcagcgaagt gtctcgtc                                      28

<210> SEQ ID NO 64
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 64
gctgtcgttc cggtactcat c                                             21

<210> SEQ ID NO 65
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 65
tggaagaatc gccggaagta gt                                            22

<210> SEQ ID NO 66
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 66
gctgacgatc atggaactcc t                                             21

<210> SEQ ID NO 67
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 67
tcttatacct cccgttcgac a                                             21

<210> SEQ ID NO 68
<211> LENGTH: 22
<212> TYPE: DNA
<213> ORGANISM: Artificial Sequence
<220> FEATURE:
<223> OTHER INFORMATION: Primer based on Oriza
```

```
<400> SEQUENCE: 68
aaggagacca tgtcgttcaa ct                                              22

<210> SEQ ID NO 69
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 69
tagtggttca gccgcatcac cg                                              22

<210> SEQ ID NO 70
<211> LENGTH: 23
<212> TYPE: DNA
<213> ORGANISM: Artificial Sequence
<220> FEATURE:
<223> OTHER INFORMATION: Primer based on Oriza

<400> SEQUENCE: 70
tccaccgtcg ccgattactt ctc                                             23

<210> SEQ ID NO 71
<211> LENGTH: 24
<212> TYPE: DNA
<213> ORGANISM: Artificial Sequence
<220> FEATURE:
<223> OTHER INFORMATION: Primer based on Oriza

<400> SEQUENCE: 71
tcctcgaaga actccctgta gtat                                            24

<210> SEQ ID NO 72
<211> LENGTH: 24
<212> TYPE: DNA
<213> ORGANISM: Artificial Sequence
<220> FEATURE:
<223> OTHER INFORMATION: Primer based on Oriza

<400> SEQUENCE: 72
aggagtacga ctcgtcgatg agag                                            24

<210> SEQ ID NO 73
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 73
atgaaggtga agaagcctga gt                                              22

<210> SEQ ID NO 74
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 74
tccttcttct ccaagctcat gt                                              22

<210> SEQ ID NO 75
<211> LENGTH: 21
<212> TYPE: DNA
```

<210> SEQ ID NO 75
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 75
cgaaggtgaa gaagcccgag t                                             21

<210> SEQ ID NO 76
<211> LENGTH: 23
<212> TYPE: DNA
<213> ORGANISM: Artificial Sequence
<220> FEATURE:
<223> OTHER INFORMATION: Primer based on Oriza

<400> SEQUENCE: 76
ttttcgtcaa tgttggtgat gtc                                           23

<210> SEQ ID NO 77
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 77
tatgcttttc cctcactggc at                                            22

<210> SEQ ID NO 78
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 78
tcgagtacct gctactctgc ct                                            22

<210> SEQ ID NO 79
<211> LENGTH: 23
<212> TYPE: DNA
<213> ORGANISM: Artificial Sequence
<220> FEATURE:
<223> OTHER INFORMATION: Primer based on Oriza

<400> SEQUENCE: 79
tagtggttca ccctgaggat gga                                           23

<210> SEQ ID NO 80
<211> LENGTH: 23
<212> TYPE: DNA
<213> ORGANISM: Artificial Sequence
<220> FEATURE:
<223> OTHER INFORMATION: Primer based on Oriza

<400> SEQUENCE: 80
aggtgttccg cgtgaaccac tac                                           23

<210> SEQ ID NO 81
<211> LENGTH: 24
<212> TYPE: DNA
<213> ORGANISM: Artificial Sequence
<220> FEATURE:
<223> OTHER INFORMATION: Primer based on Oriza

<400> SEQUENCE: 81
gaaaccctag actttaggct gttg                                          24

```
<210> SEQ ID NO 82
<211> LENGTH: 23
<212> TYPE: DNA
<213> ORGANISM: Artificial Sequence
<220> FEATURE:
<223> OTHER INFORMATION: Primer based on Oriza

<400> SEQUENCE: 82
ccacagatca tctccgtgct cag                                          23

<210> SEQ ID NO 83
<211> LENGTH: 23
<212> TYPE: DNA
<213> ORGANISM: Artificial Sequence
<220> FEATURE:
<223> OTHER INFORMATION: Primer based on Oriza

<400> SEQUENCE: 83
ttcttgtact cccccaggt gaa                                           23

<210> SEQ ID NO 84
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 84
aggtgttcga ccgcaaggac g                                            21

<210> SEQ ID NO 85
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 85
gaggaggagc ccccattggt t                                            21

<210> SEQ ID NO 86
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 86
aagatgggga acaagtgggc t                                            21

<210> SEQ ID NO 87
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 87
tagaaacggc tgaaagatgt gg                                           22

<210> SEQ ID NO 88
<211> LENGTH: 21
<212> TYPE: DNA
<213> ORGANISM: Artificial Sequence
<220> FEATURE:
<223> OTHER INFORMATION: Primer based on Oriza
```

```
<400> SEQUENCE: 88
attcaactgg gagtcgtgga a                                              21

<210> SEQ ID NO 89
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 89
tcgaagaggc agtagatgcc g                                              21

<210> SEQ ID NO 90
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 90
aggtaggcaa agggagggta                                                20

<210> SEQ ID NO 91
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 91
ccacgaacaa ctgaagagca                                                20

<210> SEQ ID NO 92
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 92
tccaaatgca aaatgataat gg                                             22

<210> SEQ ID NO 93
<211> LENGTH: 26
<212> TYPE: DNA
<213> ORGANISM: Artificial Sequence
<220> FEATURE:
<223> OTHER INFORMATION: Primer based on Oriza

<400> SEQUENCE: 93
agggaactga gtttgtatgt atgtag                                         26

<210> SEQ ID NO 94
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 94
gttgtgcagc aagtttgagc                                                20

<210> SEQ ID NO 95
<211> LENGTH: 22
<212> TYPE: DNA
```

```
<213> ORGANISM: Artificial Sequence
<220> FEATURE:
<223> OTHER INFORMATION: Primer based on Oriza

<400> SEQUENCE: 95
tcattcagag aggattcact gc                                          22

<210> SEQ ID NO 96
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 96
caaggtggtg gagctgacat                                             20

<210> SEQ ID NO 97
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 97
cgcaaacata tttgattctt cc                                          22

<210> SEQ ID NO 98
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 98
gtctcggtgg tgctcttgtc                                             20

<210> SEQ ID NO 99
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 99
acactaaggg ccttgcagaa                                             20

<210> SEQ ID NO 100
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 100
tcagtttctg actgagggag tg                                          22

<210> SEQ ID NO 101
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 101 aacagtttttt gcagggagga                                            20
```

<210> SEQ ID NO 102
<211> LENGTH: 18
<212> TYPE: DNA
<213> ORGANISM: Artificial Sequence
<220> FEATURE:
<223> OTHER INFORMATION: Primer based on Oriza

<400> SEQUENCE: 102
agctggggaa cctagacg                                                   18

<210> SEQ ID NO 103
<211> LENGTH: 24
<212> TYPE: DNA
<213> ORGANISM: Artificial Sequence
<220> FEATURE:
<223> OTHER INFORMATION: Primer based on Oriza

<400> SEQUENCE: 103
ccctaaaatt tcagtgataa acca                                            24

<210> SEQ ID NO 104
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 104
tgctgatttc ggatacgttg                                                 20

<210> SEQ ID NO 105
<211> LENGTH: 21
<212> TYPE: DNA
<213> ORGANISM: Artificial Sequence
<220> FEATURE:
<223> OTHER INFORMATION: Primer based on Oriza

<400> SEQUENCE: 105
cactgatttc aggacgcttc t                                               21

<210> SEQ ID NO 106
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 106
aactccggac aaggttgttg                                                 20

<210> SEQ ID NO 107
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 107
acagggagtc ctgcatttga                                                 20

<210> SEQ ID NO 108
<211> LENGTH: 24
<212> TYPE: DNA
<213> ORGANISM: Artificial Sequence
<220> FEATURE:
<223> OTHER INFORMATION: Primer based on Oriza -continued

<210> SEQ ID NO 108

```
gtctgatctt cgctggcaag cagc                                            24
```

<210> SEQ ID NO 109
<211> LENGTH: 26
<212> TYPE: DNA
<213> ORGANISM: Artificial Sequence
<220> FEATURE:
<223> OTHER INFORMATION: Primer based on Oriza

<400> SEQUENCE: 109

```
gcatactgct gtcccacagg aaactg                                          26
```

<210> SEQ ID NO 110
<211> LENGTH: 20
<212> TYPE: DNA
<213> ORGANISM: Artificial Sequence
<220> FEATURE:
<223> OTHER INFORMATION: Primer based on Oriza

<400> SEQUENCE: 110

```
tgctgaatgg gctgataaac                                                 20
```

<210> SEQ ID NO 111
<211> LENGTH: 22
<212> TYPE: DNA
<213> ORGANISM: Artificial Sequence
<220> FEATURE:
<223> OTHER INFORMATION: Primer based on Oriza

<400> SEQUENCE: 111

```
atgcagaaaa gacgagatgc ag                                              22
```

<210> SEQ ID NO 112
<211> LENGTH: 184
<212> TYPE: PRT
<213> ORGANISM: Artificial Sequence
<220> FEATURE:
<223> OTHER INFORMATION: An amino acid sequence of qLTG-3-1 based on
      Oriza

<400> SEQUENCE: 112

```
Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly Gly
            35                  40                  45

Gly Gly Gly Arg Gly Gly Gly Gly Ser Gly Gly Gly Ser Gly Gly Gly
        50                  55                  60

Gly Gly Gly Ser Gly Gly Gly Gly Ser Gly Gly Gly Ser Gly Gly Gly
    65                  70                  75                  80

Gly Gly Ser Gly Gly Gly Gly Gly Gly Ser Gly Gly Gly Gly Gly Gly
                85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Pro Arg Gln
        115                 120                 125

Pro Cys Cys Ser Leu Ile Gln Gly Leu Ala Asp Leu Glu Ala Ala Val
    130                 135                 140

Cys Leu Cys Thr Ala Leu Arg Ala Asn Ile Leu Gly Ile Asn Leu Asn
145                 150                 155                 160
```

Leu Pro Ile Asn Leu Ser Leu Leu Val Asn Tyr Cys Gly Arg Ser Val
            165                 170                 175

Pro Ser Gly Phe Gln Cys Ser Asn
            180

<210> SEQ ID NO 113
<211> LENGTH: 555
<212> TYPE: DNA
<213> ORGANISM: Oriza

<400> SEQUENCE: 113

```
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300
ccgatcgaca cgctgaagct gggggtgtgc gcgaacgtgc tgaatgggct gataaacgtg     360
cagctgggga cgccgccgcg gcagccgtgt tgcagcctca tccagggcct cgccgacctt     420
gaggccgccg tgtgcctctg caccgccctc gcgccaaca tccttggcat caacctcaac     480
ctccccatca acctcagcct cctcgtcaac tactgcggcc gctccgtccc ctccggcttc     540
cagtgcagca actaa                                                      555
```

<210> SEQ ID NO 114
<211> LENGTH: 484
<212> TYPE: DNA
<213> ORGANISM: Oriza

<400> SEQUENCE: 114

```
atggcgacga aagctggggt gatcgccacg ctcctggccc tgaaccggtg gcggtggcgg      60
tggcggtggc ggtggtggag ggcgtggagg tggtggcggg agcggcggag gttcaggtgg     120
aggcggcggt tcaggtggag gaggaagcgg cggcggaggt tcaggcggtg gaggaagcgg     180
aggcggcgga ggaggaggaa gcggcggcgg cggggagga ggaagatgcc cgatcgacac      240
gctgaagctg ggggtgtgcg cgaacgtgct gaatgggctg ataaacgtgc agctggggac     300
gccgccgcgg cagccgtgtt gcagcctcat ccagggcctc gccgaccttg aggccgccgt     360
gtgcctctgc accgccctcc gcgccaacat ccttggcatc aacctcaacc tccccatcaa     420
cctcagcctc ctcgtcaact actgcggccg ctccgtcccc tccggcttcc agtgcagcaa     480
ctaa                                                                  484
```

<210> SEQ ID NO 115
<211> LENGTH: 555
<212> TYPE: DNA
<213> ORGANISM: Oriza

<400> SEQUENCE: 115

```
atggcgacga aagctggggt gatcgccacg ctcctggccc tgaacctcca cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300
ccgatcgaca cgctgaagct gggggtgtgc gcgaacgtgc tgaatgggct gataaacgtg     360
```

```
cagctgggga cgccgccgcg gcagccgtgt tgcagcctca tccagggcct cgccgacctt    420
gaggccgccg tgtgcctctg caccgccctc cgcgccaaca tccttggcat caacctcaac    480
ctccccatca acctcagcct cctcgtcaac tactgcggcc gctccgtccc ctccggcttc    540
cagtgcagca actaa                                                     555
```

```
<210> SEQ ID NO 116
<211> LENGTH: 184
<212> TYPE: PRT
<213> ORGANISM: Oriza

<400> SEQUENCE: 116
```

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Gly Gly Gly Gly
        35                  40                  45

Gly Gly Gly Arg Gly Gly Gly Gly Ser Gly Gly Ser Gly Gly
    50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
            85                  90                  95

Gly Gly Arg Cys Pro Ile Asp Thr Leu Lys Leu Gly Val Cys Ala Asn
        100                 105                 110

Val Leu Asn Gly Leu Ile Asn Val Gln Leu Gly Thr Pro Pro Arg Gln
    115                 120                 125

Pro Cys Cys Ser Leu Ile Gln Gly Leu Ala Asp Leu Glu Ala Ala Val
130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

```
<210> SEQ ID NO 117
<211> LENGTH: 116
<212> TYPE: PRT
<213> ORGANISM: Oriza

<400> SEQUENCE: 117
```

Met Ala Thr Lys Ala Gly Val Ile Ala Thr Leu Leu Ala Leu Asn Arg
1               5                   10                  15

Trp Arg Trp Arg Trp Arg Trp Arg Trp Trp Arg Ala Trp Arg Trp Trp
            20                  25                  30

Arg Glu Arg Arg Arg Phe Arg Trp Arg Arg Arg Phe Arg Trp Arg Arg
        35                  40                  45

Lys Arg Arg Arg Phe Arg Arg Trp Arg Lys Arg Arg Arg Arg
    50                  55                  60

Arg Arg Lys Arg Arg Arg Gly Arg Arg Lys Met Pro Asp Arg His
65                  70                  75                  80

Ala Glu Ala Gly Gly Val Arg Glu Arg Ala Glu Trp Ala Asp Lys Arg
            85                  90                  95

Ala Ala Gly Asp Ala Ala Ala Ala Ala Val Leu Gln Pro His Pro Gly

<210> SEQ ID NO 118
<211> LENGTH: 184
<212> TYPE: PRT
<213> ORGANISM: Oriza

<400> SEQUENCE: 118

Met Ala Thr Lys Ala Gly Val Ile Ala Thr Leu Leu Ala Leu Asn Leu
1               5                   10                  15

His Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Gly Gly Gly Gly
        35                  40                  45

Gly Gly Gly Arg Gly Gly Gly Gly Ser Gly Gly Ser Gly Gly
50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
            85                  90                  95

Gly Gly Arg Cys Pro Ile Asp Thr Leu Lys Leu Gly Val Cys Ala Asn
        100                 105                 110

Val Leu Asn Gly Leu Ile Asn Val Gln Leu Gly Thr Pro Pro Arg Gln
    115                 120                 125

Pro Cys Cys Ser Leu Ile Gln Gly Leu Ala Asp Leu Glu Ala Ala Val
130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 119
<211> LENGTH: 18
<212> TYPE: PRT
<213> ORGANISM: Oriza

<400> SEQUENCE: 119

Val Ser Leu Phe Leu Leu Leu Asp Leu Leu Phe Ala Ala Ala Asn
1               5                   10                  15

Ala Cys

<210> SEQ ID NO 120
<211> LENGTH: 25
<212> TYPE: PRT
<213> ORGANISM: Oriza

<400> SEQUENCE: 120

Met Ala Lys Lys Val Ala Val Ala Thr Leu Leu Ala Leu Asn Leu
1               5                   10                  15

Leu Leu Phe Gly Phe Ala Asp Ala Cys
            20                  25

<210> SEQ ID NO 121
<211> LENGTH: 32
<212> TYPE: PRT

<213> ORGANISM: Oriza

<400> SEQUENCE: 121

Met Ala Ser Lys Val Ser Ser Leu Ala Leu Phe Leu Thr Leu Asn
1               5                   10                  15

Ile Leu Phe Phe Thr Leu Val Ser Ser Cys Gly Thr Cys Asp Gln Pro
            20                  25                  30

<210> SEQ ID NO 122
<211> LENGTH: 25
<212> TYPE: PRT
<213> ORGANISM: Oriza

<400> SEQUENCE: 122

Met Ala Arg Lys Ala Ala Val Ile Ala Thr Leu Leu Ala Leu Asn Leu
1               5                   10                  15

Leu Phe Phe Thr Val Ala Asp Gly Cys
            20                  25

<210> SEQ ID NO 123
<211> LENGTH: 25
<212> TYPE: PRT
<213> ORGANISM: Oriza

<400> SEQUENCE: 123

Met Ala Lys Lys Ala Ala Val Ile Ala Thr Leu Leu Ala Leu Asn Leu
1               5                   10                  15

Leu Phe Phe Thr Phe Ala Asp Ala Cys
            20                  25

<210> SEQ ID NO 124
<211> LENGTH: 24
<212> TYPE: PRT
<213> ORGANISM: Oriza

<400> SEQUENCE: 124

Ile Ala Leu Phe Leu Ile Val Asn Ile Leu Phe Phe Ser Leu Val Ser
1               5                   10                  15

Ala Cys Gly Thr Cys Pro Gly Pro
            20

<210> SEQ ID NO 125
<211> LENGTH: 25
<212> TYPE: PRT
<213> ORGANISM: Oriza

<400> SEQUENCE: 125

Met Ala Lys Lys Ala Ala Val Ile Ala Thr Leu Leu Ala Leu Asn Leu
1               5                   10                  15

Leu Phe Phe Thr Phe Ala Asp Ala Cys
            20                  25

<210> SEQ ID NO 126
<211> LENGTH: 25
<212> TYPE: PRT
<213> ORGANISM: Oriza

<400> SEQUENCE: 126

Met Ala Thr Lys Ala Ala Val Ile Ala Thr Leu Leu Ala Leu Asn Leu
1               5                   10                  15

Leu Phe Phe Thr Leu Ala Asp Asp Cys
            20                  25

```
<210> SEQ ID NO 127
<211> LENGTH: 25
<212> TYPE: PRT
<213> ORGANISM: Oriza

<400> SEQUENCE: 127

Met Ala Lys Lys Val Gln Val Ile Ala Thr Leu Leu Ala Leu Asn Leu
1               5                   10                  15

Leu Phe Phe Thr Phe Ala Asn Ala Thr
            20                  25

<210> SEQ ID NO 128
<211> LENGTH: 23
<212> TYPE: PRT
<213> ORGANISM: Oriza

<400> SEQUENCE: 128

Thr Glu Ala Ser Leu Val Thr Leu Phe Leu Ser Phe Asn Leu Leu Phe
1               5                   10                  15

Phe Ala Ile Val Thr Ala Thr
            20

<210> SEQ ID NO 129
<211> LENGTH: 24
<212> TYPE: PRT
<213> ORGANISM: Oriza

<400> SEQUENCE: 129

Leu Ala Leu Phe Leu Thr Leu Asn Ile Leu Phe Phe Ala Leu Val Ser
1               5                   10                  15

Ser Cys Gly Thr Cys Pro Gly Asn
            20

<210> SEQ ID NO 130
<211> LENGTH: 24
<212> TYPE: PRT
<213> ORGANISM: Oriza

<400> SEQUENCE: 130

Ile Ala Leu Phe Phe Cys Leu Asn Leu Leu Phe Phe Ser Leu Val Thr
1               5                   10                  15

Ala Cys Gly Ser Cys Ser His Pro
            20

<210> SEQ ID NO 131
<211> LENGTH: 25
<212> TYPE: PRT
<213> ORGANISM: Oriza

<400> SEQUENCE: 131

Met Ala Lys Lys Ala Ala Ala Ile Ala Thr Leu Leu Ala Leu Asn Leu
1               5                   10                  15

Leu Phe Phe Thr Phe Ser Asp Ala Cys
            20                  25

<210> SEQ ID NO 132
<211> LENGTH: 25
<212> TYPE: PRT
<213> ORGANISM: Oriza

<400> SEQUENCE: 132

Met Ala Lys Lys Val Glu Leu Ile Val Ala Leu Leu Ala Leu Asn Leu
1               5                   10                  15
```

Leu Phe Phe Thr Phe Ser Asp Ala Ser
            20                  25

<210> SEQ ID NO 133
<211> LENGTH: 14
<212> TYPE: PRT
<213> ORGANISM: Oriza

<400> SEQUENCE: 133

Leu Ala Leu Asn Leu Leu Phe Ser Val Thr Ser Ala Cys
1               5                   10

<210> SEQ ID NO 134
<211> LENGTH: 32
<212> TYPE: PRT
<213> ORGANISM: Oriza

<400> SEQUENCE: 134

Met Ala Ser Lys Thr Cys Ser Ser Leu Ala Ile Phe Leu Thr Ile Asn
1               5                   10                  15

Ile Leu Phe Phe Thr Leu Val Ser Ser Cys Gly Thr Cys Gly Ser Gly
            20                  25                  30

<210> SEQ ID NO 135
<211> LENGTH: 18
<212> TYPE: PRT
<213> ORGANISM: Oriza

<400> SEQUENCE: 135

Val Pro Leu Phe Leu Val Leu Asn Leu Leu Phe Ala Ala Ala Asn
1               5                   10                  15

Ala Cys

<210> SEQ ID NO 136
<211> LENGTH: 24
<212> TYPE: PRT
<213> ORGANISM: Oriza

<400> SEQUENCE: 136

Ser Thr Met Ala Lys Lys Val Ala Thr Leu Leu Ala Leu Asn Leu Leu
1               5                   10                  15

Phe Phe Ala Phe Ala Asp Ala Cys
            20

<210> SEQ ID NO 137
<211> LENGTH: 24
<212> TYPE: PRT
<213> ORGANISM: Oriza

<400> SEQUENCE: 137

Met Ala Ser Lys Thr Arg Ala Ser Val Ala Leu Phe Leu Ser Leu Asn
1               5                   10                  15

Leu Leu Phe Leu Val Ile Val Ser
            20

<210> SEQ ID NO 138
<211> LENGTH: 23
<212> TYPE: PRT
<213> ORGANISM: Oriza

<400> SEQUENCE: 138

Thr Lys Ala Ser Leu Leu Ile Leu Phe Leu Ser Leu Asn Leu Leu Phe
1               5                   10                  15

```
Phe Ala Ile Val Thr Ala Thr
            20

<210> SEQ ID NO 139
<211> LENGTH: 18
<212> TYPE: PRT
<213> ORGANISM: Oriza

<400> SEQUENCE: 139

Ile Asn Ile Leu Phe Phe Ala Leu Ala Ser Ala Cys Gly Thr Cys Pro
1               5                   10                  15

Ser Pro

<210> SEQ ID NO 140
<211> LENGTH: 25
<212> TYPE: PRT
<213> ORGANISM: Oriza

<400> SEQUENCE: 140

Met Ala Thr Lys Ala Gly Val Ile Ala Thr Leu Leu Ala Leu Asn Leu
1               5                   10                  15

Leu Phe Phe Thr Phe Ser Asp Ala Cys
            20                  25

<210> SEQ ID NO 141
<211> LENGTH: 17
<212> TYPE: PRT
<213> ORGANISM: Oriza
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid

<400> SEQUENCE: 141

Ala Xaa Xaa Leu Ala Leu Asn Leu Leu Phe Phe Xaa Xaa Xaa Xaa Ala
1               5                   10                  15

Cys

<210> SEQ ID NO 142
<211> LENGTH: 555
<212> TYPE: DNA
<213> ORGANISM: Oriza

<400> SEQUENCE: 142
atggcgacga aagctggggt gatcgccacg ctcctggccc tgaacctcct cttcttcacc    60
ttctccgacg cgtgcggctg ccagtgcggc tcatgcccta gtcccggcgg aggaggcggt   120
ggcggtggcg gtggcggtgg cgtggtggga gggcgtggag gtggtggcgg gagcggcgga   180
ggttcaggtg gaggcggcgg ttcaggtgga ggaggaagcg gcggcggagg ttcaggcggt   240
ggaggaagcg gaggcggcgg aggaggagga agcggcggcg gcggggggagg aggaagatgc   300 ccgatcgaca cgctgaagct gggggtgtgc gcgaacgtgc tgaatgggct gataaacgtg   360
cagctgggga cgccgccgcg gcagccgtgt tgcagcctca tccagggcct cgccgaccta   420
gaggccgccg tgtgcctctg caccgccctc cgcgccaaca tccttggcat caacctcaac   480
ctccccatca acctcagcct cctcgtcaac tactgcggcc gctccgtccc ctccggcttc   540
cagtgcagca actaa                                                    555
```

<210> SEQ ID NO 143
<211> LENGTH: 555
<212> TYPE: DNA
<213> ORGANISM: Oriza

<400> SEQUENCE: 143

```
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300
ccgatcgaca cgctgaagct ggggggtgtgc gcgaacgtgc tgaatgggct gataaacgtg     360
cagctgggga cgccgccgcg gcagccgtgt tgcagcctca tccagggcct cgccgacctt     420
gaggccgccg tgtgcctctg caccgccctc cgcgccaaca tccttggcat caacctcaac     480
ctccccatca acctcagcct cctcgtcaac tactgcggcc gctccgtccc ctccggcttc     540
cagtgcagca actaa                                                      555
```

<210> SEQ ID NO 144
<211> LENGTH: 555
<212> TYPE: DNA
<213> ORGANISM: Oriza

<400> SEQUENCE: 144

```
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300
ccgatcgaca cgctgaagct gggggtgtgc gcgaacgtgc tgaatgggct gataaacgtg     360
cagctgggga cgccgccgcg gcagccgtgt tgcagcctca tccagggcct cgccgacctt     420
gaggccgccg tgtgcctctg caccgccctc cgcgccaaca tccttggcat caacctcaac     480
ctccccatca acctcagcct cctcgtcaac tactgcggcc gctccgtccc ctccggcttc     540
cagtgcagca actaa                                                      555
```

<210> SEQ ID NO 145
<211> LENGTH: 555
<212> TYPE: DNA
<213> ORGANISM: Oriza

<400> SEQUENCE: 145

```
atggcgacga aagctggggt gatcgccacg ctcctggccc tgaacctcct cttcttcacc      60
ttctccgacg cgtgcggctg ccagtgcggc tcatgcccta gtcccggcgg aggaggcggt     120
ggcggtggcg gtggcggtgg cggtggtgga gggcgtggag gtggtggcgg gagcggcgga     180
ggttcaggtg gaggcggcgg ttcaggtgga ggaggaagcg gcggcggagg ttcaggcggt     240
ggaggaagcg gaggcggcgg aggaggagga agcggcggcg gcggggagg aggaagatgc      300
ccgatcgaca cgctgaagct gggggtgtgc gcgaacgtgc tgaatgggct gataaacgtg     360
cagctgggga cgccgccgcg gcagccgtgt tgcagcctca tccagggcct cgccgacctt     420
gaggccgccg tgtgcctctg caccgccctc cgcgccaaca tccttggcat caacctcaac     480
```

| | |
|---|---|
| ctccccatca acctcagcct cctcgtcaac tactgcggcc gctccgtccc ctccggcttc | 540 |
| cagtgcagca actaa | 555 |

<210> SEQ ID NO 146
<211> LENGTH: 555
<212> TYPE: DNA
<213> ORGANISM: Oriza

<400> SEQUENCE: 146

| | |
|---|---|
| atggcgacga aagctggggt gatcgccacg ctcctggccc tgaacctcct cttcttcacc | 60 |
| ttctccgacg cgtgcggctg ccagtgcggc tcatgcccta gtcccggcgg aggaggcggt | 120 |
| ggcggtggcg gtggcggtgg cggtggtgga gggcgtggag gtggtggcgg gagcggcgga | 180 |
| ggttcaggtg gaggcggcgg ttcaggtgga ggaggaagcg gcggcggagg ttcaggcggt | 240 |
| ggaggaagcg gaggcggcgg aggaggagga agcggcggcg gcggggagg aggaagatgc | 300 |
| ccgatcgaca cgctgaagct gggggtgtgc gcgaacgtgc tgaatgggct gataaacgtg | 360 |
| cagctgggga cgccgccgcg gcagccgtgt tgcagcctca tccagggcct cgccgacctt | 420 |
| gaggccgccg tgtgcctctg caccgccctc cgcgccaaca tccttggcat caacctcaac | 480 |
| ctccccatca acctcagcct cctcgtcaac tactgcggcc gctccgtccc ctccggcttc | 540 |
| cagtgcagca actaa | 555 |

<210> SEQ ID NO 147
<211> LENGTH: 555
<212> TYPE: DNA
<213> ORGANISM: Oriza

<400> SEQUENCE: 147

| | |
|---|---|
| atggcgacga aagctggggt gatcgccacg ctcctggccc tgaacctcca cttcttcacc | 60 |
| ttctccgacg cgtgcggctg ccagtgcggc tcatgcccta gtcccggcgg aggaggcggt | 120 |
| ggcggtggcg gtggcggtgg cggtggtgga gggcgtggag gtggtggcgg gagcggcgga | 180 |
| ggttcaggtg gaggcggcgg ttcaggtgga ggaggaagcg gcggcggagg ttcaggcggt | 240 |
| ggaggaagcg gaggcggcgg aggaggagga agcggcggcg gcggggagg aggaagatgc | 300 |
| ccgatcgaca cgctgaagct gggggtgtgc gcgaacgtgc tgaatgggct gataaacgtg | 360 |
| cagctgggga cgccgccgcg gcagccgtgt tgcagcctca tccagggcct cgccgacctt | 420 |
| gaggccgccg tgtgcctctg caccgccctc cgcgccaaca tccttggcat caacctcaac | 480 |
| ctccccatca acctcagcct cctcgtcaac tactgcggcc gctccgtccc ctccggcttc | 540 |
| cagtgcagca actaa | 555 |

<210> SEQ ID NO 148
<211> LENGTH: 537
<212> TYPE: DNA
<213> ORGANISM: Oriza

<400> SEQUENCE: 148

| | |
|---|---|
| atggcgacga aagctggggt gatcgccacg ctcctggccc tgaacctcct cttcttcacc | 60 |
| ttctccgacg cgtgcggctg ccagtgcggc tcatgcccta gtcccggcgg aggaggcggt | 120 |
| ggcggtggtg gagggcgtgg aggtggtggc gggagcggcg gaggcggagg tggaggcggc | 180 |
| ggttcaggtg gaggaggaag cggcggcgga ggttcaggcg gtggaggaag cggaggcggc | 240 |
| ggaggaggag gaagcggcgg cggcggggga ggaggaagat gccgatcga cacgctgaag | 300 |
| ctgggggtgt gcgcgaacgt gctgaatggg ctgataaacg tgcagctggg gacgccgccg | 360 |

```
cggcagccgt gttgcagcct catccagggc ctcgccgacc ttgaggccgc cgtgtgcctc    420
tgcaccgccc tccgcgccaa catccttggc atcaacctca acctccccat caacctcagc    480
ctcctcgtca actactgcgg ccgctccgtc ccctccggct tccagtgcag caactaa       537

<210> SEQ ID NO 149
<211> LENGTH: 537
<212> TYPE: DNA
<213> ORGANISM: Oriza

<400> SEQUENCE: 149
atggcgacga aagctggggt gatcgccacg ctcctggccc tgaacctcct cttcttcacc     60
ttctccgacg cgtgcggctg ccagtgcggc tcatgcccta gtcccggcgg aggaggcggt    120
ggcggtggtg gagggcgtgg aggtggtggc gggagcggcg gaggcggagg tggaggcggc    180
ggttcaggtg gaggaggaag cggcggcgga ggttcaggcg gtggaggaag cggaggcggc    240
ggaggaggag gaagcggcgg cggcggggga ggaggaagat gcccgatcga cacgctgaag    300
ctgggggtgt gcgcgaacgt gctgaatggg ctgataaacg tgcagctggg gacgccgccg    360
cggcagccgt gttgcagcct catccagggc ctcgccgacc ttgaggccgc cgtgtgcctc    420
tgcaccgccc tccgcgccaa catccttggc atcaacctca acctccccat caacctcagc    480
ctcctcgtca actactgcgg ccgctccgtc ccctccggct tccagtgcag caactaa       537

<210> SEQ ID NO 150
<211> LENGTH: 537
<212> TYPE: DNA
<213> ORGANISM: Oriza

<400> SEQUENCE: 150
atggcgacga aagctggggt gatcgccacg ctcctggccc tgaacctcct cttcttcacc     60
ttctccgacg cgtgcggctg ccagtgcggc tcatgcccta gtcccggcgg aggaggcggt    120
ggcggtggtg gagggcgtgg aggtggtggc gggagcggcg gaggcggagg tggaggcggc    180
ggttcaggtg gaggaggaag cggcggcgga ggttcaggcg gtggaggaag cggaggcggc    240
ggaggaggag gaagcggcgg cggcggggga ggaggaagat gcccgatcga cacgctgaag    300
ctgggggtgt gcgcgaacgt gctgaatggg ctgataaacg tgcagctggg gacgccgccg    360
cggcagccgt gttgcagcct catccagggc ctcgccgacc ttgaggccgc cgtgtgcctc    420
tgcaccgccc tccgcgccaa catccttggc atcaacctca acctccccat caacctcagc    480
ctcctcgtca actactgcgg ccgctccgtc ccctccggct tccagtgcag caactaa       537

<210> SEQ ID NO 151
<211> LENGTH: 573
<212> TYPE: DNA
<213> ORGANISM: Oriza

<400> SEQUENCE: 151
atggcgacga aagctggggt gatcgccacg ctcctggccc tgaacctcct cttcttcacc     60
ttctccgacg cgtgcggctg ccagtgcggc tcatgcccta gtcccggcgg aggaggcggt    120
ggcggtggtg gagggcgtgg aggtggtggc gggagcggcg gaggttcagg tggggttca    180 ggtggtggag gaagcggagg cggaggtgga ggcggcggtt caggtggagg aggaagcggc    240
ggcggaggtt caggcggtgg aggaagcgga ggcggcggag gaggaagcgg cggcggcggc    300
gggggaggag gaagatgccc gatcgacacg ctgaagctgg gggtgtgcgc gaacgtgctg    360
aatgggctga taaacgtgca gctggggacg ccgccgcggc agccgtgttg cagcctcatc    420
```

```
cagggcctcg ccgaccttga ggccgccgtg tgcctctgca ccgccctccg cgccaacatc    480
cttggcatca acctcaacct ccccatcaac ctcagcctcc tcgtcaacta ctgcggccgc    540
tccgtcccct ccggcttcca gtgcagcaac taa                                 573
```

<210> SEQ ID NO 152
<211> LENGTH: 537
<212> TYPE: DNA
<213> ORGANISM: Oriza

<400> SEQUENCE: 152

```
atggcgacga aagctggggt gatcgccacg ctcctggccc tgaacctcct cttcttcacc     60
ttctccgacg cgtgcggctg ccagtgcggc tcatgcccta gtcccggcgg aggaggcggt    120
ggcggtggtg agggcgtgg aagtggtggc gggagcggcg gaggcggagg tggaggcggc    180
ggttcaggtg gaggaggaag cggcggcgga ggttcaggcg gtggaggaag cggaggcggc    240
ggaggaggag gaagcggcgg cggcggggga ggaggaagat gcccgatcga cacgctgaag    300
ctgggggtgt gcgcgaacgt gctgaatggg ctgataaacg tgcagctggg gacgccgccg    360
cggcagccgt gttgcagcct catccagggc ctcgccgacc ttgaggccgc cgtgtgcctc    420
tgcaccgccc tccgcgccaa catccttggc atcaacctca acctccccat caacctcagc    480
ctcctcgtca actactgcgg ccgctccgtc cctccggct tccagtgcag caactaa       537
```

<210> SEQ ID NO 153
<211> LENGTH: 585
<212> TYPE: DNA
<213> ORGANISM: Oriza

<400> SEQUENCE: 153

```
atggcgacga aagctggggt gatcgccacg ctcctggccc tgaacctcct cttcttcacc     60
ttctccgacg cgtgcggctg ccagtgcggc tcatgcccta gtcccggcgg aggaggcggt    120
ggcggtggcg gtggcggtgg tggagggcgt ggaggtggtg gcgggagcgg cggaggttca    180
ggtgggggtt caggtggtgg aggaagcgga ggcggaggtg gaggcggcgg ttcaggtgga    240
ggaggaagcg gcggcggagg ttcaggcggt ggaggaagcg gaggcggcgg aggaggagga    300
agcggcggcg gcggggagg aggaagatgc ccgatcgaca cgctgaagct gggggtgtgc    360
gcgaacgtgc tgaatgggct gataaacgtg cagctgggga cgccgccgcg gcagccgtgt    420
tgcagcctca tccagggcct cgccgacctt gaggccgccg tgtgcctctg caccgccctc    480
cgcgccaaca tccttggcat caacctcaac ctccccatca acctcagcct cctcgtcaac    540
tactgcggcc gctccgtccc ctccggcttc agtgcagca actaa                    585
```

<210> SEQ ID NO 154
<211> LENGTH: 597
<212> TYPE: DNA
<213> ORGANISM: Oriza

<400> SEQUENCE: 154

```
atggcgacga aagctggggt gatcgccacg ctcctggccc tgaacctcct cttcttcacc     60
ttctccgacg cgtgcggctg ccagtgcggc tcatgcccta gtcccggcgg aggaggcggt    120
ggcggtggcg gtggcggtgg tggagggcgt ggaggtggtg gcgggagcgg cggaggttca    180
ggtgggggtt caggtggtgg aggaagcgga ggcggaggtt caggcggagg tggaggcggc    240
ggttcaggtg gaggaggaag cggcggcgga ggttcaggcg gtggaggaag cggaggcggc    300
ggaggaggag gaagcggcgg cggcggggga ggaggaagat gcccgatcga cacgctgaag    360
```

```
ctgggggtgt gcgcgaacgt gctgaatggg ctgataaacg tgcagctggg gacgccgccg    420
cggcagccgt gttgcagcct catccagggc ctcgccgacc ttgaggccgc cgtgtgcctc    480
tgcaccgccc tccgcgccaa catccttggc atcaacctca acctccccat caacctcagc    540
ctcctcgtca actactgcgg ccgctccgtc cctccggct tccagtgcag caactaa       597
```

<210> SEQ ID NO 155
<211> LENGTH: 585
<212> TYPE: DNA
<213> ORGANISM: Oriza

<400> SEQUENCE: 155

```
atggcgacga aagctggggt gatcgccacg ctcctggccc tgaacctcct cttcttcacc    60
ttctccgacg cgtgcggctg ccagtgcggc tcatgcccta gtcccggcgg aggaggcggt    120
ggcggtggtg gagggcgtgg aggaggtggc gggagcggcg gaggttcagg tgggggttca    180
ggtggtggac gaagcggagg cggaggttca ggcggaggtg gaggcggcgg ttcaggtgga    240
ggaggaagcg gcggcggagg ttcaggcggt ggaggaagcg gaggcggcgg aggaggagga    300
agcggcggcg gcggggagg aggaagatgc ccgatcgaca cgctgaagct ggggtgtgc     360 gcgaacgtgc tgaatgggct gataaacgtg cagctgggga cgccgccgcg gcagccgtgt    420
tgcagcctca tccagggcct cgccgacctt gaggccgccg tgtgcctctg caccgccctc    480
cgcgccaaca tccttggcat caacctcaac ctccccatca acctcagcct cctcgtcaac    540
tactgcggcc gctccgtccc ctccggcttc cagtgcagca actaa                  585
```

<210> SEQ ID NO 156
<211> LENGTH: 585
<212> TYPE: DNA
<213> ORGANISM: Oriza

<400> SEQUENCE: 156

```
atggcgacga aagctggggt gatcgccacg ctcctggccc tgaacctcct cttcttcacc    60
ttctccgacg cctgcggctg ccagtgcggc tcatgcccta gtcccggcgg aggaggcgga    120
ggcggaggcg gaggcggtgg cggtggcggt ggcggagggc gtggaggtgg tggcgggagc    180
ggcggaggtt caggtggggg ttctggcggt ggtggaggaa gcggcggagg ttcaggtgga    240
ggatcaggtg gtggaggaag cggaggcgga ggttcaggcg gtggaagcgg cggcggcggg    300
tcaggtggcg gcggaggcgg aggaagatgc ccgatcgaca cgctgaagct ggggtgtgc     360 gcgaacgtgc tgaacgggct gataaacgtg cagctgggga cgccgccgcg gcagccgtgc    420
tgcagcctca tccaggggct cgccgacctt gaggccgccg tgtgcctctg caccgccctc    480
cgcgccaaca tccttggcat caacctcaac ctccccatca acctcagcct cctcgtcaac    540
tactgcggcc gctctgtccc ttccggcttc cagtgcagca actag                  585
```

<210> SEQ ID NO 157
<211> LENGTH: 615
<212> TYPE: DNA
<213> ORGANISM: Oriza

<400> SEQUENCE: 157

```
atggcgacga aagctggggt gatcgccacg ctcctggccc tgaacctcct cttcttcacc    60
ttctccgacg cctgcggctg ccagtgcggc tcatgcccta gtcccggcgg aggaggcggt    120
ggcggtggcg gagggcgtgg gggtggtggt gggagcggcg gaggttcagg tggtggagga    180
agcggcggag gttcaggtgg aggatcaggt ggtggaggaa gcggcggagg ttcaggtgga    240
```

```
ggatcaggtg gtggaggaag cggaggcgga ggttcaggcg gtggaagcgg aggcggtgga    300
ggaagcggcg gaggaggagg aagcggcggc ggcggggggag gaggaagcgg aggaagatgc   360
ccgatcgaca cgctgaagct gggggtgtgc gcgaacgtgc tgaatgggct gataaacgtg    420
cagctgggga cgccgccgcg gcagccgtgc tgcagcctca tccagggggct cgccgacctt   480 gaggccgccg tgtgcctctg caccgccctc cgcgccaaca tccttggcat caacctcaac    540
ctccccatca acctcagcct cctcgtcaac tactgcggcc gctctgtccc ttccggcttc    600
cagtgcagca actag                                                     615

<210> SEQ ID NO 158
<211> LENGTH: 184
<212> TYPE: PRT
<213> ORGANISM: Oriza

<400> SEQUENCE: 158

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly Gly
            35                  40                  45

Gly Gly Gly Arg Gly Gly Gly Gly Ser Gly Gly Ser Gly Gly
    50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
                85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Pro Arg Gln
        115                 120                 125

Pro Cys Cys Ser Leu Ile Gln Gly Leu Ala Asp Leu Glu Ala Ala Val
    130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 159
<211> LENGTH: 184
<212> TYPE: PRT
<213> ORGANISM: Oriza

<400> SEQUENCE: 159

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly
            35                  40                  45

Gly Gly Gly Arg Gly Gly Gly Gly Ser Gly Gly Ser Gly Gly
    50                  55                  60

Gly Gly Gly Ser Gly Gly Gly Gly Ser Gly Gly Gly Ser Gly Gly
65                  70                  75                  80
```

```
Gly Gly Ser Gly Gly Gly Gly Gly Ser Gly Gly Gly Gly
            85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Pro Arg Gln
            115                 120                 125

Pro Cys Cys Ser Leu Ile Gln Gly Leu Ala Asp Leu Glu Ala Ala Val
130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Val Asn Tyr Cys Gly Arg Ser Val
            165                 170                 175

Pro Ser Gly Phe Gln Cys Ser Asn
            180

<210> SEQ ID NO 160
<211> LENGTH: 184
<212> TYPE: PRT
<213> ORGANISM: Oriza

<400> SEQUENCE: 160

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30

Pro Ser Pro Gly Gly Gly Gly Gly Gly Gly Gly Gly Gly Gly Gly
            35                  40                  45

Gly Gly Gly Arg Gly Gly Gly Gly Ser Gly Gly Ser Gly Gly
50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
            85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Pro Arg Gln
            115                 120                 125

Pro Cys Cys Ser Leu Ile Gln Gly Leu Ala Asp Leu Glu Ala Ala Val
130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Val Asn Tyr Cys Gly Arg Ser Val
            165                 170                 175

Pro Ser Gly Phe Gln Cys Ser Asn
            180

<210> SEQ ID NO 161
<211> LENGTH: 184
<212> TYPE: PRT
<213> ORGANISM: Oriza

<400> SEQUENCE: 161

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
            20                  25                  30
```

```
Pro Ser Pro Gly Gly Gly Gly Gly Gly Gly Gly Gly Gly
        35                  40                  45

Gly Gly Gly Arg Gly Gly Gly Gly Ser Gly Gly Ser Gly Gly
 50                  55                  60

Gly Gly Gly Ser Gly Gly Gly Ser Gly Gly Gly Ser Gly Gly
 65                  70                  75                  80

Gly Gly Ser Gly Gly Gly Gly Gly Ser Gly Gly Gly Gly
             85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Pro Arg Gln
            115                 120                 125

Pro Cys Cys Ser Leu Ile Gln Gly Leu Ala Asp Leu Glu Ala Ala Val
            130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 162
<211> LENGTH: 184
<212> TYPE: PRT
<213> ORGANISM: Oriza

<400> SEQUENCE: 162

Met Ala Thr Lys Ala Gly Val Ile Ala Thr Leu Leu Ala Leu Asn Leu
1               5                   10                  15

Leu Phe Phe Thr Phe Ser Asp Ala Cys Gly Gln Cys Gly Ser Cys
            20                  25                  30

Pro Ser Pro Gly Gly Gly Gly Gly Gly Gly Gly Gly Gly
        35                  40                  45

Gly Gly Gly Arg Gly Gly Gly Gly Ser Gly Gly Ser Gly Gly
 50                  55                  60

Gly Gly Gly Ser Gly Gly Gly Ser Gly Gly Gly Ser Gly Gly
 65                  70                  75                  80

Gly Gly Ser Gly Gly Gly Gly Gly Ser Gly Gly Gly Gly
             85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Pro Arg Gln
            115                 120                 125

Pro Cys Cys Ser Leu Ile Gln Gly Leu Ala Asp Leu Glu Ala Ala Val
            130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180

<210> SEQ ID NO 163
<211> LENGTH: 184
<212> TYPE: PRT
<213> ORGANISM: Oriza
```

<400> SEQUENCE: 163

```
Met Ala Thr Lys Ala Gly Val Ile Ala Thr Leu Leu Ala Leu Asn Leu
1               5                   10                  15

His Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly Gly
            35                  40                  45

Gly Gly Gly Arg Gly Gly Gly Gly Ser Gly Gly Ser Gly Gly
50                  55                  60

Gly Gly Gly Ser Gly Gly Gly Ser Gly Gly Gly Ser Gly Gly
65                  70                  75                  80

Gly Gly Ser Gly Gly Gly Gly Gly Ser Gly Gly Gly Gly
            85                  90                  95

Gly Gly Arg Cys Pro Ile Asp Thr Leu Lys Leu Gly Val Cys Ala Asn
            100                 105                 110

Val Leu Asn Gly Leu Ile Asn Val Gln Leu Gly Thr Pro Pro Arg Gln
            115                 120                 125

Pro Cys Cys Ser Leu Ile Gln Gly Leu Ala Asp Leu Glu Ala Ala Val
            130                 135                 140

Cys Leu Cys Thr Ala Leu Arg Ala Asn Ile Leu Gly Ile Asn Leu Asn
145                 150                 155                 160

Leu Pro Ile Asn Leu Ser Leu Leu Val Asn Tyr Cys Gly Arg Ser Val
                165                 170                 175

Pro Ser Gly Phe Gln Cys Ser Asn
            180
```

<210> SEQ ID NO 164
<211> LENGTH: 178
<212> TYPE: PRT
<213> ORGANISM: Oriza

<400> SEQUENCE: 164

```
Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Arg Gly Gly
            35                  40                  45

Gly Gly Gly Ser Gly Gly Gly Gly Gly Gly Ser Gly Gly
50                  55                  60

Gly Gly Ser Gly Gly Gly Ser Gly Gly Gly Ser Gly Gly Gly
65                  70                  75                  80

Gly Gly Gly Gly Ser Gly Gly Gly Gly Gly Arg Cys Pro Ile
                85                  90                  95

Asp Thr Leu Lys Leu Gly Val Cys Ala Asn Val Leu Asn Gly Leu Ile
            100                 105                 110

Asn Val Gln Leu Gly Thr Pro Pro Arg Gln Pro Cys Cys Ser Leu Ile
            115                 120                 125

Gln Gly Leu Ala Asp Leu Glu Ala Ala Val Cys Leu Cys Thr Ala Leu
            130                 135                 140

Arg Ala Asn Ile Leu Gly Ile Asn Leu Asn Leu Pro Ile Asn Leu Ser
145                 150                 155                 160

Leu Leu Val Asn Tyr Cys Gly Arg Ser Val Pro Ser Gly Phe Gln Cys
                165                 170                 175

Ser Asn
```

<210> SEQ ID NO 165
<211> LENGTH: 178
<212> TYPE: PRT
<213> ORGANISM: Oriza

<400> SEQUENCE: 165

```
Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Arg Gly Gly
            35                  40                  45

Gly Gly Gly Ser Gly Gly Gly Gly Gly Gly Gly Ser Gly Gly
    50                  55                  60

Gly Gly Ser Gly Gly Gly Ser Gly Gly Gly Ser Gly Gly Gly
65                  70                  75                  80

Gly Gly Gly Gly Ser Gly Gly Gly Gly Gly Arg Cys Pro Ile
                85                  90                  95

Asp Thr Leu Lys Leu Gly Val Cys Ala Asn Val Leu Asn Gly Leu Ile
                100                 105                 110

Asn Val Gln Leu Gly Thr Pro Pro Arg Gln Pro Cys Cys Ser Leu Ile
                115                 120                 125

Gln Gly Leu Ala Asp Leu Glu Ala Ala Val Cys Leu Cys Thr Ala Leu
            130                 135                 140

Arg Ala Asn Ile Leu Gly Ile Asn Leu Asn Leu Pro Ile Asn Leu Ser
145                 150                 155                 160

Leu Leu Val Asn Tyr Cys Gly Arg Ser Val Pro Ser Gly Phe Gln Cys
                165                 170                 175

Ser Asn
```

<210> SEQ ID NO 166
<211> LENGTH: 178
<212> TYPE: PRT
<213> ORGANISM: Oriza

<400> SEQUENCE: 166

```
Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Arg Gly Gly
            35                  40                  45

Gly Gly Gly Ser Gly Gly Gly Gly Gly Gly Gly Ser Gly Gly
    50                  55                  60

Gly Gly Ser Gly Gly Gly Ser Gly Gly Gly Ser Gly Gly Gly
65                  70                  75                  80

Gly Gly Gly Gly Ser Gly Gly Gly Gly Gly Arg Cys Pro Ile
                85                  90                  95

Asp Thr Leu Lys Leu Gly Val Cys Ala Asn Val Leu Asn Gly Leu Ile
                100                 105                 110

Asn Val Gln Leu Gly Thr Pro Pro Arg Gln Pro Cys Cys Ser Leu Ile
                115                 120                 125

Gln Gly Leu Ala Asp Leu Glu Ala Ala Val Cys Leu Cys Thr Ala Leu
            130                 135                 140

Arg Ala Asn Ile Leu Gly Ile Asn Leu Asn Leu Pro Ile Asn Leu Ser
```

```
                145                 150                 155                 160
Leu Leu Val Asn Tyr Cys Gly Arg Ser Val Pro Ser Gly Phe Gln Cys
                165                 170                 175
Ser Asn

<210> SEQ ID NO 167
<211> LENGTH: 190
<212> TYPE: PRT
<213> ORGANISM: Oriza

<400> SEQUENCE: 167

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Arg Gly Gly
            35                  40                  45

Gly Gly Gly Ser Gly Gly Ser Gly Gly Ser Gly Gly Gly
    50                  55                  60

Ser Gly Gly Gly Gly Gly Gly Ser Gly Gly Gly Ser Gly
65                  70                  75                  80

Gly Gly Ser Gly Gly Gly Ser Gly Gly Gly Gly Gly
                85                  90                  95

Ser Gly Gly Gly Gly Gly Gly Arg Cys Pro Ile Asp Thr Leu Lys
                100                 105                 110

Leu Gly Val Cys Ala Asn Val Leu Asn Gly Leu Ile Asn Val Gln Leu
            115                 120                 125

Gly Thr Pro Pro Arg Gln Pro Cys Cys Ser Leu Ile Gln Gly Leu Ala
130                 135                 140

Asp Leu Glu Ala Ala Val Cys Leu Cys Thr Ala Leu Arg Ala Asn Ile
145                 150                 155                 160

Leu Gly Ile Asn Leu Asn Leu Pro Ile Asn Leu Ser Leu Leu Val Asn
                165                 170                 175

Tyr Cys Gly Arg Ser Val Pro Ser Gly Phe Gln Cys Ser Asn
                180                 185                 190

<210> SEQ ID NO 168
<211> LENGTH: 178
<212> TYPE: PRT
<213> ORGANISM: Oriza

<400> SEQUENCE: 168

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Arg Gly Gly
            35                  40                  45

Gly Gly Gly Ser Gly Gly Gly Gly Gly Gly Gly Ser Gly Gly
    50                  55                  60

Gly Gly Ser Gly Gly Gly Ser Gly Gly Gly Ser Gly Gly
65                  70                  75                  80

Gly Gly Gly Ser Gly Gly Gly Gly Gly Arg Cys Pro Ile
                85                  90                  95

Asp Thr Leu Lys Leu Gly Val Cys Ala Asn Val Leu Asn Gly Leu Ile
            100                 105                 110
```

Asn Val Gln Leu Gly Thr Pro Pro Arg Gln Pro Cys Cys Ser Leu Ile
            115                 120                 125

Gln Gly Leu Ala Asp Leu Glu Ala Ala Val Cys Leu Cys Thr Ala Leu
    130                 135                 140

Arg Ala Asn Ile Leu Gly Ile Asn Leu Asn Leu Pro Ile Asn Leu Ser
145                 150                 155                 160

Leu Leu Val Asn Tyr Cys Gly Arg Ser Val Pro Ser Gly Phe Gln Cys
                165                 170                 175

Ser Asn

<210> SEQ ID NO 169
<211> LENGTH: 194
<212> TYPE: PRT
<213> ORGANISM: Oriza

<400> SEQUENCE: 169

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly Gly
            35                  40                  45

Gly Arg Gly Gly Gly Gly Ser Gly Gly Ser Gly Gly Gly Ser
    50                  55                  60

Gly Gly Gly Gly Ser Gly Gly Gly Gly Gly Gly Ser Gly Gly
65                  70                  75                  80

Gly Gly Ser Gly Gly Gly Ser Gly Gly Gly Ser Gly Gly Gly
                85                  90                  95

Gly Gly Gly Gly Ser Gly Gly Gly Gly Gly Arg Cys Pro Ile
                100                 105                 110

Asp Thr Leu Lys Leu Gly Val Cys Ala Asn Val Leu Asn Gly Leu Ile
            115                 120                 125

Asn Val Gln Leu Gly Thr Pro Pro Arg Gln Pro Cys Cys Ser Leu Ile
            130                 135                 140

Gln Gly Leu Ala Asp Leu Glu Ala Ala Val Cys Leu Cys Thr Ala Leu
145                 150                 155                 160

Arg Ala Asn Ile Leu Gly Ile Asn Leu Asn Leu Pro Ile Asn Leu Ser
                165                 170                 175

Leu Leu Val Asn Tyr Cys Gly Arg Ser Val Pro Ser Gly Phe Gln Cys
                180                 185                 190

Ser Asn

<210> SEQ ID NO 170
<211> LENGTH: 198
<212> TYPE: PRT
<213> ORGANISM: Oriza

<400> SEQUENCE: 170

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly Gly
            35                  40                  45

Gly Arg Gly Gly Gly Gly Ser Gly Gly Gly Ser Gly Gly Gly Ser
    50                  55                  60

Gly Gly Gly Gly Ser Gly Gly Gly Ser Gly Gly Gly Gly
65              70              75              80

Gly Ser Gly Gly Gly Ser Gly Gly Gly Ser Gly Gly Gly
            85              90              95

Ser Gly Gly Gly Gly Gly Ser Gly Gly Gly Gly Gly Gly
        100             105             110

Arg Cys Pro Ile Asp Thr Leu Lys Leu Gly Val Cys Ala Asn Val Leu
            115             120             125

Asn Gly Leu Ile Asn Val Gln Leu Gly Thr Pro Pro Arg Gln Pro Cys
    130             135             140

Cys Ser Leu Ile Gln Gly Leu Ala Asp Leu Glu Ala Ala Val Cys Leu
145             150             155             160

Cys Thr Ala Leu Arg Ala Asn Ile Leu Gly Ile Asn Leu Asn Leu Pro
                165             170             175

Ile Asn Leu Ser Leu Leu Val Asn Tyr Cys Gly Arg Ser Val Pro Ser
                180             185             190

Gly Phe Gln Cys Ser Asn
            195

<210> SEQ ID NO 171
<211> LENGTH: 194
<212> TYPE: PRT
<213> ORGANISM: Oriza

<400> SEQUENCE: 171

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Arg Gly Gly
            35              40              45

Gly Gly Gly Ser Gly Gly Gly Ser Gly Gly Gly Ser Gly Gly Gly Arg
    50              55              60

Ser Gly Gly Gly Gly Ser Gly Gly Gly Gly Gly Gly Ser Gly Gly
65              70              75              80

Gly Gly Ser Gly Gly Gly Ser Gly Gly Gly Ser Gly Gly Gly
            85              90              95

Gly Gly Gly Gly Ser Gly Gly Gly Gly Gly Gly Arg Cys Pro Ile
            100             105             110

Asp Thr Leu Lys Leu Gly Val Cys Ala Asn Val Leu Asn Gly Leu Ile
            115             120             125

Asn Val Gln Leu Gly Thr Pro Pro Arg Gln Pro Cys Cys Ser Leu Ile
    130             135             140

Gln Gly Leu Ala Asp Leu Glu Ala Ala Val Cys Leu Cys Thr Ala Leu
145             150             155             160

Arg Ala Asn Ile Leu Gly Ile Asn Leu Asn Leu Pro Ile Asn Leu Ser
                165             170             175

Leu Leu Val Asn Tyr Cys Gly Arg Ser Val Pro Ser Gly Phe Gln Cys
                180             185             190

Ser Asn

<210> SEQ ID NO 172
<211> LENGTH: 194
<212> TYPE: PRT
<213> ORGANISM: Oriza

<400> SEQUENCE: 172

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Gly Gly Gly Gly
            35                  40                  45

Gly Gly Gly Gly Arg Gly Gly Gly Gly Ser Gly Gly Gly Ser
50                  55                  60

Gly Gly Gly Ser Gly Gly Gly Gly Ser Gly Gly Ser Gly Gly
65                  70                  75                  80

Gly Ser Gly Gly Gly Ser Gly Gly Gly Ser Gly Gly Ser
                85                  90                  95

Gly Gly Gly Gly Ser Gly Gly Gly Gly Gly Arg Cys Pro Ile
                100                 105                 110

Asp Thr Leu Lys Leu Gly Val Cys Ala Asn Val Leu Asn Gly Leu Ile
            115                 120                 125

Asn Val Gln Leu Gly Thr Pro Pro Arg Gln Pro Cys Cys Ser Leu Ile
            130                 135                 140

Gln Gly Leu Ala Asp Leu Glu Ala Ala Val Cys Leu Cys Thr Ala Leu
145                 150                 155                 160

Arg Ala Asn Ile Leu Gly Ile Asn Leu Asn Leu Pro Ile Asn Leu Ser
                165                 170                 175

Leu Leu Val Asn Tyr Cys Gly Arg Ser Val Pro Ser Gly Phe Gln Cys
                180                 185                 190

Ser Asn

<210> SEQ ID NO 173
<211> LENGTH: 204
<212> TYPE: PRT
<213> ORGANISM: Oriza

<400> SEQUENCE: 173

Met Ala Thr Lys Ala Gly Val Ile Ala Thr Leu Leu Ala Leu Asn Leu
1               5                   10                  15

Leu Phe Phe Thr Phe Ser Asp Ala Cys Gly Cys Gln Cys Gly Ser Cys
                20                  25                  30

Pro Ser Pro Gly Gly Gly Gly Gly Gly Gly Gly Gly Arg Gly Gly
            35                  40                  45

Gly Gly Gly Ser Gly Gly Gly Ser Gly Gly Gly Ser Gly Gly Gly
50                  55                  60

Ser Gly Gly Gly Ser Gly Gly Gly Ser Gly Gly Ser Gly Gly
65                  70                  75                  80

Gly Ser Gly Gly Gly Gly Ser Gly Gly Gly Ser Gly Gly Ser
                85                  90                  95

Gly Gly Gly Gly Ser Gly Gly Gly Gly Ser Gly Gly Gly Gly
                100                 105                 110

Gly Gly Gly Ser Gly Gly Arg Cys Pro Ile Asp Thr Leu Lys Leu Gly
            115                 120                 125

Val Cys Ala Asn Val Leu Asn Gly Leu Ile Asn Val Gln Leu Gly Thr
            130                 135                 140

Pro Pro Arg Gln Pro Cys Cys Ser Leu Ile Gln Gly Leu Ala Asp Leu
145                 150                 155                 160

Glu Ala Ala Val Cys Leu Cys Thr Ala Leu Arg Ala Asn Ile Leu Gly
                165                 170                 175

-continued

```
Ile Asn Leu Asn Leu Pro Ile Asn Leu Ser Leu Leu Val Asn Tyr Cys
            180                 185                 190

Gly Arg Ser Val Pro Ser Gly Phe Gln Cys Ser Asn
        195                 200
```

GENE PARTICIPATING IN LOW TEMPERATURE GERMINABILITY IN RICE AND UTILIZATION OF THE SAME

TECHNICAL FIELD

The present invention relates to a gene participating in a low temperature germinability and a technique for utilizing the same. More specifically, this invention relates to an isolated gene for low temperature germinability having the ability to improve the low temperature germinability in rice, the amino acid sequence encoded by the gene, a method of improving germinability under environmental stress (the stresses of low temperature, salt, and osmotic pressure) using the gene for the low temperature germinability, a transgenic plant transformed with the gene, and a method of detecting low temperature germinability in plants.

BACKGROUND ART

Resistance to environmental stress is an important trait in crops, and has until now been thought to be a complex trait controlled by a plurality of genes called quantitative trait loci (QTLs). Identifying these QTLs is believed to be important for achieving stable crop production in the world. The inventors have previously disclosed a method of screening gramineous plants having specific traits, and gene markers for use in such a method (Patent Document 1). In the course of conducting research on the low temperature germinability in rice, the inventors have also found, through QTL analysis of genes for germinability in rice, three QTLs, qLTG-3-1, qLTG-3-2, qLTG-4, on chromosome 3 and chromosome 4. The locus qTLG-3-1 which was found at the end of the short arm of chromosome 3 has a very large activity, from which it was concluded that it might be useful for improving the low temperature germinability in rice (Non-Patent Document 1).

In addition, of the three QTLs which act on the low temperature resistance at the germination stage, the inventors have carried out fine mapping on qLTG-3-1 (Non-Patent Documents 2 and 4). As a result, they have succeeded in narrowing the candidate regions for qLTG-3-1 to the approximately 96-kb region between the marker SSR125411-4.1 and the marker STS73-28 (Non-Patent Document 2). It was possible, from the fine mapping of QTLs controlling low temperature germinability, to infer this to be a candidate region for qLTG-3-1.

The inventors have also carried out QTL analyses on the seed germinability in rice under stress. The results suggest that qLTG-3-1 participates in responses to diverse stresses, including temperature, salt (NaCl), and osmotic pressure (mannitol) stress. In this QTL analysis, it became clear that a Italica Livorno gene exhibits a germinability-increasing activity and that a QTL which exhibits a high germinability to both salt and osmotic pressure stresses exists at the end of the short arm of chromosome 3 (Non-Patent Document 3).

Thus, low temperatures are a major environmental stress in world crop production, and the inventors have hitherto found, by means of QTL analysis using Italica Livorno, which has a high low-temperature germinability, three QTLs (quantitative trait loci) which participate in low temperature germinability. However, environmental stresses had been thought to be complex traits controlled by a plurality of genes, the genetic function of the qLTG-3-1 phenotype had remained to be clarified, and the qLTG-3-1 gene had yet to be isolated, identified or cloned.

Patent Document 1: Japanese Patent Application Laid-open No. 2003-180362

Non-Patent Document 1: *Ikushugaku Kenkyu* 5 (Suppl. 2), p. 212 (2003)

Non-Patent Document 2: *Ikushugaku Kenkyu* 8 (Suppl. 1), p. 153 (2006)

Non-Patent Document 3: *Ikushugaku Kenkyu* 5 (Suppl. 1), p. 117 (2007)

Non-Patent Document 4: *Theor. Appl. Genet.*, 108:794-799 (2004)

In light of these circumstances, the inventors have reflected on the above prior art and conducted extensive investigations with the aim of elucidating the genetic function of the qLTG-3-1 phenotype, isolating and identifying the qLTG-3-1 gene, and creating transformants by cloning this gene. In the course of these investigations, to elucidate the above QTL at the molecular level, the inventors have identified qLTG-3-1 by means of chromosome map-based cloning and discovered that this gene encodes proteins of unknown function. Also, qLTG-3-1 is strongly expressed in the embryo at the time of seed germination and, in transgenic plants obtained by means of a qLTG-3-1 promoter fused to GUS, distinctive GUS staining was observed in the bud scales and ventral scales which cover the coleoptile and seminal roots. The inventors also conducted further studies, in the course of which they succeeded in elucidating the function of qLTG-3-1, determining the base sequence of the qLTG-3-1 gene, determining the amino acid sequence encoded by this gene, creating transformants with the gene, and developing techniques for utilizing the gene.

DISCLOSURE OF THE INVENTION

Accordingly, the objects of the present invention are to provide a gene participating in low temperature germinability in rice, an amino acid sequence encoded by the gene, a method of improving germinability under environmental stresses (the stresses of low temperature, salt, osmotic pressure) that makes use of the gene, transformants created by the introduction of the gene, and a method of detecting the low temperature germinability in plants.

The present invention for solving the above problems is constituted of the following technical means.

(1) An isolated qLTG-3-1 gene having a low temperature germinability, which is originated from the rice line Italica Livorno and comprises a base sequence of SEQ ID NO: 1 in the sequence listing.

(2) The gene for the low temperature germinability according to (1) above, wherein the gene has a genetic mutation present in a portion of the base sequence of SEQ ID NO: 1, and has a low temperature germinability identical or similar to that of the base sequence of SEQ ID NO: 1.

(3) The gene for the low temperature germinability according to (1) above, wherein the gene has a germinability-improving function under environmental stresses of low temperature, salt (NaCl) and osmotic pressure of mannitol.

(4) An amino acid sequence encoded by the gene for the low temperature germinability defined in (1) above, having a function improving a low temperature germinability, comprising the amino acid sequence of SEQ ID NO: 20 in the sequence listing.

(5) A transgenic plant transformed with the gene for the low temperature germinability defined in (1) or (2) above, which has an improved low temperature germinability.

(6) The transgenic plant according to (5) above, wherein the plant is rice.

(7) A method of analyzing a low temperature germinability, comprising analyzing a low temperature germinability of a cultivar by comparing the base sequence of the gene for the low temperature germinability defined in (1) or (2) above with a genotype of the cultivar.
(8) The method of analyzing low temperature germinability according to (7) above, wherein the cultivar is rice.
(9) A method of improving a low temperature germinability of rice, comprising transforming a rice cultivar with the gene for the low temperature germinability defined in (1) or (2) above to improve the low temperature germinability of the cultivar under low temperature conditions.

Next, the present invention is described in greater detail.

The present invention provides a gene for a low temperature germinability which is an isolated qLTG-3-1 gene from the rice line Italica Livorno, has low temperature germinability, and is characterized by having the base sequence of SEQ ID NO: 1 in the sequence listing. The preferred embodiments of the present invention are that the above gene for low temperature germinability has a genetic mutation present in a portion of the base sequence of SEQ ID NO: 1 and has a low temperature germinability identical or similar to that of the base sequence of SEQ ID NO: 1, the genetic mutation is due to the addition, deletion or substitution of a base sequence, and the above gene for low temperature germinability has a germinability-improving function under environmental stresses of low temperature, salt (NaCl) and osmotic pressure (mannitol).

The present invention also provides an amino acid sequence which is encoded by the above gene for low temperature germinability, has a low temperature germinability-improving action, and has the amino acid sequence of SEQ ID NO: 20 in the sequence listing. The present invention also provides a transgenic plant obtained by recombination of the above gene for low temperature germinability in a plant to improve the low temperature germinability thereof. In one preferred embodiment of the transgenic plant of the present invention, the plant is rice. In another preferred embodiment, the qLTG-3-1 promoter +qLTG-3-1 gene has been introduced into the plant to improve the low temperature germinability. In yet another preferred embodiment, the 35S promoter +qLTG-3-1 gene has been introduced into the plant to induce overexpression of gene qLTG-3-1 for the low temperature germinability.

The present invention also provides a method of analyzing low temperature germinability, comprising analyzing the low temperature germinability in a cultivar by comparing the base sequence of the above gene for low temperature germinability with the genotype of the cultivar. In a preferred embodiment of the method of analysis of the present invention, the cultivar is rice. In addition, the present invention also provides a method of improving the low temperature germinability in rice, comprising introducing the above gene for low temperature germinability into a rice cultivar by crossing or transformation so as to improve the low temperature germinability in the cultivar under low temperature conditions.

Next, the isolation of the gene for the low temperature germinability of the present invention is described in detail. The plant materials used were Hayamasari, a rice originated in Japan that is a *Japonica* rice variety, and Italica Livorno, a rice originated in Italy. With regard to NILHYqLTG-3-1, which is a near-isogenic line (NIL) for qLTG-3-1, a 360-kb chromosomal region near qLTG-3-1 from Italica Livorno was introduced into Hayamasari. Based on the phenotype and genotype of low temperature germinability, BIL116 was screened from the recombinant self-fertile line BILs obtained by crossing Hayamasari with Italica Livorno. BIL116 was backcrossed with Hayamasari by marker-assisted screening in order to create NIL.

To study the germinability under difference stress conditions, germination tests were carried out according to the method reported by Fujino et al. (2004). For low-temperature stress, seeds were placed on Petri dishes which were then loaded into an incubator. Solutions of plant hormones (ABA and GA), NaCl and mannitol at different concentrations were added to the Petri dishes which were then placed in an incubator.

The fine mapping and high-resolution mapping of qLTG-3-1 were performed in order to carry out the positional cloning of qLTG-3-1. Molecular markers and polymorphism between both parents mentioned in subsequent Table 1 were used for this purpose. BIL116 was crossed with Hayamasari, and backcross progeny were created for the sake of fine mapping and high-resolution mapping. An F2 population composed of 256 individuals was used for fine mapping.

The genotype of each recombinant F2 individual at the qLTG-3-1 locus was determined by germination testing the F3 progeny at a low temperature. The three genotypes—homozygous for the Italica Livorno allele, homozygous for the Hayamasari allele, and heterozygous—were clearly distinguishable. These F2 individuals were used in fine mapping of qLTG-3-1, in addition to which a BC1F2 population composed of about 3,200 individuals was used in high-resolution mapping.

The genomic DNA was extracted according to the method reported by Fujino et al. (2004). The genomic DNA was used in a polymerase chain reaction (PCR) for the purpose of cosegregation with a molecular marker-bearing phenotype based on PCR. In addition to the two SSR markers developed thus far (Fujino et al., 2004), using the Nipponbare genome, eight SSR markers (see subsequent Table 1) were prepared for fine mapping according to the method reported by Fujino et al. (2004).

For high-resolution mapping, six molecular markers were created based on 14 differences in the genomic sequence between Hayamasari and Italica Livorno (see subsequent Tables 1 and 2). For sequencing to detect polymorphisms between the parents in the 96-kb region, both strands of the PCR product from the parents were directly sequenced using a Big Dye Terminator v3.1 Cycle Sequencing Kit (Applied Biosystems).

For association analysis, 69 *Japonica* rice varieties were classified based on the qLTG-3-1 genotype. To detect the Hayamasari allele, PCR which amplifies deleted regions found in Hayamasari was carried out using the primers S103U and S103L (see subsequent Table 4). To detect the Nipponbare allele, the above-mentioned PCR product was digested with BseRI. The base sequence GAGGAG in the Italica Livorno allele was digested with BseRI, and the base sequence GTGGAG in the Nipponbare allele was digested with BseRI. Genotypes of Hayamasari, Nipponbare and Italica Livorno were found in, respectively, 28, 20 and 21 rice varieties. The mean low temperature germinabilities of the respective genotypes were compared by analysis of variance.

To carry out an analysis of gene expression, the total RNA was extracted from various organs of rice using RNAiso (TAKARA). The total RNA (0.5 µg) was reverse-transcribed with Rever Tra Ace (TOYOBO) having an Oligo(dT)$_{20}$ primer, in accordance with the manufacturing guidelines. The PCR reaction was carried out using KOD-plus (TOYOBO). Each PCR reaction (10 µL) included 0.5 µL of cDNA template that had been diluted 5-fold. The specificity of each primer for the target gene was confirmed by PCR product sequencing. For the purpose of Northern blotting analysis, the total RNA (4 µg/sample) was isolated on 2.0% (w/v) agarose-modified formaldehyde gel containing 40 mM MOPS (pH 7.0), 10 mM Na-acetate, 1 mM EDTA and 2% (v/v) formaldehyde.

The RNA was transferred with 20×SSC to a positively charged nylon membrane (Roche Diagnostics). Hybridization and signal detection were carried out by, respectively, a DIG system and CDP-star (Roche Diagnostics). The PCR fragments from the primers 13-5U and 13-5L were used as the probes for Northern blot analysis. The primers and amplification conditions for RT-PCR analysis are shown subsequently in Table 5.

To carry out plasmid construction and transformation, a 3-kb genomic DNA fragment of qLTG-3-1 from Italica Livorno was amplified by PCR using the primers Ano13-LA5U and Ano13-LA5L (see subsequent Table 4). To create a qLTG-3-1 promoter GUS gene fusion construct, a 2-kb genomic DNA fragment of the 5' upstream region of qLTG-3-1 from Italica Livorno was amplified by PCR using the primers Ano13-10U and Ano13-10L (see subsequent Table 4).

Because a promoter sequence that fully expresses the true qLTG-3-1 gene has yet to be identified, a 2k-bp 5' upstream region from the initiation codon of qLTG-3-1 was used as the promoter. These PCR products were cloned to, respectively, the BamHI/SacI and HindIII/BamHI sites of the pBluescript II SK vector (Stratagene).

Next, these fragments and the GUS gene were cloned to the pPZP2H-lac Ti-plasmid vector (Fuse et al., 2001). To produce an overexpression plant, a construct in which the qLTG-3-1 gene was ligated below the 35S promoter was created. PCR products from the primers Ano13-LA5U and Ano13-LA5L were digested with BamHI and SacI. These fragments were cloned at the SadI site of the pPZP2Ha3 Ti-plasmid vector (Fuse et al., 2001).

An *Agrobacterium*-mediated transformant was used to transform Hayamasari (Toki, 1997; Toki et al., 2006). A plant regenerated from a hygromycin-resistant callus (T0 plant) was grown in an isolated greenhouse. The T1 transformant was subjected to selection by PCR on the transgene, cultivation and collection (T2 generation), and furnished to germination experiments.

To carry out the histochemical analysis of GUS expression, the seeds of transgenic plants having qLTG-3-1::GUS were incubated at 30° C. Under these conditions, germination (emergence of the coleoptile) began to arise in a very small percentage of the seeds two days after treatment. The seeds of the transformants were collected as specimens 0, 1 and 2 days after treatment. All the seeds of transgenic rice and longitudinally cut seeds were vacuum immersed in 50 mM $NaH_2PO_4$ (pH 7.0) containing 0.5 mM X-Gluc, 0.5 mM $K_3(Fe(CN)_6)$, 0.5 mM $K_4(Fe(CN)_6)$ and 0.5% (v/v) Triton X-100, and incubated at 37° C. for 6 hours. Next, 70% EtOH was added thereto to halt the enzyme reaction at room temperature.

Rice seed of the AA genome wild rice species W0106 (*O. rufipogon*), W0652 (*O. barthii*), W1169 (*O. glumaepatula*), W1413 (*O. longistaminata*) and W1508 (*O. longistaminata*) were acquired from the National Institute of Genetics of the Research Organization of Information and Systems as wild relatives of cultivated rice. The seeds of a core collection of cultivated rice (*O. sativa*) containing 62 varieties (Kojima et al., 2005) were acquired from the National Institute of Agrobiological Sciences.

This collection was composed of three groups, Groups A, B and C, which correspond to *Japonica*, *Aus* and *Indica* (Kojima et al., 2005). The total DNA was isolated from young leaves thereof, using CTAB, by the method reported by Fujino et al. (2004). The qLTG-3-1 gene region was amplified using primers (see subsequent Table 4), then directly sequenced using cycle sequencing with a Big Dye Terminator (Applied Biosystems).

Sequencing was carried out with a Prism 3700 automated sequencer (Applied Biosystems). Alignment of the DNA sequences was carried out using BioEdit (http:www.mbio.ncsu.edu/BioEdit/bioedit.html), following which the sequences were visually confirmed. All polymorphisms were rechecked from chromatograms.

In the sequences found by the inventors, heterozygotes were not observed. A 1,784-bp gene in the qLTG-3-1 gene region that includes a 933-bp upstream region containing 5' and 3'UTR and a 296-bp downstream region, excluding TA repeats in the 50-bp region from base pairs 433 to 384, was sequenced from the cultivated rices and the wild varieties.

A haplotype network showing unique DNA sequences obtained from gene polymorphism or lineage relationships between alleles was constructed by the computer program TCS (Crandall et al., 2000) using the parsimony method in statistics.

Conferring resistance to environment stresses is an important breeding objective in the stable production of crops. In rice cultivation within cold-weather regions, low temperatures are a major stress. Up until now, low-temperature resistance had been thought to be a complex trait controlled by a plurality of genes called quantitative trait loci (QTLs). This has been addressed in the present invention by isolating genes which are quantitative trait loci and have a large gene activity associated with the low temperature germinability in rice, and carrying out functional analysis on these genes.

The quantitative trait locus qLTG-3-1 in the rice line Italica Livorno having an excellent low temperature germinability has been isolated as a gene for a low temperature germinability. In the present invention, this qLTG-3-1 was molecularly identified by the positional cloning method. This gene was composed of 555 base pairs, and was a novel gene of unknown function. When a functional gene was introduced into the rice strain Hayamasari having a nonfunctional gene by an *Agrobacterium* method, a low temperature germinability higher than that of Hayamasari was exhibited, from which it became apparent that this 555-bp sequence was the target gene qLTG-3-1 for low temperature germinability.

A near-isogenic line obtained by using DNA marker screening and backcrossing to introduce the chromosomal region containing the functional gene qLTG-3-1 of Italica Livorno into the rice variety Hayamasari having a nonfunctional gene exhibited a high germinability not only at low temperatures, but also under salt (NaCl) and osmotic pressure (mannitol) stresses. This suggests that qLTG-3-1 is a gene for resistance to a plurality of stresses.

As a result of gene expression analysis, high expression of qLTG-3-1 was confirmed, particularly in embryos at the time of seed germination. Moreover, high expression was also observed in the panicles prior to panicle emergence. The GUS gene was thus ligated to a 2-kb upstream region on the 5' side of the initiation codon, and this construct was introduced by the *Agrobacterium* method into Hayamasari. As a result, GUS activity was observed in the seed embryos at the time of germination. It became clear from these observations that qLTG-3-1 is specifically expressed in seed embryos during germination, and that this specificity is controlled by at least a 2-kb upstream region on the 5' side.

On comparing the gene sequences of the gene qLTG-3-1 for the low temperature germinability, it was found that Italica Livorno, which exhibits a high low-temperature germinability, had a functional gene sequence, whereas Hayamasari had lost functionality due to the deletion of some 71 base pairs.

Nipponbare had a single base substitution that gives rise to an amino acid mutation. Hence, an association analysis on the qLTG-3-1 genotype and low temperature germinability was carried out for about 70 rice varieties.

As a result, the following relationship in low temperature germinability was clearly observed among the three lines: Italica Livorno>Nipponbare>Hayamasari. It was apparent from this that the low temperature germinability can be inferred by discerning gene mutations. Also, the mutated amino acid observed in Nipponbare was thought to be related to the function of the gene. The region containing this mutated amino acid was highly conserved even in genes homologous to qLTG-3-1 in plants.

In the present invention, to create a marker for narrowing the candidate region of qLTG-3-1, an 86-kb candidate region in Italica Livorno and a 90-kb candidate region in Hayamasari were PCR amplified based on the Nipponbare sequence, and sequence analysis was carried out. As a result, mutations at 14 places were identified; six of these were rendered into markers and used to screen recombinant individuals from a large-scale population. About 3,200 individuals were furnished for testing; it was possible with these to narrow the candidate region for qLTG-3-1 to the 4.8-kb between markers D and F. Using the Rice Annotation Database (RAP-DB), it was predicted that one gene of unknown function is present in this region.

Compared with the functional gene of Italica Livorno, a 71-bp deletion arose in Hayamasari, which clearly resulted in a loss of function. When the functional gene of Italica Livorno was introduced into Hayamasari, the transformant T2 clearly exhibited a higher low-temperature germinability than Hayamasari. It was thus possible to confirm that this is the gene responsible for gene qLTG-3-1 for the low temperature germinability.

The expression of the qLTG-3-1 gene was observed to have a high tissue specificity. Gene expression was especially strong in embryos during seed germination; expression was not observed in the endosperm. Because expression of this gene is observed even during germination under both 30° C. and 15° C. conditions, this is not a gene that is induced by low-temperature stress. Moreover, given that expression is not observed even in the embryo portion during ripening and that expression rises with elapsed time following germination treatment, it was apparent that qLTG-3-1 exhibits specific gene expression at the time of germination.

Expression of the qLTG-3-1 synthesis genes (OsGA20ox1, OsGA20ox2, OsGA3ox2) and the amylase gene (Ramy 1A) during germination was analyzed using Italica Livorno having the qLTG-3-1 functional gene. Gene expression by qLTG-3-1 was observed 6 hours after treatment at 30° C., and 12 hours after treatment at 15° C. At 30° C., gene expression by OsGA20ox1, OsGA3ox2 and Ramy 1A was similarly observed after 6 hours. On the other hand, at 15° C., gene expression by OsGA20ox1 was observed after 12 hours, as in the case of qLTG-3-1, and gene expression by OsGA3ox2 and Ramy 1A was observed after 24 hours. It was apparent from this that the expression of these genes begins at about the same time as gene expression by qLTG-3-1.

Such a gene expression pattern was also observed in the Hayamasari near-isogenic line NILHYqLTG-3-1 for the qLTG-3-1 functional gene from Italica Livorno. Also, in Hayamasari having the qLTG-3-1 nonfunctional gene, the expression of all these genes was delayed. Based on this, it appears that the expression of these genes is induced at an early stage by qLTG-3-1, resulting in a high low-temperature germinability being expressed as a trait.

The responsiveness of qLTG-3-1 to environmental stresses other than low temperatures was analyzed using NIL-HYqLTG-3-1. As a result, an increase in germinability was observed also in the presence of NaCl and mannitol. Also, in the presence of ABA, the germination of Italica Livorno and Hayamasari was delayed, whereas in the presence of NIL-HYqLTG-3-1, germination was inhibited.

In addition, by means of this invention, mutations of the qLTG-3-1 gene were elucidated. Hayamasari contained a nonfunctional gene due to a 71-bp deletion with respect to the functional gene qLTG-3-1 of Italica Livorno. In Nipponbare, a single base substitution accompanied by an amino acid mutation arose with respect to the functional gene. As a result of database analysis using qLTG-3-1 base sequences, homologous genes were present in the following plant families: Poaceae, Solanaceae, Leguminosae and Cucurbitaceae. When these amino acid sequences were compared, a highly conserved sequence was detected at the N-terminus (8 amino acid sequences). The amino acid mutation that arose in Nipponbare took place within this conserved sequence.

Here, in order to clarify the function of the Nipponbare type qLTG-3-1 gene, an association analysis was carried out using 69 rice lines ranging from varieties native to Hokkaido to present-day varieties. As a result, clear differences were observed in the qLTG-3-1 genotypes and low temperature germinabilities in these lines. The germination rate was 80.8% among Italica Livorno rices (21 lines), 69.7% among Nipponbare rices (20 lines), and 30.7% among Hayamasari rices (28 lines); hence, significant differences were obtained. These results showed that the amino acid mutation which arose in Nipponbare lowers somewhat the gene function of qLTG-3-1. In addition, the conserved amino acid sequence was also thought to have an important role in gene function.

To search for the qLTG-3-1 genotype mutations in cultivated rice, the 1784-bp gene sequence was compared for 62 lines from the world core collection. As a result, in-frame insertions and deletions were noted at three places in the structural gene region, but no amino acid substitutions were present. Such insertions and deletions gave rise to differences in the number of repeats within the reiterated sequence region. These results showed that qLTG-3-1 is functionally important; hence, it is thought to be a highly conserved gene. Also, on the basis of these base substitutions, the core collection was made up of two haplogroups of 10 haplotypes.

The following effects are achieved by the present invention.

(1) A gene for a low temperature germination gene isolated from the rice line Italica Livorno and its base sequence can be provided.
(2) An amino acid sequence which is encoded by the above gene and has a low temperature germinability-improving action can be provided.
(3) By elucidating the functions of the above gene for low temperature germinability alone (germinability-improving properties under low temperature, salt, and osmotic pressure stresses), techniques which utilize this gene (e.g., methods for improving low temperature germinability) can be furnished.
(4) By elucidating the tissue-specific gene expression mechanisms, the low temperature germinability in plants can be efficiently and easily studied.
(5) By creating transgenic rice in which the above gene has been introduced, rice having an improved low temperature germinability can be developed and furnished.
(6) By identifying the genotypes of the rice lines, the level of low temperature germinability of the rice can be discerned.

(7) Relationships between the genotype and the low temperature germinability in cultivated varieties can be checked by identifying the genotype.

BRIEF DESCRIPTION OF THE DRAWINGS

FIG. 1 is a graph of the genotypes of BIL116(A) and NIL(B). The black, white and hatched areas represent chromosomal fragments from, respectively: Italica Livorno, Hayamasari, and heterozygotes. The mapped markers were matched to chromosomal positions assigned by high-density RFLP linkage markers (Harushima et al, 1998).

FIG. 6 shows the nucleotide sequences of qLTG-3-1 for the rice varieties Italica Livorno, Hayamasari and Nipponbare. Italica Livorno=SEQ ID NO:113, Havamasari=SEQ ID NO:114, and Nipponbare=SEQ ID NO:115.

FIG. 7 shows the amino acid sequences of qLTG-3-1 for the rice varieties Italica Livorno, Hayamasari and Nipponbare. Italica Livorno=SEQ ID NO:116, Hayamasari=SEQ ID NO:117, and Nipponbare=SEQ ID NO:118.

FIG. 9 shows the N-terminal amino acid sequence for qLTG-3-1 and related proteins. Common amino acid residues are indicated by dots. The sequence identifiers from top to bottom are SEQ ID NOs:119-141.

FIG. 20 shows a qLTG-3-1::GUS construct.

FIG. 26 shows nucleotide sequences of qLTG-3-1, etc. in the rice core collection and wild types thereof. The sequence identifiers for the sequences spanning over FIGS. 26-34 for qLTG-3-1 to W1508 are SEQ ID NOs:142-157, respectively.

FIG. 27 shows nucleotide sequences of qLTG-3-1, etc. in the rice core collection and wild types thereof.

FIG. 28 shows nucleotide sequences of qLTG-3-1, etc. in the rice core collection and wild types thereof.

FIG. 29 shows nucleotide sequences of qLTG-3-1, etc. in the rice core collection and wild types thereof.

FIG. 30 shows nucleotide sequences of qLTG-3-1, etc. in the rice core collection and wild types thereof.

FIG. 31 shows nucleotide sequences of qLTG-3-1, etc. in the rice core collection and wild types thereof.

FIG. 32 shows nucleotide sequences of qLTG-3-1, etc. in the rice core collection and wild types thereof.

FIG. 33 shows nucleotide sequences of qLTG-3-1, etc. in the rice core collection and wild types thereof.

FIG. 34 shows nucleotide sequences of qLTG-3-1, etc. in the rice core collection and wild types thereof.

FIG. 35 shows amino acid sequences of qLTG-3-1, etc. in the rice core collection and wild types thereof. The sequence identifiers for the sequences spanning over FIGS. 35-37 for qLTG-3-1 to W1508 are SEQ ID NOs:158-173, respectively.

FIG. 36 shows amino acid sequences of qLTG-3-1, etc. in the rice core collection and wild types thereof.

FIG. 37 shows amino acid sequences of qLTG-3-1, etc. in the rice core collection and wild types thereof.

BEST MODE FOR CARRYING OUT THE INVENTION

Next, the present invention is described more concretely by means of examples. However, it is to be understand that these examples do not limit in any way the present invention.

Example 1

In this example, a genetic assessment of qLTG-3-1 was carried out. The plant materials used were Hayamasari, a rice originated in Japan that is a *Japonica* rice variety, and Italica Livorno, a rice originated in Italy. Based on the phenotype of low temperature germinability and the genotype of qLTG-3-1, BIL116 was screened from recombinant self-fertile lines (BILs) obtained by crossing Hayamasari and Italica Livorno. FIG. 1 is a graph of the genotypes of BIL116(A) and NIL(B).

BIL116 was backcrossed with Hayamasari by DNA marker screening in order to create a near-isogenic line (NIL), thereby forming a population of $BC_3F_1$ individuals. Of the 66 $BC_3F_1$ plants, #59 having the smallest portion of the genome that included qLTG-3-1 from the donor Italica Livorno, was backcrossed. In addition, the genotype of the entire genome of #59 was examined. Based on this, a single individual out of the eleven #59 individuals from the $BC_3F_1$ population was selected: #59-11.

Figure 2:
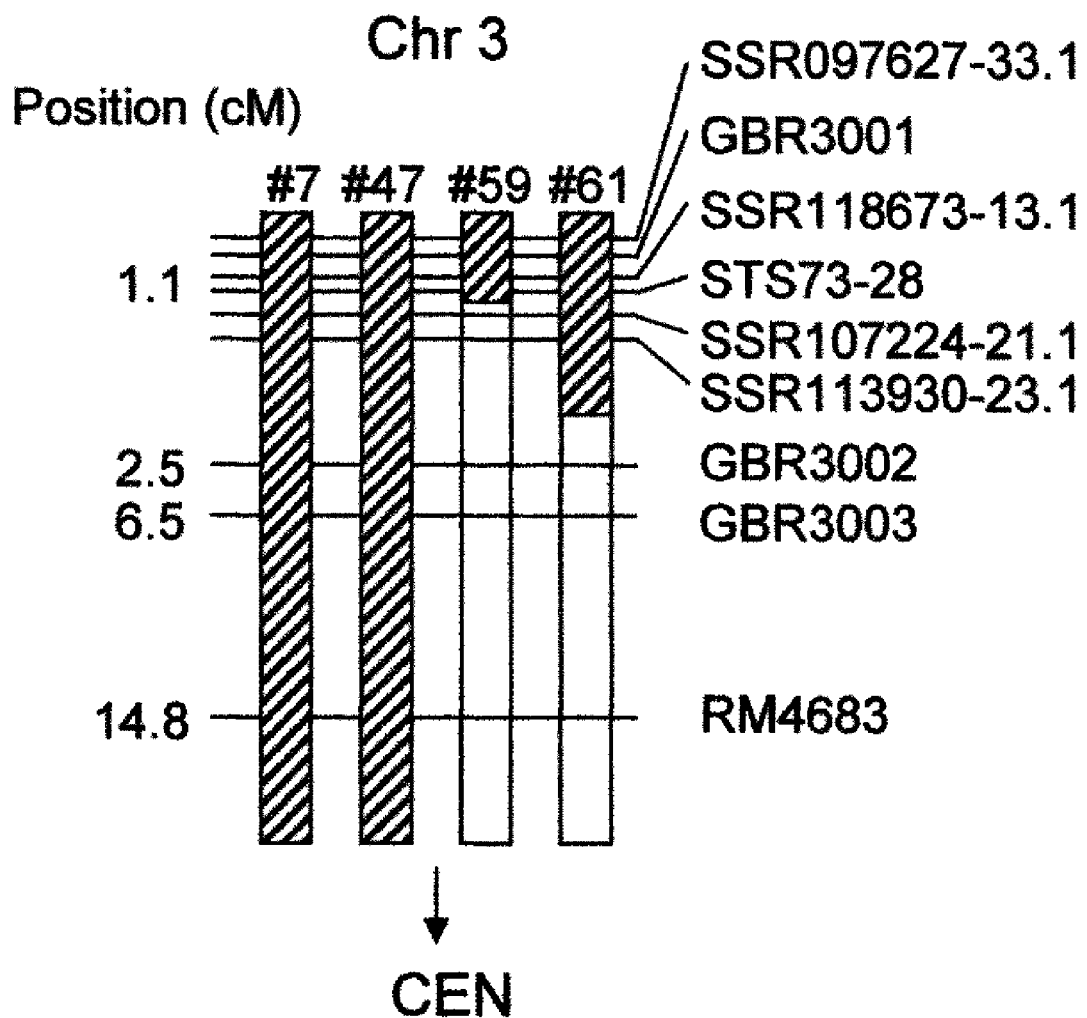
FIG. 2 shows NIL genotypes near qLTG-3-1. The white and hatched areas respectively represent chromosomal fragments from Hayamasari and the heterozygote.

Of the $BC_3F_2$ progeny obtained by self-fertilization of $BC_3F_1$ individual #59-11, those individuals homozygous for the Italica Livorno allele in the qLTG-3-1 region were selected (B in FIG. 1). The NIL fragment had a gene recombination on one side of qLTG-3-1, between the markers STS73-28(I) and SSR107224-21.1 (Table 1, FIG. 2). NIL-HYqLTG-3-1 possesses a 360-kb chromosomal region near qLTG-3-1 that was imported into Hayamasari from Italica Livorno.

TABLE 1

List of the SSR and STS markers developed and used in this study

| Category | Type | Marker | Marker position in mapping | Forward primer | | Reverse primer | | Position |
|---|---|---|---|---|---|---|---|---|
| | | | | Name | Sequence | Name | Sequence | |
| fine mapping | SSR | SSR097627-33.1 | | SSR097627-33.1U | CCAACAACAA GGCAATCGCG | SSR097627-33.1L | CGAGGGGGAA AAGGGCTAGA | 67,539 |
| | SSR | SSR097627-22.1 | | SSR097627-22.1U | TGAGTTTGGA GTGATTGGAT | SSR097627-22.1L | CTCAAAGAAT GACACCGATG | 99,844 |
| | SSR | GBR3001a | a | GBR3001aU | CCTCTTCCCT TCTTGTGTCA | GBF13001aL | GGGATTTTTT CATCGAAATT | 117,791 |
| | SSR | SSR125411-4.1 | A | SSR125411-4.1U | GATCGATCGA CATTACACAC | SSR125411-4.1L | GCATGCATGG ACTAGTAATT | 157,388 |
| | SSR | SSR118673-13.1 | D | SSR118673-13.1U | CAATTAAGTT AACCCGATGA | SSR118673-13.1L | GCTTGTTGCT GTTCTGTACT | 196,244 |
| | STS | STS73-28 | 1 | STS73-28U | GCTTATCCGATTC CGTCTGCGGTTA | STS73-28L | TTGAGACATGCCT AATTAAGCGAAC | 253,333 |
| | SSR | SSR107224-21.1 | | SSR107224-21.1U | TTAGGTAAAA TTAAGGCACC | SSR107224-21.1L | TCTGTTGTAG GTGTAGCAGC | 359,550 |
| | SSR | SSR107224-13.1 | b | SSR107224-13.1U | ATTTGTGTTG CTGCATGCAG | SSR107224-13.1L | ACTCGATCTC GTGTGTGCCA | 370,778 |

TABLE 1-continued

List of the SSR and STS markers developed and used in this study

| Category | Type | Marker | Marker position in mapping | Forward primer | | Reverse primer | | Position |
|---|---|---|---|---|---|---|---|---|
| | | | | Name | Sequence | Name | Sequence | |
| | SSR | SSR113930-23.1 | c | SSR113930-23.1U | GCAACTCTGCTAAACGAATT | SSR113930-23.1L | TAGCCCCATGATAAGAGATT | 514,861 |
| | SSR | SSR105363-21.1 | | SSR105363-21.1U | GCTCGCTCCCCACATTTTAA | SSR105363-21.1L | GGCATCAGCAACAGCAGCTA | 1,134,844 |
| | SSR | GBR3002a | d | GBR3002aU | AGAGCATAACATCAAAGCCA | GBR3002aL | ATAGCTCCAATTCGATCTTC | 1,322,466 |
| high-resolution mapping | SSR | S70 | | S70U | AGGGCTAAGTCGGAAGAATCAT | S70L | GGAGTCGTGGGGGTCGGTGT | 157,592 |
| | SSR | S65 | | S65U | CATATTCAAAATAGCTAAGGGAGC | S65L | CGCACACATACAAGAGTTTTACT | 160,269 |
| | indel | S51a | | S51aU | TCAGCAAATATCATCTCCCA | S51aL | GTGTCACCCTAGTGAAAAAATTT | 165,027 |
| | SNP | S51b | | S51bU | TCAGCAAATATCATCTCCCA | S51bL | GTGTCACCCTAGTGAAAAAATTT | 165,053 |
| | SSR | S57 | B | S57U | CTCACATTCCCTTGCTATGCT | S57L | CCATCAATTAATTCTTCCGATC | 17,349 |
| | indel | S21a | | S21aU | TGAAAATACACGCATGGCTG | S21aL | GAGAGCGAATGCGCTGCTTC | 174,798 |
| | SSR | S21b | | S21bU | TGAAAATACACGCATGGCTG | S21bL | GAGAGCGAATGCGCTGCTTC | 174,986 |
| | SNP | S43 | C | S43U | TTAATCCATGGAAGTTAAAGAATAT | S43L | GTCCATGATTAGCTATAAGTGCTAC | 191,822 |
| | indel | S103a | E | S103aU | CAGCTAAGCTACCAAAAGCCCA | S103aL | TTATCAGCCCATTCAGCACGTT | 198,461 |
| | SNP | S103b | | S103bU | CAGCTAAGCTACCAAAAGCCCA | S103bL | TTATCAGCCCATTCAGCACGTT | 198,464 |
| | SSR | S107 | F | S107U | CGCACGCGTATATTTGAATG | S107L | CAGATTAAATGGTTAGTTAACCGGC | 200,192 |
| | SSR | S306 | G | S306U | ACATGCATGCAGTGATTTCG | S306L | CTACTGCTCATCACTACAAAGAGTG | 230,403 |
| | SSR | S179 | H | S179U | CGGCGATGGTTAGTTAAATTATCC | S179L | CAAGCTAGGCAAAAGGTGGTATT | 233,798 |
| | SSR | S218 | | S218U | GTTAGTCATATCAGCCCCAAGAAC | S218L | ATTTGCCCATAAACTACCGCAC | 253,122 |

Position indicates the location of the upper primer in IRGSP build 3 in RAP-DB (http://rapdb.lab.nig.ac.jp/index.html)
a) Fujino et al. (2004)

Figure 3:
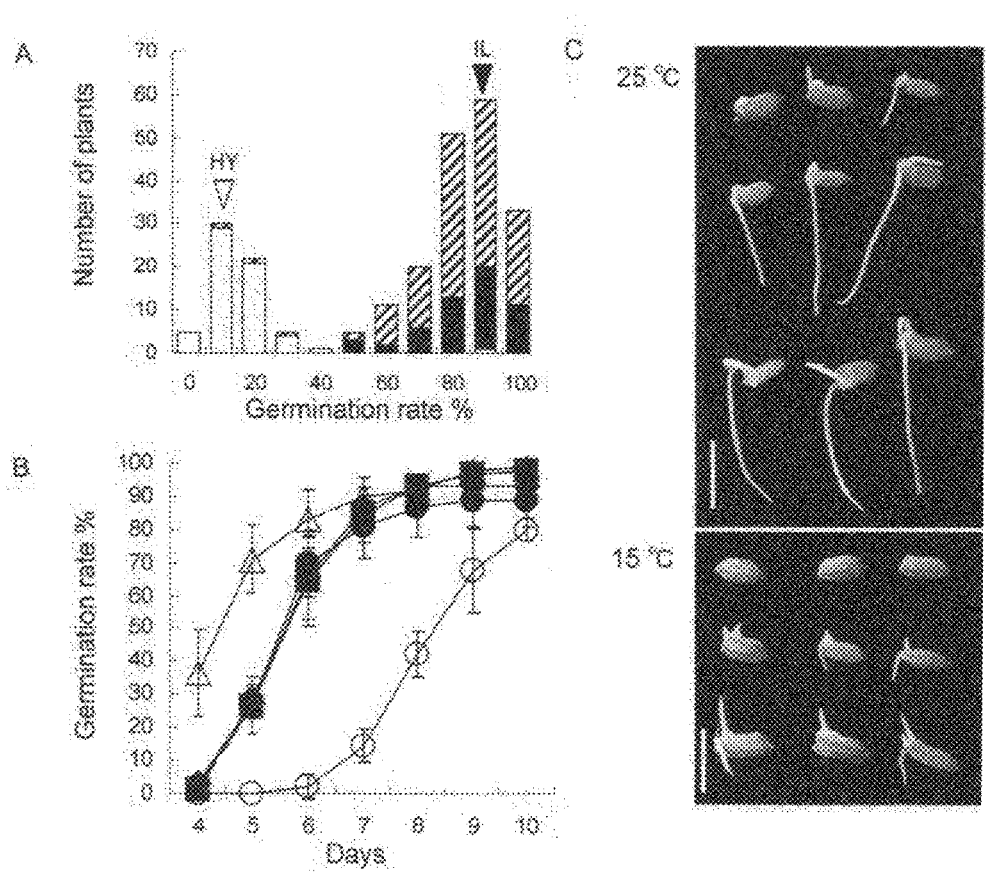
FIG. 3 shows the phenotype of the qLTG-3-1 gene. (A) is the frequency distribution of low temperature germinability in the backcross progeny. The arrows indicate Italica Livorno (IL) and Hayamasari (HY). The following classified genotypes evaluated by the marker GBR3001 are shown: homozygous for the Italica Livorno allele (black), heterozygous (hatched), and homozygous (white) for the Hayamasari allele. (B) shows the germination response at a low temperature (15° C.) by Hayamasari (open circles), NILHYqLTG-3-1 (closed circles) and Italica Livorno (open triangles). The numerical values represent the mean±standard deviation (SD) of triplicates. (C) shows the germination phenotypes of Hayamasari (top), NILHYqLTG-3-1 (middle), and Italica Livorno (bottom) that were germinated for 3 days at 25° C. and for 7 days at 15° C. The bars are 1 cm.

To date, the inventors have mapped three QTLs that control low temperature germinability by backcrossing recombinant self-fertile lines (BILs) obtained by crossing the low temperature germinating *Japonica* strain Italica Livorno with ordinary Hayamasari (Fujino et al., 2004). Of these, qLTG-3-1, the QTL thought to be the most effective, was mapped on chromosome 3. To determine the genetic basis of qLTG-3-1, segregation analysis of the low temperature germinability was carried out using the backcross progeny. FIG. 3 shows the phenotype of the qLTG-3-1 gene.

The frequency distribution of low temperature germinability in the backcross population had a clear single-factor segregation pattern (FIG. 3A), which indicated that qLTG-3-1 is a dominant gene. To elucidate the precise genetic effects of qLTG-3-1, the near-isogenic line (NIL) NILHYqTLG-3-1 was created by using DNA marker screening and backcrossing with Hayamasari. NILHYqLTG-3-1 exhibited a high low-temperature germinability compared with the recurrent parent Hayamasari (FIGS. 3B and C).

Example 2

In this example, the isolation of qLTG-3-1 was carried out. Molecular markers and the polymorphisms between both parents shown in Table 1 were used for the fine mapping and the high-resolution mapping of qLTG-3-1. BIL116 was crossed with Hayamasari, and the backcross progeny were bred for the purpose of fine mapping and high-resolution mapping. An F2 population composed of 256 individuals was used for fine mapping. The genotypes of each of the recombinant F2 plants at the qLTG-3-1 gene locus were determined by low temperature germination tests of their F3 progeny. The three genotypes—homozygous for the Italica Livorno allele, homozygous for the Hayamasari allele, and heterozygous—were clearly differentiated.

These recombinant F2 plants were used for the fine mapping of qLTG-3-1. In addition, a BC1F2 population of about 3,200 plants was used for high-resolution mapping. The genomic DNA was extracted according to the method described by Fujino et al. (2004). The genomic DNA was used in PCR analysis; based on the PCR, the phenotype cosegregated with the molecular markers.

In addition to the two SSR markers developed thus far (Fujino et al., 2004), the Nipponbare genome was used to create eight SSR markers (Table 1), according to the method described by Fujino et al. (2004), for the purpose of fine mapping.

For high-resolution mapping, six molecular markers were created (Tables 1 and 2) based on differences in 14 genomic sequences between Hayamasari and Italica Livorno. For sequencing to find polymorphisms between the parents in a 96-kg region, both strands of PCR products obtained from the parents were directly sequenced using the Big Dye Terminator v3.1 Cycle Sequencing Kit (Applied Biosystems).

The 69 *Japonica* varieties were classified according to the qLTG-3-1 genotype. To find the allelomorphs of Hayamasari, the primers S103aU and S103aL were used to carry out PCR so as to amplify deletions discovered in Hayamasari. The above PCR products were digested with BseRI in order to find the allelomorphs of Nipponbare.

GAGGAG in the Italica Livorno allelomorph was digested by BseRI, but GTGGAG in Nipponbare was not digested. The genotypes of Hayamasari, Nipponbare and Italica Livorno were found in, respectively, 28, 20 and 21 rice varieties. The average low temperature germination rates of the respective genotypes were compared by analysis of variance.

Figure 4:
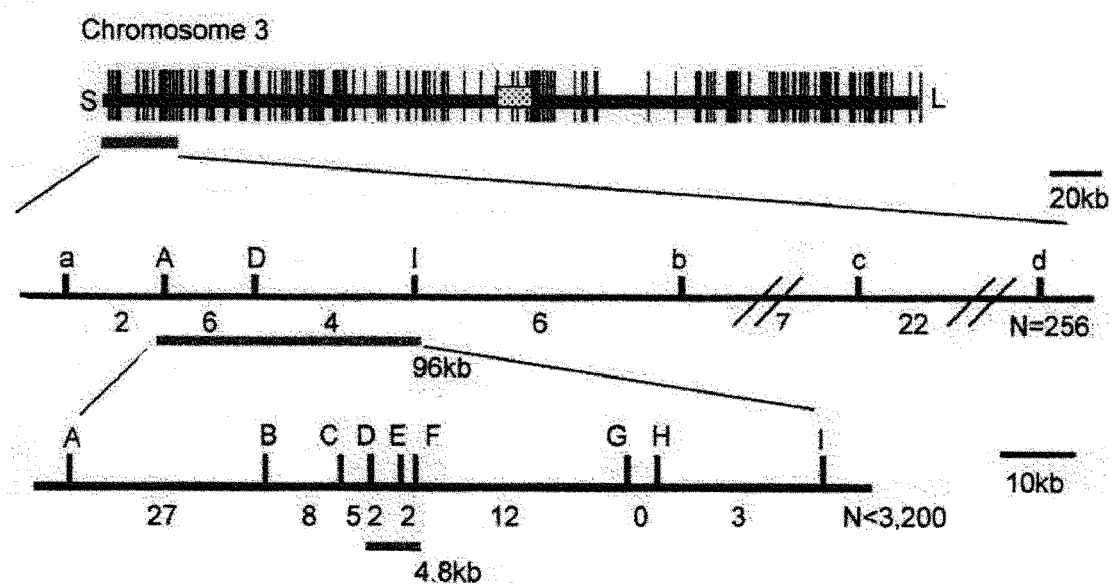
FIG. 4 shows the positional cloning of the qLTG-3-1 gene. The fine mapping which delimited the range of the 96-kb region of qLTG-3-1 in chromosome 3 (center) is shown. The high-resolution mapping (bottom) shows that a qLTG-3-1 is positioned in a 4.8-kb region between markers D and F, and cosegregates with marker E. The numerical values between the markers indicate the number of recombinant individuals between the markers.

Fine mapping of the genes was carried out using the backcross progeny. qLTG-3-1 was positioned in the 96-kb region between the markers SSR125411-4.1(A) and STS73-28(1). FIG. 4 shows the positional cloning of the qLTG-3-1 gene. In order to clone qLTG-3-1, a detailed chromosomal map of about 3,200 individuals was created. Because the parents were in a genetically close relationship, the target region had no SSR markers capable of being used. Hence, the target sequence of Hayamasari (about 90 kb) and the target sequence of Italica Livorno (about 86 kb) were sequenced. SSR, SNP, and 14 polymorphisms containing insertions/deletions were detected (Table 2).

of qLTG-3-1 in Hayamasari undergoes a loss of gene function. In Nipponbare, it is predicted that mutations of T to A at more than 50 positions in the coding region will convert Leu to His.

Figure 8:
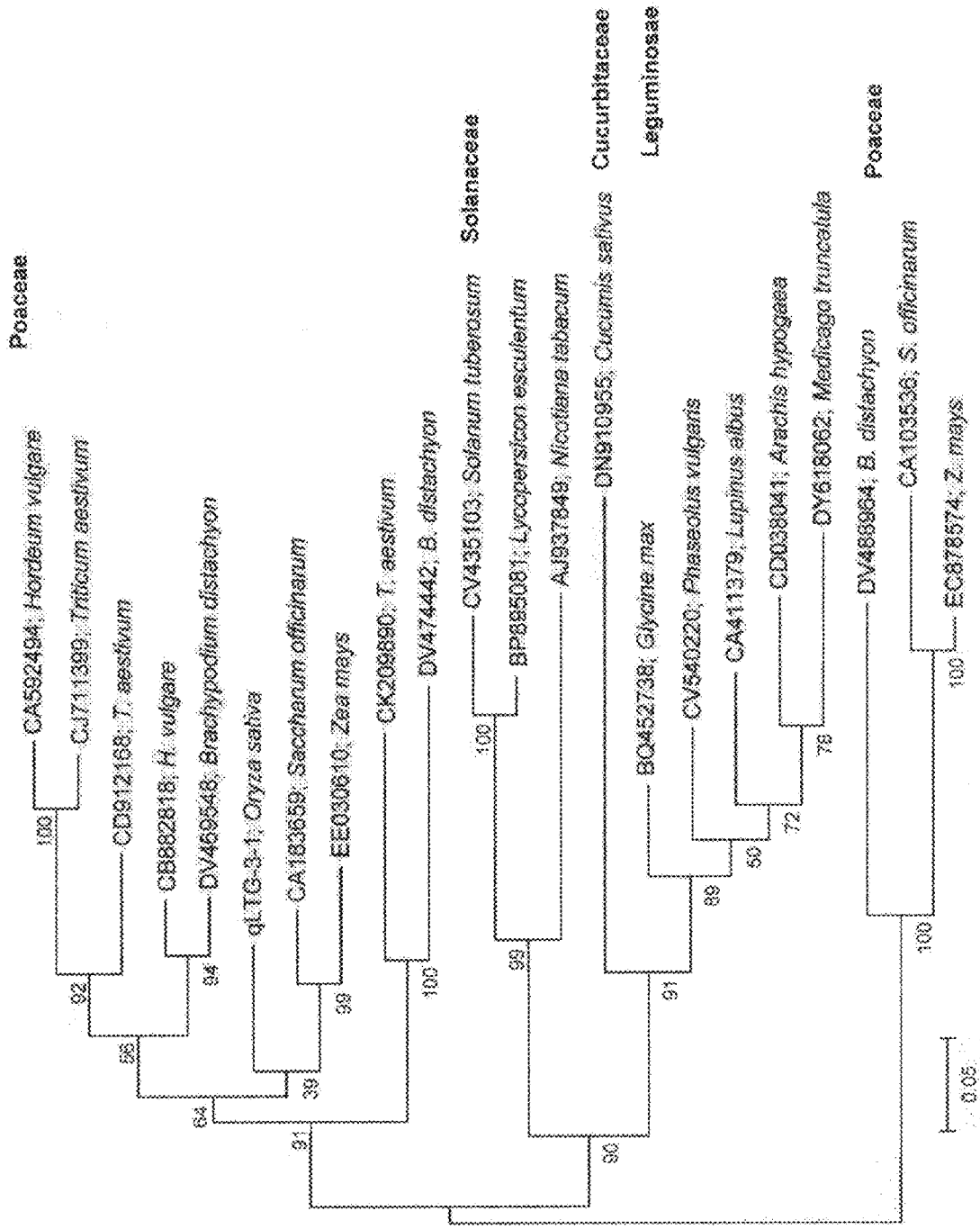
FIG. 8 shows the phylogenetic tree for qLTG-3-1 and related proteins. This phylogenetic tree was constructed using CLUSTAL W. The bootstrapping analysis values are shown as centerpoint branches. The scale shown indicates 0.05 amino acid substitution per site. The registration numbers and plant varieties are shown.

By means of a database search, 21 genes having significant homology to qLTG-3-1 were discovered only in plants. By phylogenetic analysis of these proteins which include qLTG-3-1, it was found that these proteins can be divided into two main classes. FIG. 8 shows the phylogenetic tree for qLTG-3-1 and related proteins. Class I included qLTG-3-1, and was composed of the two subclasses of monocotyledons and dicotyledons. Class II included only three monocotyledon proteins. In addition to the GRR and LTP domains, the amino acid AxxLALNLLFFxxxxAC (SEQ ID NO:141) was highly conserved in the N-terminal region. FIG. 9 shows qLTG-3-1 and the N-terminal amino acid sequences of related proteins.

Figure 10:
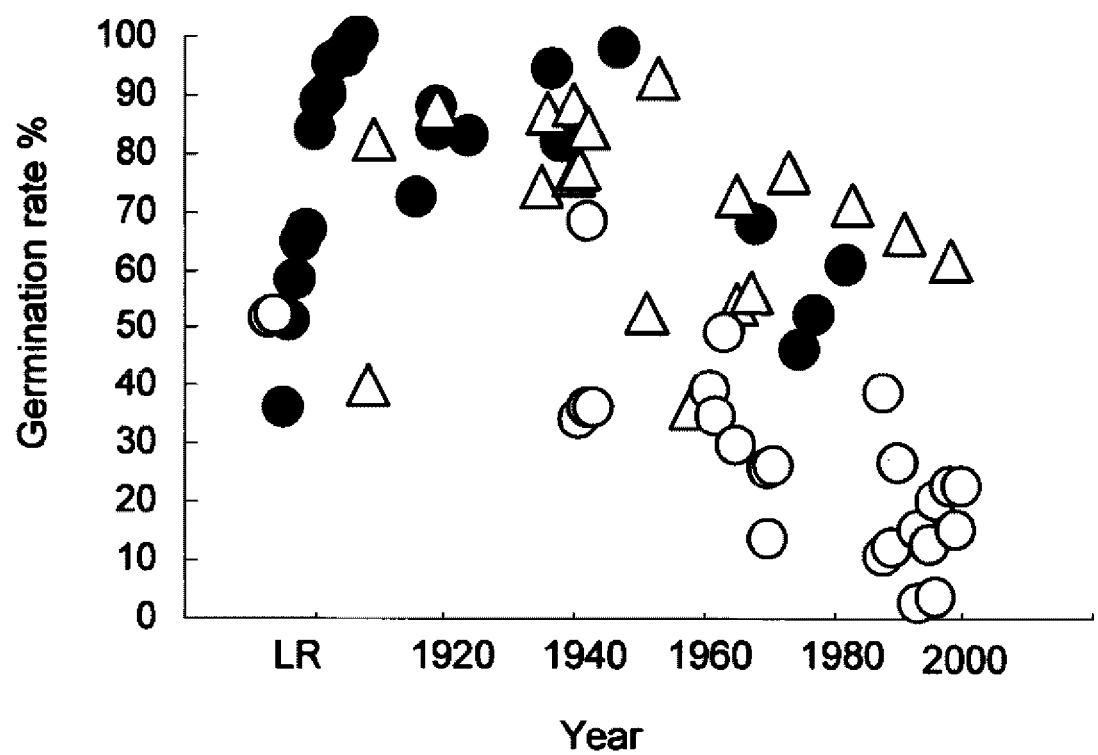
FIG. 10 shows the relationship between the genotype and low temperature germinability of qLTG-3-1 in rice varieties. The rice varieties were classified into the three qLTG-3-1 genotypes of a Italica Livorno type (closed circle), a Nipponbare type (open triangle), and a Hayamasari type (open circle).

In the Nipponbare sequence, the Leu residue at the 9 position on the converted amino acid mutated to His. To determine the function of the converted amino acid, an association analysis was carried out between the genotype of qLTG-3-1 and the phenotype of low temperature germinability. A total of 69 rice varieties were classified into the three qLTG-3-1 genotypes (Table 3, FIG. 10). The varieties having the Italica Livorno allele (80.0%) exhibited a higher low-temperature germination rate than the varieties having the Hayamasari allele (30.7%). The varieties having the Nipponbare allele

TABLE 2

Nucleotide polymorphism in 96-kb region of qLTG-3-1

| Locus | Marker in high resolution mapping | Position(NP ver3) | Type | Hayamasari | Italica Livorno | Nipponbare |
|---|---|---|---|---|---|---|
| S70 | | 157,592 | SSR(AT)n | T del | — | — |
| S65 | | 160,269 | SSR(A)n | AA ins | — | — |
| S51a | | 165,027 | indel | G del | — | — |
| S51b | | 165,053 | SNP | A | G | G |
| S57 | B | 17,349 | SSR(T)n | — | T ins | — |
| S21a | | 174,798 | indel | G del | — | — |
| S21b | | 174,986 | SSR(C)n | C ins | — | — |
| S43 | C | 191,822 | SNP | T | C | C |
| S103a | E | 198,461 | indel | 71bp del | — | — |
| S103b | | 198,464 | SNP | — | T | A |
| S107 | F | 200,192 | SSR(A)n | A ins | — | — |
| S306 | G | 230,403 | SSR(AG)n | — | AG del | — |
| S179 | H | 233,798 | SSR(A)n | — | A ins | — |
| S218 | | 253,122 | SSR(C)n | — | C del | — |

Six of these were used in high-resolution mapping. As a result, qLTG-3-1 cosegregated with S103a(E), and a 4.8-kb region was found between the markers SSR118673-13.1(D) and S107(F). A single gene, Os03g0103300, was predicted by RAP-DB (http://rapdb.nig.ac.jp/index.html).

Figure 5:
FIG. 5 shows the amino acid sequence of qLTG-3-1 (SEQ ID NO:112). The mutations shown in the alleles of Hayamasari and Nipponbare are indicated by the sequences. Two domains specified by Pfam (GRP and LTP) have been underlined. The eight carbon residues conserved in the LTP domain are indicated by dots.
Figure 6:
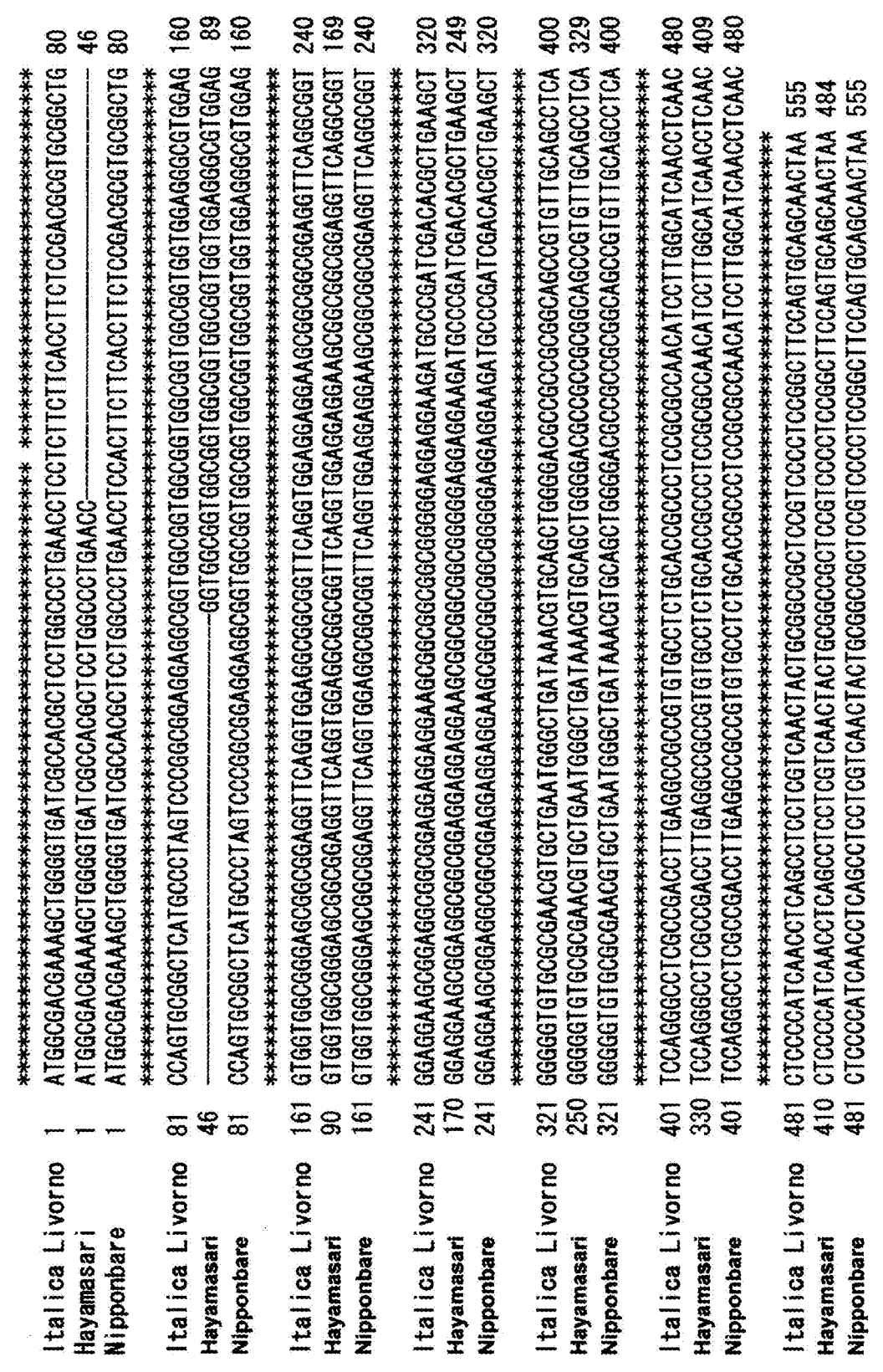

FIG. 5 shows the amino acid sequence of qLTG-3-1. FIGS. 6 and 7 show the nucleotide sequences for qLTG-3-1, and the corresponding amino acid sequences. The sequence for the qLTG-3-1 gene in Italica Livorno had a single exon of 555-bp length. qLTG-3-1 is a single gene in the Nipponbare rice genome. The qLTG-3-1 gene encodes a novel protein of 184 amino acids (FIGS. 5, 6 and 7). From a bioinformatic analysis, the protein of qLTG-3-1 was shown to have two conserved domains (GRP of glycine rich protein family from amino acid 1 to 100 and Tryp_alpha_amyl of protease inhibitor/seed storage/LTP family from amino acid 100 to 182 by Pfam (http://motif.genomo.jp)).

On comparison with the qLTG-3-1 sequence in Italica Livorno, a 71-bp deletion was detected in the coding sequence for Hayamasari. This gave rise to a frame shift that created a stop codon. This fact indicates that the allelomorph (69.7%) exhibited a slightly decreased low-temperature germination rate (p=0.434). The amino acid that was substituted in the Nipponbare allele carried out an important role in the function of the qLTG-3-1 gene, which suggests that the substituted amino acid lowers the gene function.

TABLE 3

Relationships between low temperature germinability and genotype of qLTG-3-1

| Strain | Origin | Germination rate % | Genotype |
|---|---|---|---|
| Yukimaru | Hokkaido | 2.3 | HY |
| Hoshinoyume | Hokkaido | 3.5 | HY |
| Hayamasari | Hokkaido | 10.6 | HY |
| Hakutyoumochi | Hokkaido | 12.3 | HY |
| Kazenokomochi | Hokkaido | 12.4 | HY |
| Matsumae | Hokkaido | 13.5 | HY |
| Hoshitaro | Hokkaido | 14.8 | HY |
| Kitaibuki | Hokkaido | 15.3 | HY |
| Akiho | Hokkaido | 20.2 | HY |
| Hatsusizuku | Hokkaido | 22.5 | HY |

TABLE 3-continued

Relationships between low temperature germinability and genotype of qLTG-3-1

| Strain | Origin | Germination rate % | Genotype |
|---|---|---|---|
| Gimpuu | Hokkaido | 22.5 | HY |
| Onnemochi | Hokkaido | 25.8 | HY |
| Ishikari | Hokkaido | 25.9 | HY |
| Honoka 224 | Hokkaido | 26.7 | HY |
| Kudoumochi | Hokkaido | 29.6 | HY |
| Norin No. 20 | Hokkaido | 34.0 | HY |
| Yukara | Hokkaido | 34.8 | HY |
| Banseieikou | Hokkaido | 36.2 | HY |
| Eiko | Hokkaido | 36.3 | HY |
| Kirara 397 | Hokkaido | 38.5 | HY |
| Sasahonami | Hokkaido | 39.4 | HY |
| Kitahikari | Hokkaido | 46.4 | HY |
| Shiokari | Hokkaido | 49.4 | HY |
| Igoshisoutou | Hokkaido | 51.9 | HY |
| Kamedasoutou (A) | Hokkaido | 52.1 | HY |
| Hayakogane | Hokkaido | 52.2 | HY |
| Michikogane | Hokkaido | 60.8 | HY |
| Nakateeikou | Hokkaido | 68.3 | HY |
| Wasebozu | Hokkaido | 36.0 | IL |
| Chinkomochi | Hokkaido | 51.3 | IL |
| Kurogemochi | Hokkaido | 58.3 | IL |
| Megurosakaemochi | Hokkaido | 64.9 | IL |
| Bozu | Hokkaido | 66.7 | IL |
| Hayayuki | Hokkaido | 67.8 | IL |
| Bozu No. 5 | Hokkaido | 72.3 | IL |
| Sakaemochi | Hokkaido | 82.1 | IL |
| Hashiribouzu | Hokkaido | 82.8 | IL |
| Hokkaiwase | Hokkaido | 83.7 | IL |
| Bozu No. 6 | Hokkaido | 84.1 | IL |
| Bozu No. 1 | Hokkaido | 87.8 | IL |
| Italica Livorno | Italy | 88.9 | IL |
| Akage | Hokkaido | 89.8 | IL |
| Norin No. 11 | Hokkaido | 94.4 | IL |
| Iburiwase | Hokkaido | 95.6 | IL |
| Kitamiakage A | Hokkaido | 96.5 | IL |
| Arroz Da Terra | Portogal | 96.7 | IL |
| Norin No. 33 | Hokkaido | 97.8 | IL |
| USSR22 | Russia | 98.8 | IL |
| Dunghung Shali | Hungary | 100.0 | IL |
| Fukuyuki | Hokkaido | 35.9 | NP |
| Farry | France | 40.3 | NP |
| Tomoemasari | Hokkaido | 52.8 | NP |
| Shinei | Hokkaido | 52.8 | NP |
| Kiyokaze | Hokkaido | 54.5 | NP |
| Sorachi | Hokkaido | 56.4 | NP |
| Hanabusa | Hokkaido | 62.0 | NP |
| Aya | Hokkaido | 66.6 | NP |
| Kitaaki | Hokkaido | 71.3 | NP |
| Kamuimochi | Hokkaido | 73.0 | NP |
| Fukoku | Hokkaido | 74.6 | NP |
| Waseshiroge | Hokkaido | 76.3 | NP |
| Kitakogane | Hokkaido | 76.6 | NP |
| Ishikarishiroge | Hokkaido | 77.3 | NP |
| Waseaikoku | Hokkaido | 82.4 | NP |
| Kyouwa | Hokkaido | 84.4 | NP |
| Wasefukoku | Hokkaido | 86.9 | NP |
| Bozu No. 2 | Hokkaido | 87.8 | NP |
| Suitou Norin No. 15 | Hokkaido | 88.3 | NP |
| Hokuto | Hokkaido | 92.9 | NP |

Example 3

Figure 11:
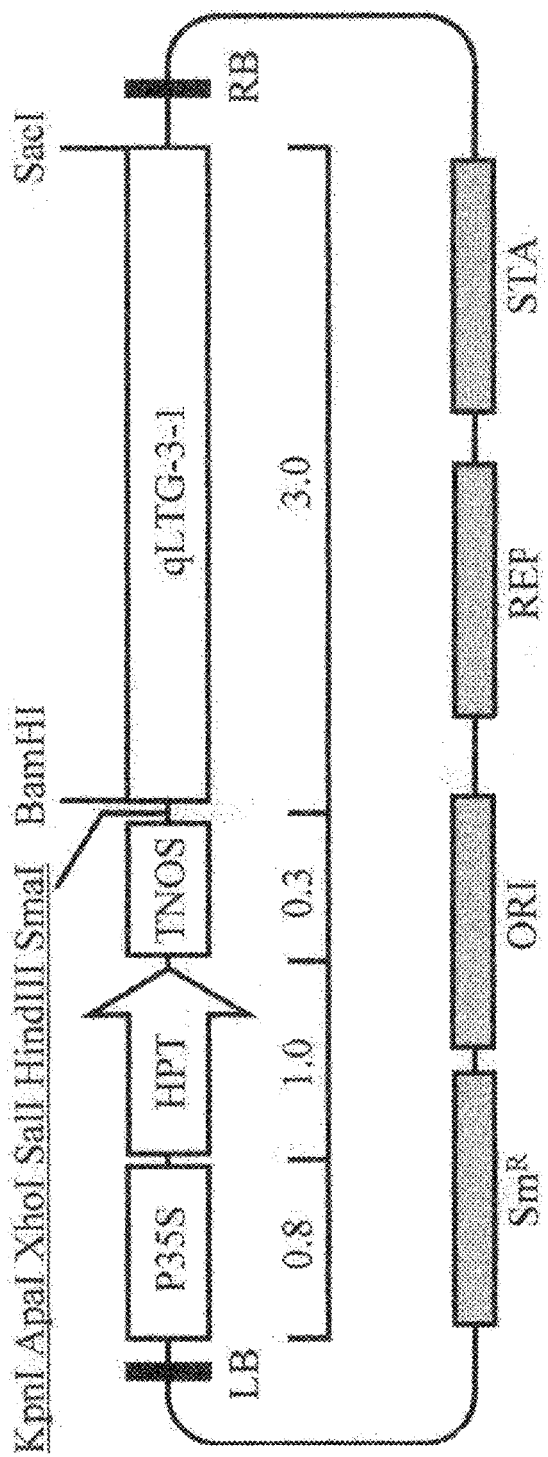
FIG. 11 shows a transgene construct for the complementation testing of qLTG-3-1.

In this example, complementation testing was carried out. A 3-kb genomic DNA fragment of qLTG-3-1 from Italica Livorno was amplified by PCR using the primers Ano13-LA5U and Ano13-LA5L (Table 4). As shown in Table 4, the sequence identifiers in order from left to right are SEQ ID NOs:142-157. This PCR product was cloned at the BamHI/SacI site of the pBluescriptIISK-vector (Stratagene). Next, this fragment was cloned at the pPZP2H-lac Ti-Plasmid vector (Fuse et al., 2001). FIG. 11 shows a transgene construct for complementation testing qLTG-3-1. An Agrobacterium-mediated transformant was used to transform Hayamasari (Toki, 1997; Toki et al., 2006).

TABLE 4

List of the primers for cloning and sequencing

| Category | Forward primer Name | Forward primer Sequence | Reverse primer Name | Reverse primer Sequence |
|---|---|---|---|---|
| Cloning of 3-kb-qLTG-3-1 | Ano13-LA5U | CGCGGATCCCTTCGTAATTC AGCAGGGCCGGGCAAATAA | Ano13-LA5L | AATGAGCTCGTGTTGTGAAAAC AAACAGCTAGTATGTATGTGTG |
| Cloning of the promoter of qLTG-3-1 | ANO13-10U | GTTAAGCTTCTTCGTAATT CAGCAGGGCCGGG | ANO13-10L | CGAGGATCCGCCCACCCACCGC ACTGCACCTG |
| Sequencing | Ano13-6U | TTGCCTCCCGCAGGTATATTA | Ano13-6L | CCAGCTACCACATCACTTAACTAAC |
| | 602U | AGGTTGGTTTTTATGGGACG | LS103UL | GGCTTTTGGTAGCTTAGCTG |
| | S103U | CAGCTAAGCTACCAAAAGCCCA | S103L | TTATCAGCCCATTCAGCACGTT |
| | 51032U | GCTCGCTAGCAGACTTACTTGG | US103LU | AACGTGCTGAATGGGCTGAT |
| | | | 601L | CCGATGGATCGAACAAGAGC |
| | S401U | TGATATATTCTAGTACGATGAATCTGG | S401L | AGACAAACCCTTGATTTCCGTG |
| | S506U | GAACGTGCTGAATGGGCTGATAA | S510L | CGATGGATCGAACAAGAGCTA |

A plant regenerated from a hygromycin-resistant callus (T0 plant) was grown in an isolated greenhouse. T1 plants were obtained from self-fertile T0 plants. The T1 transformants were selected by PCR on the transgene, and the T2 seeds were collected in order to carry out germination experiments.

Figure 12:
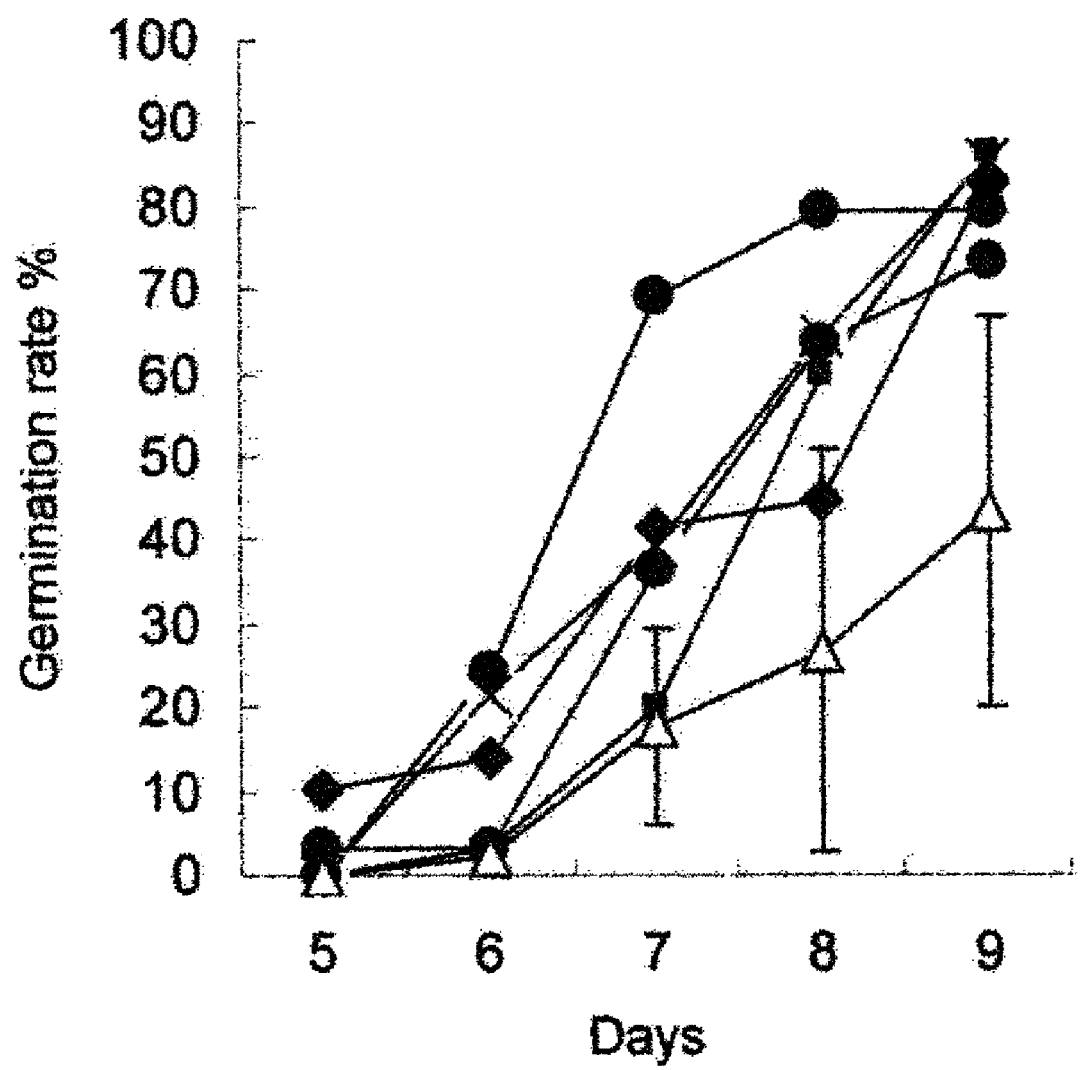
FIG. 12 shows, in the introduction of functional qLTG-3-1 from Italica Livorno to Hayamasari, the germination of homozygous transformants obtained by Agrobacterium-mediated transformation. The germination responses by Hayamasari (open triangles) and five independent transformants (closed symbols) at the low temperature of 15° C., and the germination responses by Hayamasari (open circles), NIL-HYqLTG-3-1 (closed circles) and Italica Livorno (open triangles) at the low temperature of 15° C. are shown. The numerical values represent the mean±standard deviation (SD) for triplicates.

For the sake of complementation testing, a 3-kb fragment of Italica Livorno containing the qLTG-3-1 promoter region and the gene region was introduced into Hayamasari by an *Agrobacterium*-mediated transformant. The transgenic line having the vector exhibited a low temperature germination rate similar to that of Hayamasari. All five transformants that were homozygous for the transgene had higher low-temperature germination rates than Hayamasari (FIG. 12). Differences in germination rate were not observed among these lines at the optimal germination temperature of 25° C. As a result, the gene in the 3-kb fragment of Italica Livorno was confirmed to enhance low temperature germination.

Example 4

In this example, the expression of the qLTG-3-1 gene was studied. Using RNAiso (TAKARA), the total RNA was extracted from each organ of rice and treated with DNaseI (TAKARA). For Northern blot analysis, the total RNA (4 μg/sample) was separated on 2.0% (w/v) agarose-modified formaldehyde gel containing 40 mM of MOPS (pH 7.0), 10 mM of sodium acetate and 2% (v/v) formaldehyde.

The RNA was blotted with 20×SSC to a positively charged nylon membrane (Roche Diagnostics). Hybridization and signal detection were carried out with a DIG system and CDP-Star (Roche Diagnostics) according to the manufacturing guidelines. The PCR fragments obtained from the primers 13-5U and 13-5L were used as the probes for Northern blot analysis (Table 5). As shown in Table 5, the sequence identifiers in order from left to right are SEQ ID NOs:158-173.

TABLE 5

List of the primers for RT-PCR analysis and probe for Northern blot analysis

| Category | Gene Name | RAP locus | Forward primer Name | Forward primer Sequence | Reverse primer Name | Reverse primer Sequence | Anneal Temp. (° C.) | No. of cycle | Size (bp) | Reference |
|---|---|---|---|---|---|---|---|---|---|---|
| Dormancy/ABA-related | OsPKABA1 | Os07g0622000 | PKABA1-1U | ATGTGATGCTT GTTGGTGCGTA | PKABA1-1L | TTGATGTCGTT CATCTGGACG | 55 | 30 | 274 | This study |
| | OsAB13/Vp1 | Os01g0911700 | Vp1-4U | TTCCTGCTGCA GAAGGTGCTGA A | Vp1-4L | GAGCCATGCTT ATGCTTACCTA | 60 | 30 | 371 | This study |
| | OsPER1 | Os07g0638300 | PER1-2U | AAGATCCGCAT CCACGACTTC | PER1-2L | GTTCAGCTGCT TGATGGCCTC | 60 | 25 | 273 | This study |
| GA-biosynthesis | OsCPS1 | Os02g0278700 | OsCPS1-1U | ACGAATTGAGG AGGCAGCATCT ATG | OsCPS1-1L | GAGCAAGTTCT TGCATACCCAA CTC | 60 | 38 | 182 | Sakamoto et al. (2004) |
| | OsKS1 | Os040611800 | OsKS1-1U | GACAAGGGACC AGCTCCAGACA TTGGAC | OsKS1-1L | CAGGAGCAGCA ATCTGCTCATC CATGGC | 60 | 38 | 323 | Sakamoto et al. (2004) |
| | OsKO2 | Os06g0570100 | OsKO2-1U | ATTTCTTCCCC TACCTCAGCTG GTTCC | OsKO2-1L | CTCTATGAGTG CCTCCCACACT AGCATC | 60 | 28 | 221 | Sakamoto et al. (2004) |
| | OsKAO | Os06g0110000 | OsKAO-1U | GAGATCGTCGA CGTCCTCATCA TGTACC | OsKAO-1L | AGATGTTGACG CAGCGAAGTGT CTCGTC | 60 | 33 | 241 | Sakamoto et al. (2004) |
| | Osa420ox1 | Os03g0856700 | OsGA20ox1-1U | GCTGTCGTTCC GGTACTCATC | OsGA20ox1-1L | TGGAAGAATCG CCGGAAGTAGT | 60 | 33 | 222 | This study |
| | OsGA20ox2 | Os01g0883800 | OsGA20ox2-1U | GCTGACGATCA TGGAACTCCT | OsGA20ox2-1L | TCTTATACCTC CCGTTCGACA | 60 | 33 | 305 | This study |
| | OsGA20ox3 | Os07g0169700 | OsGA20ox3-1U | AAGGAGACCAT GTCGTTCAACT | OsGA20ox3-1L | TAGTGGTTCAG CCGCATCACCG | 60 | 33 | 223 | This study |
| | OsGA20ox4 | Os05g0421900 | OsGA20ox4-3U | TCCACCGTCGC CGATTACTTCT C | OsGA20ox4-3L | TCCTCGAAGAA CTCCCTGTAGT AT | 60 | 33 | 225 | This study |
| | OsGA3ox1 | Os05g0178100 | OsGA3ox1-1U | AGGAGTACGAC TCGTCGATGAG AG | OsGA3ox1-1L | ATGAAGGTGAA GAAGCCTGAGT | 60 | 33 | 167 | This study |
| | OsGA3ox2 | Os01g0177400 | OsGA3ox-1U | TCCTTCTTCTC CAAGCTCATGT | OsGA3ox-1L | CGAAGGTGAAG AAGCCCGAGT | 60 | 33 | 346 | This study |
| | OsGA2ox1 | Os05g0158600 | OsGA2ox1-1U | TTTTCGTCAAT GTTGGTGATGT C | OsGA2ox1-1L | TATGCTTTTCC CTCACTGGCAT | 60 | 33 | 307 | This study |
| | OsGA2ox2 | Os01g0209700 | OsGA2ox2-1U | TCGAGTACCTG CTACTCTGCCT | OsGA2ox2-1L | TAGTGGTTCAC CCTGAGGATGG A | 60 | 33 | 213 | This study |
| | OsGA2ox3 | Os01g0757200 | OsGA2ox3-1U | AGGTGTTCCGC GTGAACCACTA C | OsGA2ox3-1L | GAAACCCTAGA CTTTAGGCTGT TG | 60 | 33 | 286 | This study |
| | OsGA2ox4 | Os05g0560900 | OsGA2ox4-1U | CCACAGATCAT CTCCGTGCTCA G | OsGA2ox4-1L | TTCTTGTACTC CCCCCAGGTGA A | 60 | 33 | 284 | This study |
| | OsGATA1 | Os02g0806400 | OsGATA1-1U | AGGTGTTCGAC CGCAAGGACG | OsGATA1-1L | GAGGAGGAGCC CCCATTGGTT | 55 | 30 | 286 | This study |

TABLE 5-continued

List of the primers for RT-PCR analysis and probe for Northern blot analysis

Figure 13:
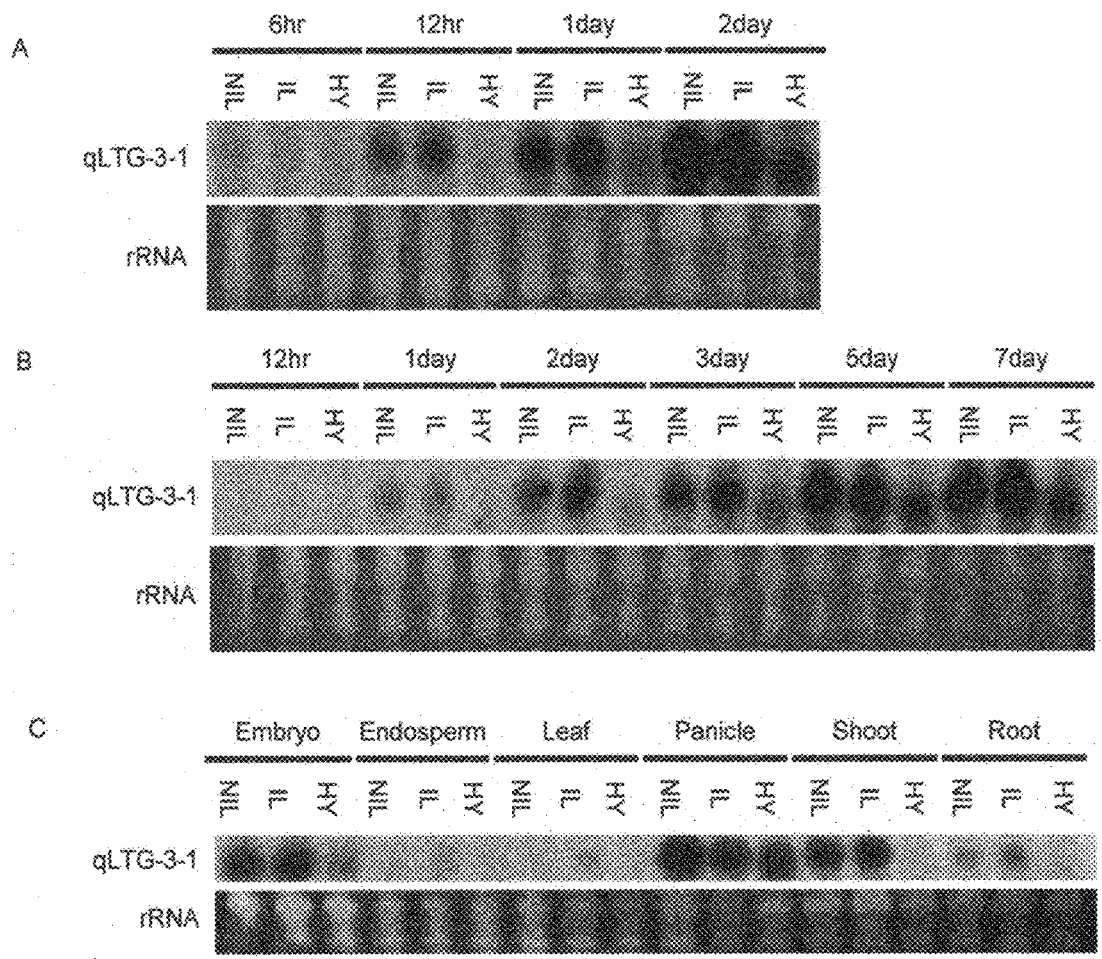
FIG. 13 shows the expression of the qLTG-3-1 gene. Northern blot analysis was used to measure the expression level of the qLTG-3-1 gene in the total RNA extracted from different tissues of Hayamasari (HY), NILHYqLTG-3-1 (NIL), and Italica Livorno (IL). Ethidium bromide-stained rRNA was used as the control. (A) is the germination at 30° C., (B) is the germination at 15° C., and (C) is the tissue specificity.

| Category | Gene Name | RAP locus | Forward primer Name | Forward primer Sequence | Reverse primer Name | Reverse primer Sequence | Anneal Temp. (° C.) | No. of cycle | Size (bp) | Reference |
|---|---|---|---|---|---|---|---|---|---|---|
| Amylase | OsGAMYB | Os01g0812000 | OsGAMYB-3U | AAGATGGGAACAAGTGGGCT | OsGAMYB-3L | TAGAAACGGCTGAAAGATGTGG | 55 | 30 | 307 | This study |
|  | Ramy1A | Os02g0765600 | Ramy1A-1U | ATTCAACTGGGAGTCGTGGAA | Ramy1A-1L | TCGAAGAGGCAGTAGATGCCG | 60 | 30 | 306 | This study |
| Isoprenoid biosynthesis | OsDXS1 | Os05g0408900 | OsDXS1-1U | AGGTAGGCAAAGGGAGGGTA | OsDXS1-1L | CCACGAACAACTGAAGAGCA | 60 | 30 | 592 | This study |
|  | OsDXS2 | Os07g0190000 | OsDXS2-1U | TCCAAATGCAAAATGATAATGG | OsDXS2-1L | AGGGAACTGAGTTTGTATGTATGTAG | 50 | 30 | 249 | This study |
|  | OsDXS3 | Os06g0142900 | OsDXS3-1U | GTTGTGCAGCAAGTTTGAGC | OsDXS3-1L | TCATTCAGAGAGGATTCACTGC | 50 | 30 | 392 | This study |
|  | OsDXR/IspC | Os01g0106900 | OsDXR/IspC-1U | CAAGGTGGTGGAGCTGACAT | OsDXR/IspC-1L | CGCAAACATATTTGATTCTTCC | 55 | 30 | 391 | This study |
|  | OsCMS/IspD | Os01g0887100 | OsCMS/IspD-3U | GTCTCGGTGGTGCTCTTGTC | OsCMS/IspD-3L | ACACTAAGGGCCTFGCAGAA | 55 | 30 | 322 | This study |
|  | OsCMK/IspE | Os01g0802100 | OsCMK/IspE-1U | TCAGTTTCTGACTGAGGGAGTG | OsCMK/IspE-1L | AACAGTTTTGCAGGGAGGA | 57.5 | 30 | 295 | This study |
|  | OsMCS/IspF | Os02g0680600 | OsMCS/IspF-1U | AGCTGGGAACCTAGACG | OsMCS/IspF-1L | CCCTAAAATTTCAGTGATAAACCA | 50 | 30 | 300 | This study |
|  | OsHDS/IspG | Os02g0603800 | OsHDS/IspG-1U | TGCTGATTTCGGATACGTTG | OsHDS/IspG-1L | CACTGATTTCAGGACGCTTCT | 60 | 30 | 359 | This study |
|  | OsHDR/IspH | Os03g0731900 | OsHDR/IspH-1U | AACTCCGGACAAGGTTGTTG | OsHDR/IspH-1L | ACAGGGAGTCCTGCATTTGA | 60 | 30 | 393 | This study |
| Control | UBQ2 | Os02g0161900 | rubq2-3'UTR-F | GTCTGATCTTCGCTGGCAAGCAGC | rubq2-3'UTR-R | GCATACTGCTGTCCCACAGGAAACTG | 63 | 25 | 271 | Yang et al. (2005) |
| qLTG-3-1 | qLTG-3-1 | Os03g0103300 | 13-5U | TGCTGAATGGGCTGATAAAC | 13-5L | ATGCAGAAAAGACGAGATGCAG | 60 | 33 | 549 | This study | qTLG-3-1 was germination treated by Northern blot analysis with Italica Livorno and NILHYqLTG-3-1 at 30° C. and 15° C. in each case, after which expression by the gene occurred at 12 hours and 1 day. Expression increased further with the start of germination (FIGS. 13A and B). The pattern of increase in the expression level was the same at both 30° C. and 15° C. This fact indicates that qLTG-3-1 is not induced by a low temperature stress. The expression level in Hayamasari was lower than in Italica Livorno and NILqLTG-3-1. Also, the induction of expression was delayed in Hayamasari. The expression patterns in the three varieties corresponded well with their low temperature germination phenotypes. The expression of qLTG-3-1 was tissue-specific (FIG. 13C). Expression was not detected in the endosperm and leaves. Low-level expression was detected in the roots. Strong expression was detected in seed embryos at the time of germination, and in the above-ground parts and young panicles of seedlings.

Example 5

A physiological assessment of qLTG-3-1 was carried out in this example. Germination tests were carried out by the method reported by Fujino et al. (2004). For the low temperature stress, seeds on a Petri dish were placed in an incubator. Solutions of plant hormone (ABA and GA) and mannitol at different concentrations were added to the Petri dishes at this time before placing the dishes in the incubator.

Figure 14:
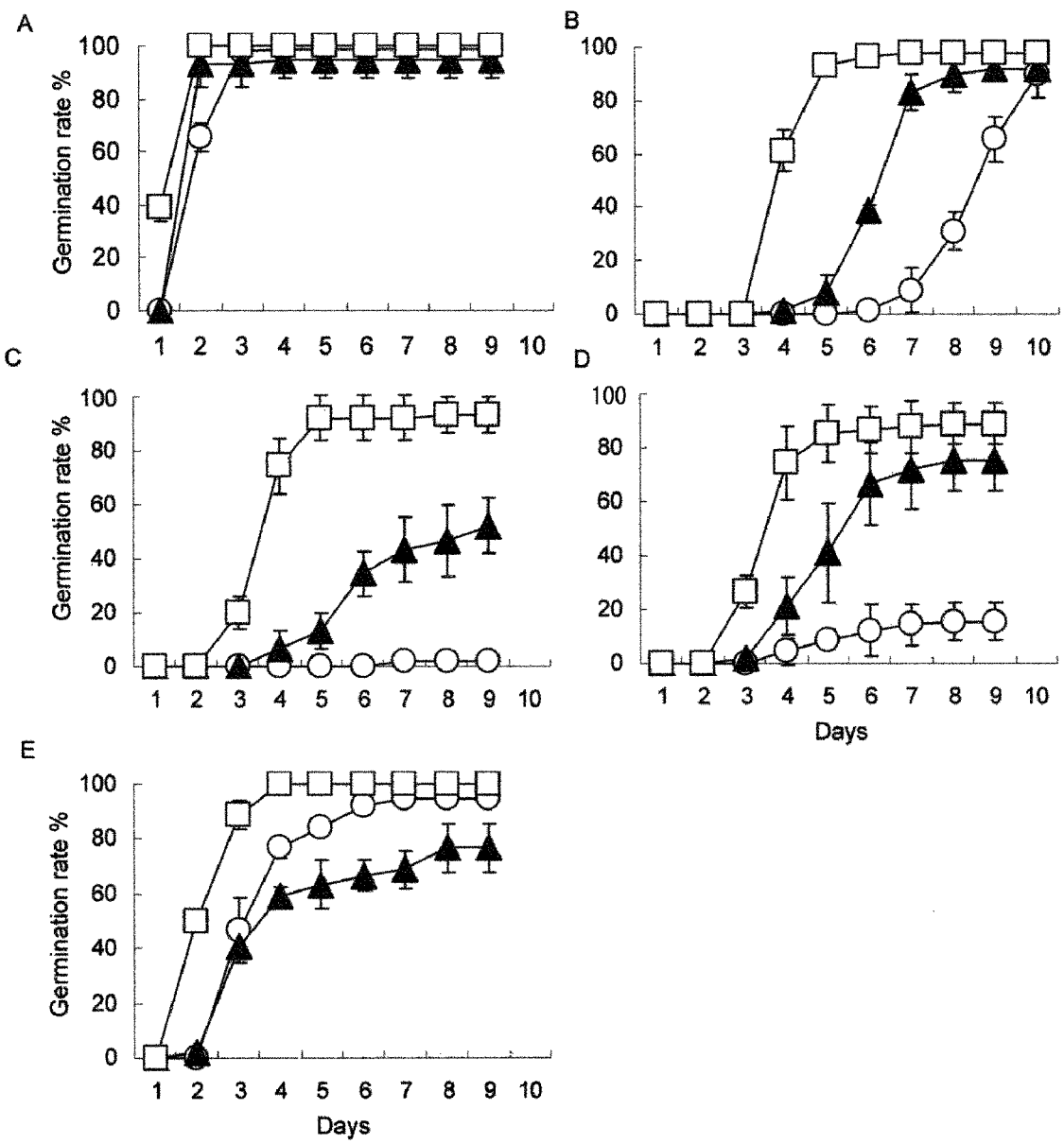
FIG. 14 shows the germination response of qLTG-3-1 under different stress conditions. (A) is the germination at the optimal temperature of 25° C., (B) is the germination at 13° C., (C) is the sensitivity to NaCl (300 mM), (D) is the sensitivity to mannitol (500 mM), and (E) is the sensitivity to ABA (500 mM). Examples of Hayamasari (open circles), NIL-HYqLTG-3-1 (closed triangles), and Italica Livorno (open circles) are shown. The numerical values represent the mean±standard deviation (SD) for triplicates.
Figure 15:
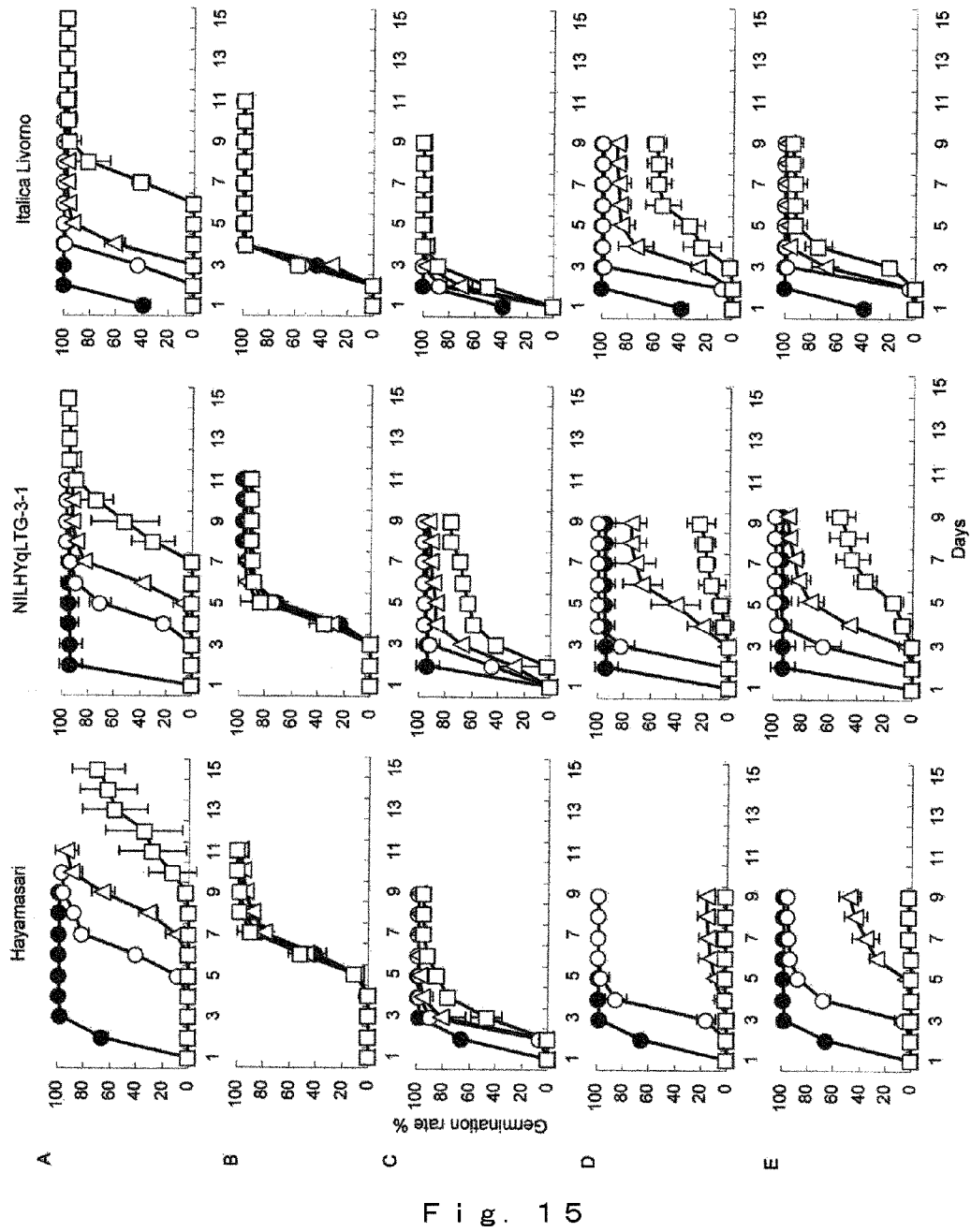
FIG. 15 shows the germination responses of Hayamasari, NILHYqLTG-3-1 and Italica Livorno under different stress conditions. In (A), the seeds were incubated in water at 25° C., 15° C., 13° C. and 10° C. In (B), GA (100, 200, 500 µM) was added at 15° C.; in (C), ABA (200, 300, 500 mM) was added at 25° C.; in (D), NaCl (150, 250, 300 mM) was added; and in (E), mannitol (250, 500, 600 mM) was added, following which incubation was carried out. The open circles indicate controls. The low concentrations to high concentrations are indicated by, in order, open circles, triangles and squares.

Endogenous ABA and GA play a major role in promoting seed dormancy and germination (Leung and Girandat, 1998). qLTG-3-1 was studied to determine whether it influences the responses to ABA and GA in the germination period. FIG. 14 shows the germination responses by qLTG-3-1 under different stress conditions. FIG. 15 shows the germination responses by Hayamasari, NILHYqLTG-3-1 and Italica Livorno under different stress conditions.

At the optimal temperature (25° C.), very slight differences in germination rate were observed between Hayamasari, Italica Livorno and NILHYqLTG-3-1 (FIG. 14A). In ABA treatment, a delay in germination was observed in both parents, but NILHYqLTG-3-1 exhibited a lower germination rate. At ABA concentrations below 300 mM, NILHYqLTG-3-1 showed a delay in germination similar to that in the parents (FIG. 15). At an ABA concentration of 500 mM, the sensitivity to ABA was higher than in the parents (FIG. 14).

Figure 16:
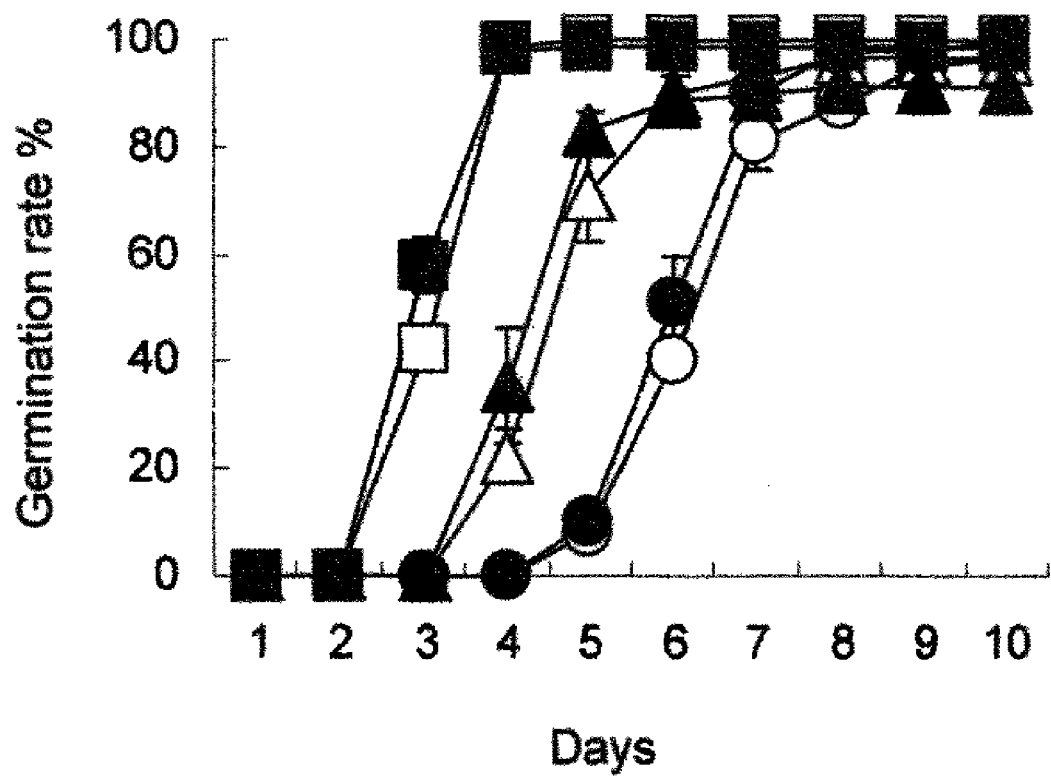
FIG. 16 shows the effects of GA (500 mM) on the germination response at 15° C. The open and closed symbols represent, respectively, the presence and absence of GA. Hayamasari, NILHYqLTG-3-1 and Italica Livorno are represented by, respectively, circles, triangles, and squares.

At concentrations lower than 250 mM mannitol and 150 mM NaCl, all the varieties showed a delay in germination (FIG. 15). However, at 300 mM NaCl and at 500 mM mannitol and 13° C., NILHYqLTG-3-1 had improved germination compared with Hayamasari (FIG. 14). From these results, qLTG-3-1 exhibited a correlation with the responses to various stresses, including low temperature, salt and osmotic pressure. Also, exogenous GA did not promote seed germination in any of the genotypes (FIG. 16).

Example 6

In this example, the association between qLTG-3-1 expression and seed germination was examined. Total RNA (0.5 μg) was reverse-transcripted by means of ReverTra Ace (TOYOBO) having an Oligo(dT)$_{20}$ primer, according to the manufacturing guidelines. PCR reactions were carried using KOD-Plus (TOYOBO). Each PCR reaction (10 μL) included 0.5 μL of cDNA template that had been diluted 5-fold. The specificity of each primer for the target gene was confirmed by sequencing the PCR product. The primer and amplification conditions for RT-PCT analysis are shown in Table 5.

Figure 17:
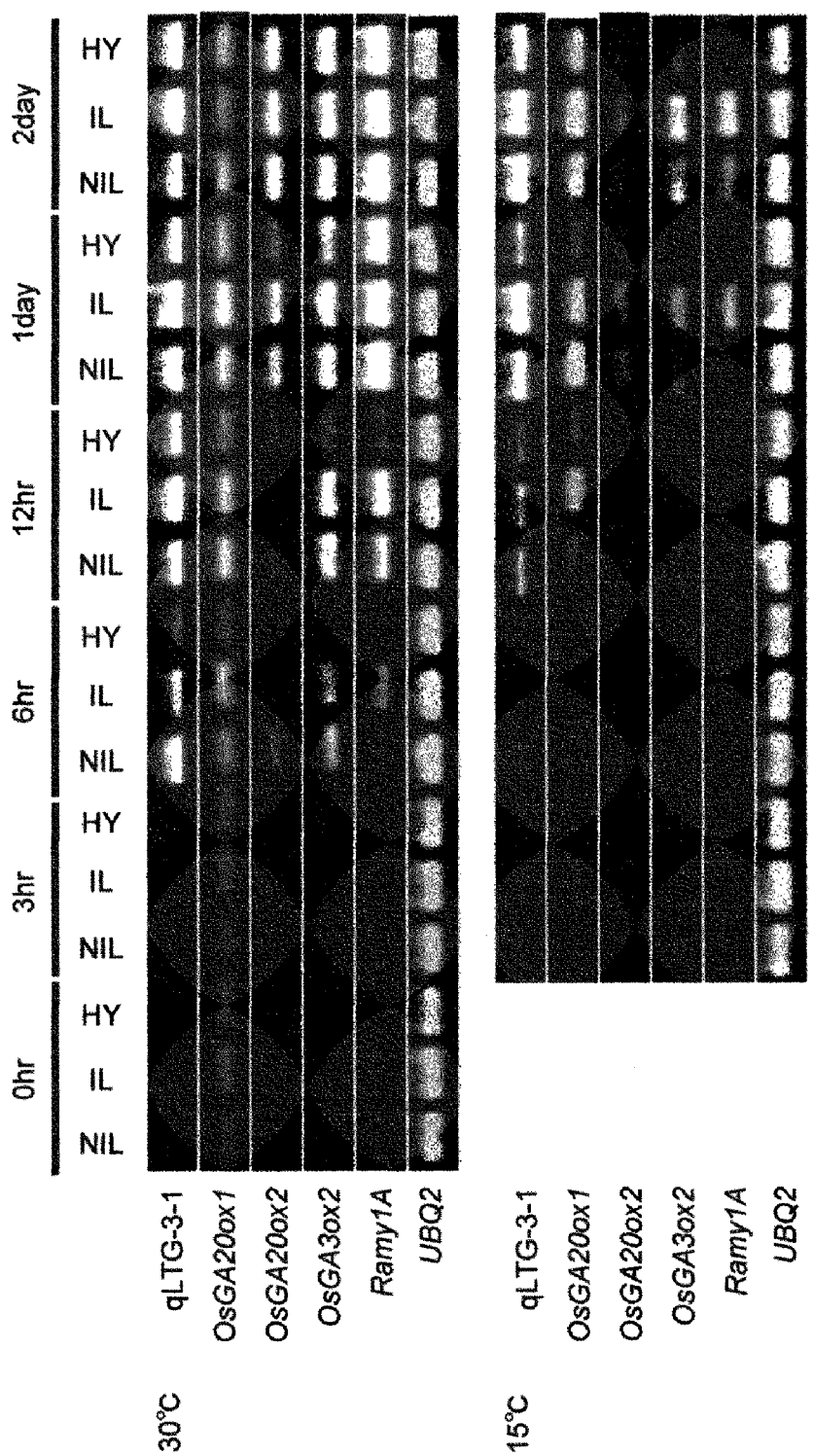
FIG. 17 shows the expression of qLTG-3-1, GA photosynthesis and amylase genes in the period of germination at 30° C. and 15° C., based on RT-PCR analysis. Ubi2 was used as the control in the RT-PCR experiment.
Figure 18:
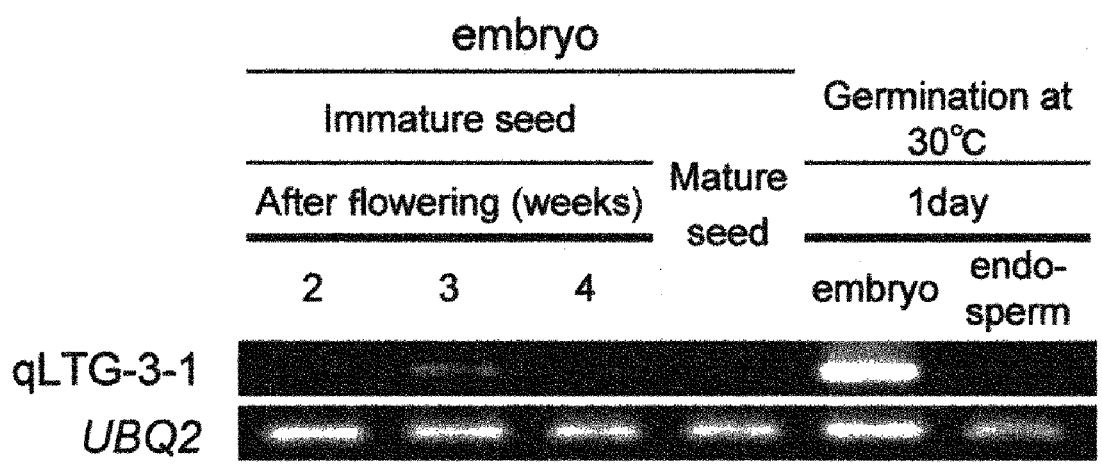
FIG. 18 shows the expression of qLTG-3-1 in seeds during seed germination and in endosperm during germination, based on RT-PCR analysis. Ubi2 was used as the control in the RT-PCR experiment.

The expression of qLTG-3-1 in embryos at the time of Italica Livorno, Hayamasari and NILHYqLTG-3-1 seed germination was determined by RT-PCR analysis. As shown in FIG. 17, qLTG-3-1 expression was detected in Italica Livorno and NILHYqLTG-3-1, both 6 hours and 12 hours after treatment at 30° C. and 15° C., promoting the start of germination. During ripening of the seed after flowering, the expression of qLTG-3-1 was at a very low level in the embryo (FIG. 18).

Figure 19:
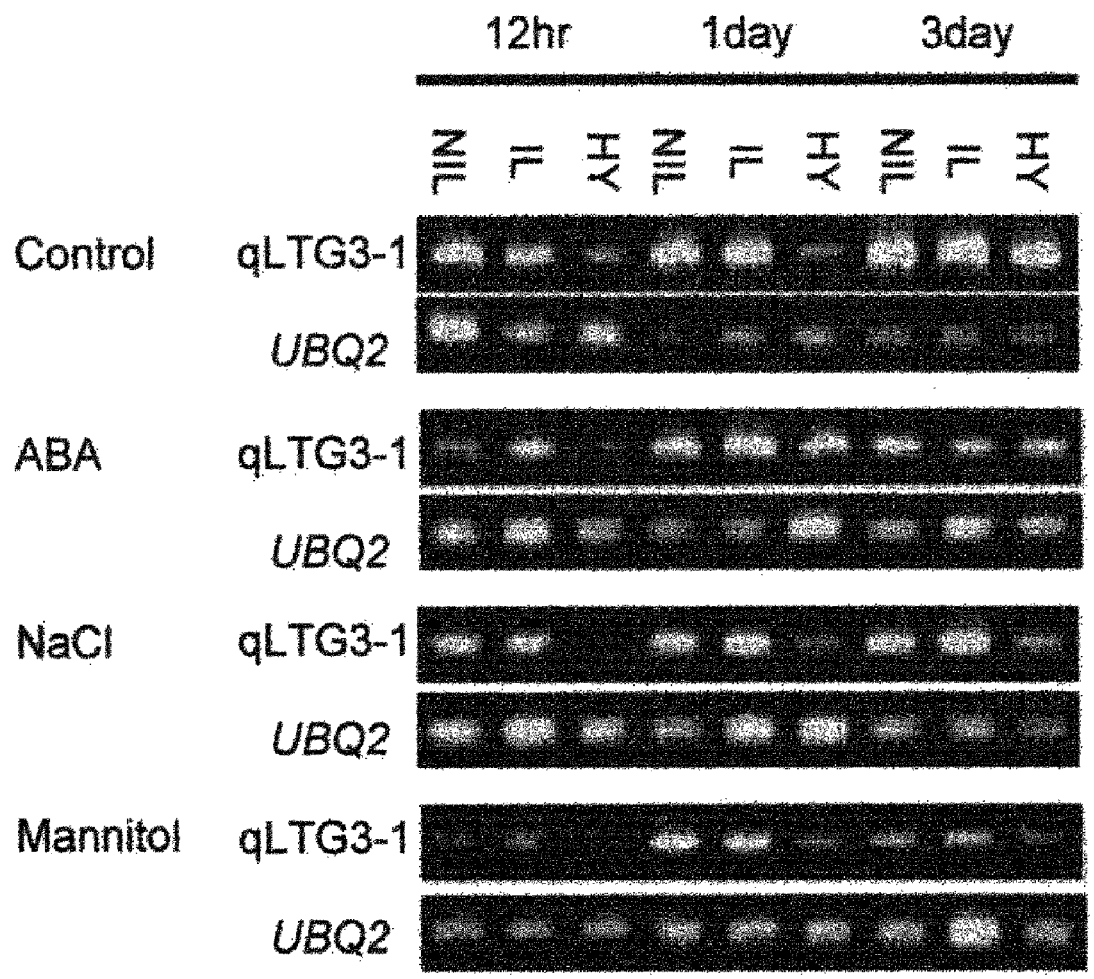
FIG. 19 shows the expression of qLTG-3-1 during germination when treated with ABA (500 mM), NaCl (300 mM) and mannitol (500 mM), based on RT-PCT analysis. Ubi2 was used as the control in the RT-PCR experiment.

The qLTG-3-1 expression pattern was investigated in embryos treated with ABA (500 mM), NaCl (250 mM) and mannitol (500 mM). The delay and suppression of qLTG-3-1 expression was observed (FIG. 19) under all the stress conditions. These phenomena correlated well with the inhibition and delay of germination phenotypes under these stresses.

Example 7

In this example, a histochemical analysis of qLTG-3-1 expression was carried out. To create a qLTG-3-1 promoter-GUS gene fusion construct, a 2-kb genomic DNA fragment of the 5' upstream region of qLTG-3-1 from Italica Livorno was amplified by PCR using the primers Ano13-10U and Ano13-10L (Table 4).

Because a promoter sequence that fully expresses the true qLTG-3-1 gene is unknown, a 2-kb 5' upstream region from the initiation codon of qLTG-3-1 was used as the promoter. This PCR product was cloned to the HindIII/BamHI site of the pBluescript II SK vector (Stratagene). Next, this fragment and the GUS gene were cloned to the pPZP2H-lac Ti-plasmid vector (Fuse et al., 2001). The qLTG-3-1::GUS construct is shown in FIG. 20.

An *Agrobacterium*-mediated transformant was used to transform Hayamasari (Toki, 1997; Toki et al., 2006). Plants regenerated from hygromycin-resistant calluses (T0 plants) were grown in an isolated greenhouse. Self-fertile seeds of each T0 plant (T1) were used in this experiment. The T0 transformants were screened for transgenes by PCR.

To carry out the histochemical analysis of GUS expression, the seeds of transgenic plants containing the qLTG-3-1::GUS construct were incubated at 30° C. Under these conditions, germination and the emergence of the coleoptile began to arise in a very small proportion of the seeds one day after treatment. The seeds of the transformants were furnished for testing 0, 1 and 2 days after treatment.

All the seeds of the transformant and longitudinally cut seeds were vacuum immersed in 50 mM of $NaH_2PO_4$ (pH 7.0) containing 0.5 mM X-Gluc, 0.5 mM $K_3[Fe(CN)_6]$, 0.5 mM $K_4[Fe(CN)_6]$ and 0.5% (v/v) Triton X-100, and incubated at 37° C. for 6 hours. Next, 70% EtOH was added thereto to stop the enzyme reaction under the temperature.

Figure 21:
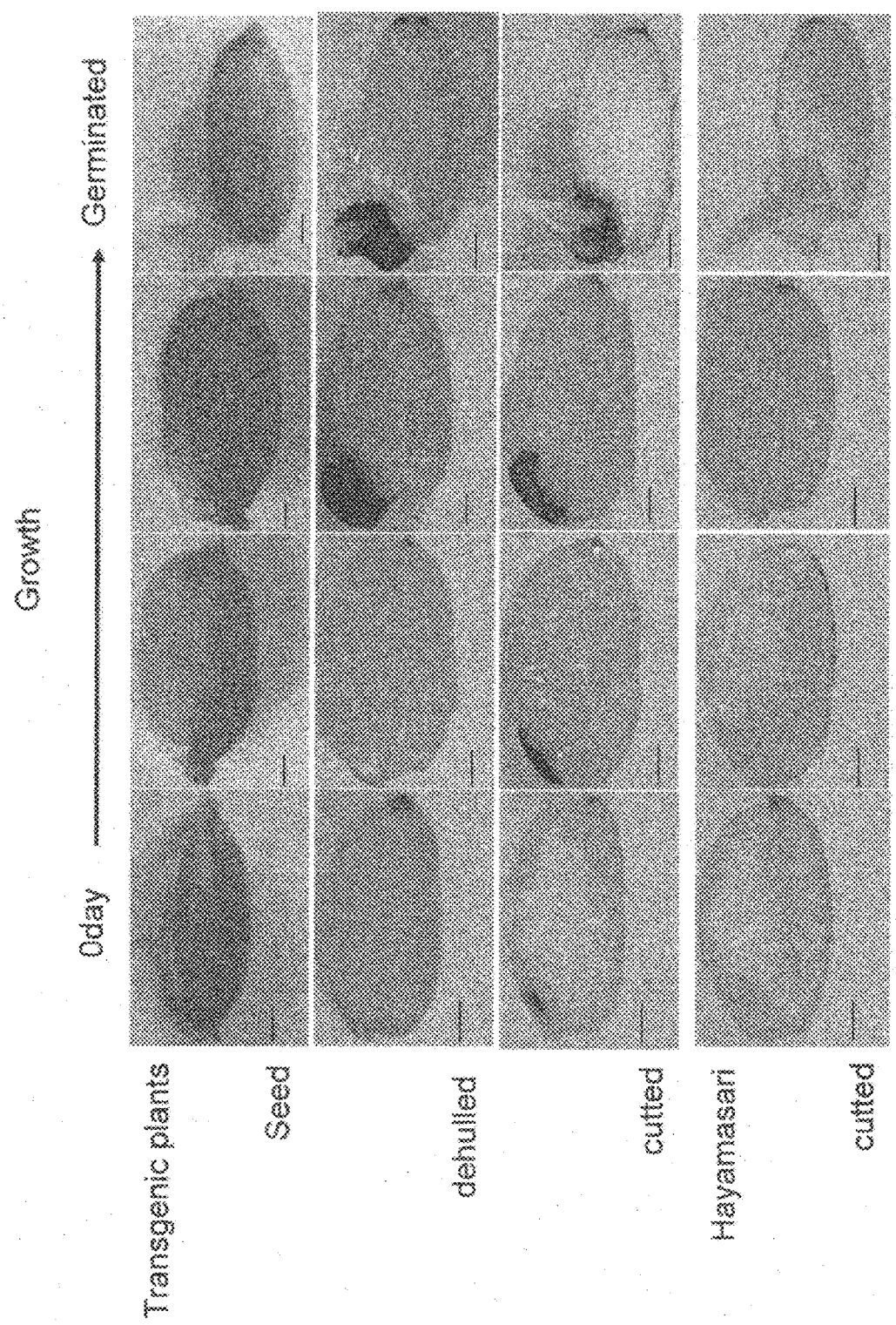
FIG. 21 shows the GUS expression under qLTG-3-1 gene promoter control. The transformant that expresses GUS under control by a 2-kb upstream region of qLTG-3-1 serving as the promoter was stained for the GUS activity. Hayamasari, which is a non-transgenic plant, did not exhibit background GUS activity. The bar represents 1 mm.

The qLTG-3-1 promoter activity in transgenic rice plants having the qLTG-3-1::GUS (beta-glucuronidase) reporter-gene fusion construct was analyzed. GUS expression was strongly detected in the bud scales and ventral scales surrounding the seminal roots (FIG. 21). In Hayamasari plants that were not transformants, signals were not detected. Based on Northern blot analysis, RT-PCR analysis and GUS reporter expression, the qLTG-3-1 genes were strongly expressed in the embryos at the time of seed germination.

Example 8

In this example, the induction of GA biosynthesis gene and Ramy 1A expression by qLTG-3-1 was examined. It is not clear whether qLTG-3-1, which is strongly expressed in embryos at the time of seed germination, exhibits a high germination rate under diverse stress conditions. To assess the function of qLTG-3-1, the expression profiles of six GA biosynthesis genes and the α-amylase gene Ramy 1A, which are known to be important for seed germinability, was determined by semi-quantitative RT-PCR in embryos during the period of seed germination. The expression of OsGA20ox3, OsGA20ox4 and OsGA3ox1 was not detected in this experiment.

The qLTG-3-1 gene clearly induced the expression of OsGA20ox1, OsGA20ox2, OsGA3ox2 and Ramy 1A, all of which have expression patterns similar to that of qLTG-3-1 (FIG. 17). The expression of OsGA20ox1 and of OsGA3ox2 were detected at 6 and 12 hours following treatment at, respectively, 30° C. and 15° C. This time was the same as that for qLTG-3-1. The expression of OsGA20ox2 was delayed relative to that of the other genes (FIG. 17). Next, the expression of Ramy 1A was examined.

Figure 22:
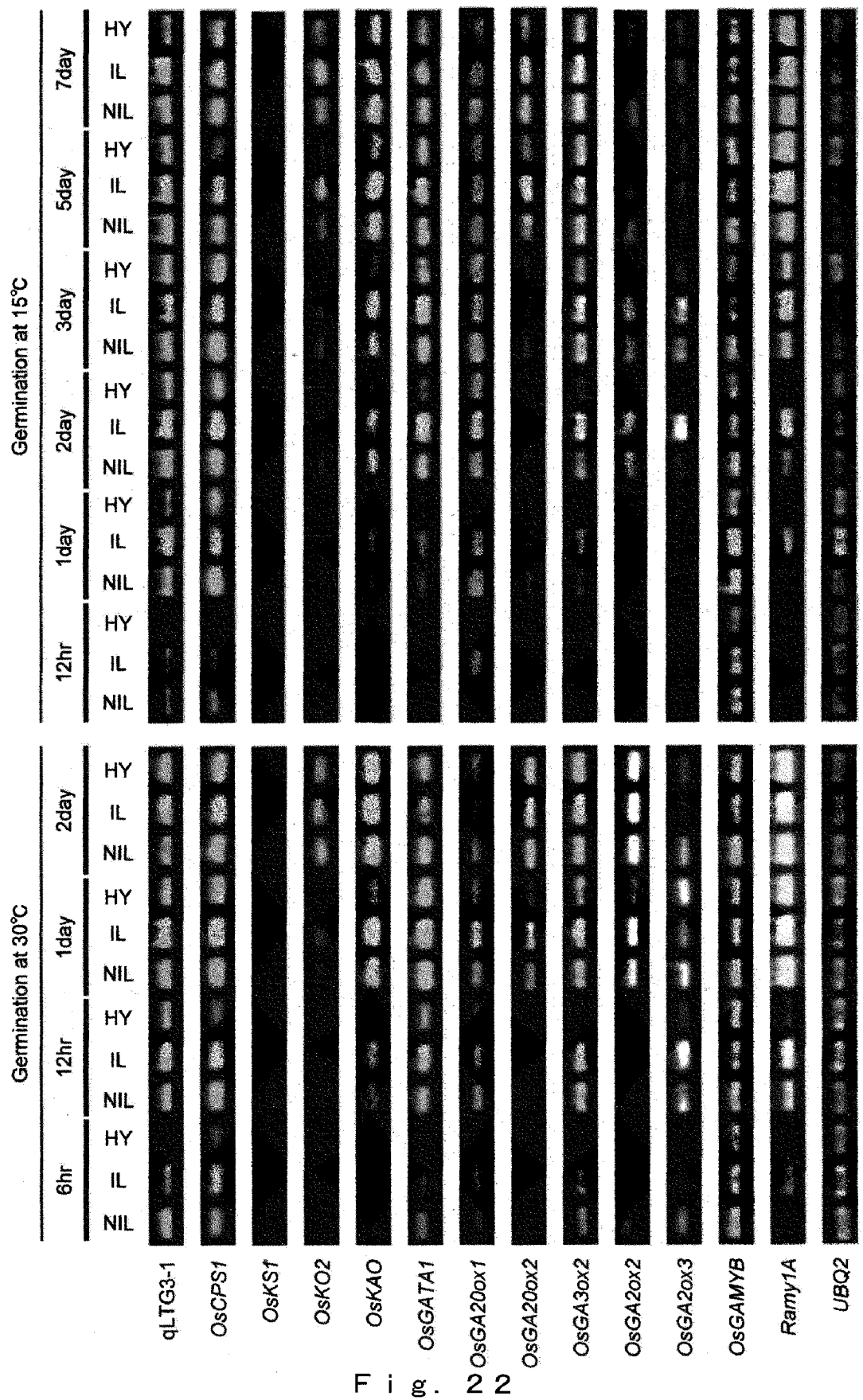
FIG. 22 shows the expression of the qLTG-3-1, GA biosynthesis and amylase genes in the period of germination at 30° C. and 15° C., based on RT-PCR analysis. Ubi2 was used as a control in the RT-PCR experiment.

Expression delays in all the tested genes were examined in Hayamasari. Italica Livorno and NILHYqLTG-3-1 showed the same expression patterns, which suggests that the expression of these genes in GA biosynthesis and Ramy 1A is induced by qLTG-3-1. In addition, the expression of eight genes for GA biosynthesis and amylase was determined (Table 5, FIG. 22). The expression of six of these is highly controlled by qLTG-3-1, which suggests that qLTG-3-1 induces GA biosynthesis.

Example 9

Figure 23:
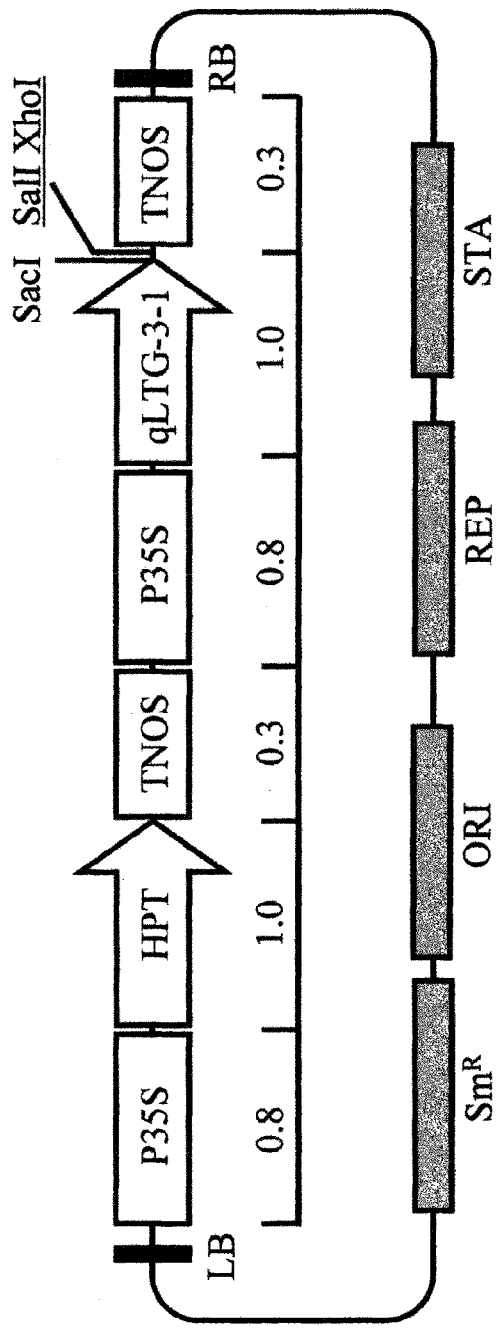
FIG. 23 shows a construct for qLTG-3-1 overexpression.

In this example, the overexpression of qLTG-3-1 was carried out. To create overexpressing plants, a construct of the 35S promoter which drives qLTG-3-1 was created. PCR product amplified using the primers Ano13-LA5U and Ano13-LA5L (Table 4) was digested with BamHI and SacI. These fragments were cloned to the SacI site of the pPZP2Ha3 Ti-Plasmid vector (Fuse et al, 2001). FIG. 23 shows the construct for overexpression of qLTG-3-1.

Figure 24:
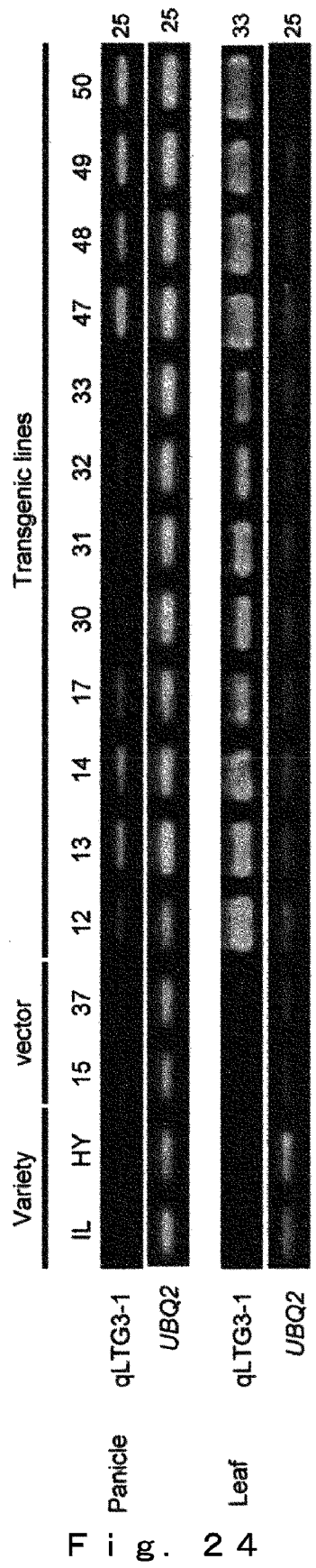
FIG. 24 shows the expression of qLTG-3-1 in an overexpressed transgenic plant, based on RT-PCR analysis. Ubi2 was used as the control in the RT-PCR experiment.
Figure 25:
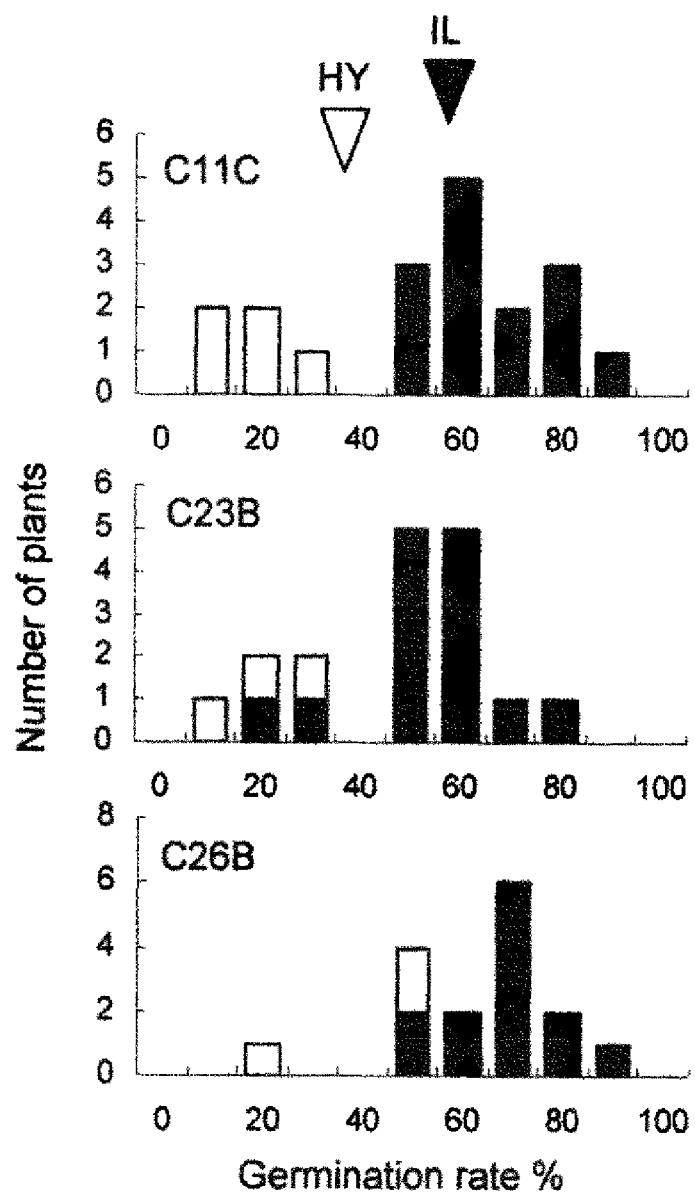
FIG. 25 shows the low temperature germinability of an overexpressed transgenic plant. The frequency distributions of low temperature germinability in three independent populations of T1 individuals are shown. The black and white bars indicate the presence or absence of transgenes.

An *Agrobacterium*-mediated transformant was used to transform Hayamasari (Toki, 1997; Toki et al., 2006). Plants regenerated from hygromycin-resistant calluses (T0 plants) were grown in an isolated greenhouse. Self-fertile plants of each T0 plant (T1) were grown. The T1 transformants were screened by PCR for transgenes and cultivated to obtain T2 plants, which were collected in order to carry out germination experiments.

qTLG-3-1 has a tissue-specific expression. In order to examine the effects of expression pattern, tissue specificity and amount on germination in the plant and on regulation of the stress response, overexpressed plants in which the qLTG-3-1 is driven by the 35S promoter were created. In transgenic plants, qLTG-3-1 was strongly expressed in the leaves and panicles; however, expression was not detected in nontransgenic plants (FIG. 24). These overexpressed plants exhibited a high low-temperature germination rate (FIG. 25). Segregation analysis of the low temperature germination rate was carried out based on the presence or absence of the transgene in three independent populations of T1 individuals. Plants having the transgene exhibited a higher low-temperature germination rate than plants without it. These results showed that the overexpression of qLTG-3-1 increases the low-temperature germination rate.

Example 10

In this example, the DNA polymorphism in the qLTG-3-1 gene within cultivated rices and wild varieties was examined. The seeds of a core collection of cultivated rice (*O. sativa*) containing 62 varieties (Kojima et al., 2005) were acquired from the National Institute of Agrobiological Sciences. This collection was composed of three groups, Groups A, B and C, which correspond respectively to *Japonica*, *Aus* and *Indica* from a wide region (Kojima et al., 2005; Garris et al., 2005).

Rice seed of the AA genome wild species W0106 (*O. rufipogon*), W0652 (*O. barthii*), W1169 (*O. glumaepatula*), W1413 (*O. longistaminata*) and W1508 (*O. longistaminata*) were acquired from the National Institute of Genetics of the Research Organization of Information and Systems. The total DNA was isolated from young leaves using the CTAB method described by Fujino et al. (2004).

The qLTG-3-1 gene was amplified using primers (Table 4), then directly sequenced using cycle sequencing with a Big Dye Terminator (Applied Biosystems). Sequencing was carried out with a Prism 3700 automated sequencer (Applied Biosystems). Alignment of the DNA sequences was carried out using BioEdit (http://www.mbio.ncsu.edu/BioEdit/bioedit.html), following which the sequences were visually confirmed. All polymorphisms were rechecked from chromatograms while paying particular attention to low-frequency polymorphisms.

Heterozygosity was not observed in the sequences found by the inventors. A 1,784-bp gene in qLTG-3-1 that includes a 933-bp upstream region containing 5' and 3'UTR and a 296-bp downstream region, excluding TA repeats in the 50-bp region from base pairs 433 to 384, was sequenced in the cultivated rices and the wild varieties. The minimum range (haplotype) exhibiting a unique DNA sequence or an allele separated by a mutation step was constructed by the computer program TCS (Crandall et al., 2000) using the parsimony method in statistics.

All 1,784 nucleotides of the qLTG-3-1 gene were sequenced. Compared with the Italica Livorno sequence as a functional allele, 32 mutations—including insertions, deletions and substitutions—were detected (Table 6). Based on these mutations, ten different haplotypes were found among the 62 varieties in the rice core collection (Table 7; DNA sequences, FIGS. 26 to 34; amino acid sequences, FIGS. 35 to 37).

TABLE 6

Summary of DNA variation in qLTG-3-1 genomic DNA of rice core collection

| Region | 5' | | Exon | 3' |
|---|---|---|---|---|
| Position | 9 8 8 6 6 6 6 5 5 5 5 4 4 4 4 4 4 4 4 4 2 1 - - - + 1 1 1 6 6<br>0 4 1 7 4 3 2 9 7 6 1 9 9 9 8 8 6 5 5 4 3 1 3 9 6 4 5 2 8 9 0 2<br>5 5 3 4 0 7 0 8 9 2 5 3 2 2 1 0 4 9 5 4 3 7 0 7 9 1 0 7 1 0 4 7 | | | |
| Category | N N N D N N N N N N D I D $_{N/D}$ I N N N N D N I N N N R D D I D D | | | |

| Haplogroup | Haplotype | No. of strain | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| I | 1 | 23 | C G C C T C G C T A G - - - T - C G G C - C - C C T T - - - - - |
| I | 2 | 4 | C G C C T C G C T A G - - - 1 - C G G C - C - C C T T - - - - - |
| I | 3 | 1 | T G C C T C G C T A G - - - T - C G G C - C - C C T T - - - - - |
| I | 4 | 1 | C G C C T C G C T A G - - - T 1 C G G C - C - C C T T - - - - - |
| I | 5 | 3 | C G C C T C G C T A G - - - T - C G G C - C - C C T A - - - - - |
| II | 6 | 1 | C A T G 1 C G C A A G 1 - 1 T - C A A C - T $_{12}$ G G A T$_{18}$ 9 9 $_{11}$ - |
| II | 7 | 23 | C A T G 1 C G C A A G 1 - 1 C - C A A C - T $_{12}$ G G A T$_{18}$ 9 9 $_{11}$ - |
| II | 8 | 1 | C A T G 1 C G C A A G 1 - 1 C - T A A C - T $_{12}$ G G A T$_{18}$ 9 9 $_{11}$ - |
| r | 9 | 4 | C G C C T A A T T T A 1 - - C - C G G T - C - G G A T$_{18}$ - 36 11 10 |
| r | 10 | 1 | C G C C T A A T T T A - 1 - C - C G G C 6 C $_{12}$ C C T T$_{18}$ 9 9 $_{11}$ - |

Numbers indicated the position in the sequence relative to the first nucleotide of the start codon based on the Italica Livorno sequence. 50-bp region from -433 to -384 containing AT repeat is not sequenced.
Replacement from Leu to His occurred in haplotype 5. The R, S, N, M, I and D categories indicate replacement, synonymous, noncoding site, microsatellite, insertion and deletion, respectively.
r means recombination type in intra gene.
Number is the base number in insertion or deletion compared with haplotype 1.

TABLE 7

Classification of haplotype among rice core collection

| Code No. | Variety | Type | Origin | Group[1] | Haplogroup | Haplotype |
|---|---|---|---|---|---|---|
| WRC1 | NIPPONBARE | breeding | Japan | A | I | 5 |
| WRC2 | KASALATH | landrace | India | B | I | 1 |
| WRC3 | BEI KHE | landrace | Cambodia | C | II | 7 |
| WRC4 | JENA 035 | landrace | Nepal | B | I | 1 |
| WRC5 | NABA | landrace | India | C | II | 7 |
| WRC6 | PULUIK ARANG | landrace | Indonesia | C | II | 7 |
| WRC7 | DAVAO 1 | landrace | Philippines | C | II | 7 |
| WRC9 | RYOU SUISAN KOUMAI | landrace | China | C | II | 7 |
| WRC10 | SHUUSOUSHU | landrace | China | C | r | 9 |
| WRC11 | JINGUOYIN | landrace | China | C | II | 7 |
| WRC13 | ASU | landrace | Bhutan | C | I | 1 |
| WRC14 | IR 58 | breeding | Philippines | C | I | 2 |
| WRC15 | CO 13 | unknown | India | C | I | 2 |
| WRC16 | VARY FUTSI | landrace | Madagascar | C | II | 7 |
| WRC17 | KEIBOBA | landrace | China | C | r | 9 |
| WRC18 | QINGYU(SEIYU) | landrace | Taiwan | C | I | 9 |

TABLE 7-continued

Classification of haplotype among rice core collection

| Code No. | Variety | Type | Origin | Group[1] | Haplogroup | Haplotype |
|---|---|---|---|---|---|---|
| WRC19 | DENG PAO ZHAI | breeding | China | C | r | 9 |
| WRC20 | TADUKAN | landrace | Philippines | C | II | 7 |
| WRC21 | SHWE NANG GYI | landrace | Myanmar | C | I | 1 |
| WRC22 | CALOTOC | landrace | Philippines | B | II | 7 |
| WRC24 | PINULUPOT 1 | landrace | Philippines | C | II | 7 |
| WRC25 | MUHA | unknown | India | B | I | 4 |
| WRC26 | JHONA 2 | unknown | India | B | I | 2 |
| WRC27 | NEPAL 8 | landrace | Nepal | B | I | 1 |
| WRC28 | JARJAN | landrace | Bhutan | B | I | 1 |
| WRC29 | KALO DHAN | landrace | Nepal | B | I | 1 |
| WRC30 | ANJANA DHAN | landrace | Nepal | B | I | 1 |
| WRC31 | SHONI | landrace | Bangladesh | B | II | 7 |
| WRC32 | TUPA 121-3 | landrace | Bangladesh | B | I | 1 |
| WRC33 | SURJAMUKHI | breeding | India | B | I | 1 |
| WRC34 | ARC 7291 | landrace | India | B | I | 1 |
| WRC35 | ARC 5955 | landrace | India | B | II | 7 |
| WRC36 | RATUL | landrace | India | B | II | 7 |
| WRC37 | ARC 7047 | landrace | India | B | r | 10 |
| WRC38 | ARC 11094 | landrace | India | B | II | 7 |
| WRC39 | BADARI DHAN | landrace | Nepal | B | II | 7 |
| WRC40 | NEPAL 555 | unknown | India | B | II | 7 |
| WRC41 | KALUHEENATI | landrace | Sri Lanka | B | I | 2 |
| WRC42 | LOCAL BASMATI | landrace | India | B | II | 7 |
| WRC43 | DIANYU 1 | breeding | China | A | I | 5 |
| WRC44 | BASILANON | landrace | Philippines | B | I | 1 |
| WRC45 | MA SHO | landrace | Myanmar | A | I | 1 |
| WRC46 | KHAO NOK | landrace | Laos | A | I | 1 |
| WRC47 | JAGUARY | unknown | Brazil | A | I | 1 |
| WRC48 | KHAU MAC KHO | landrace | Vietnam | A | I | 1 |
| WRC49 | PADI PERAK | landrace | Indonesia | A | I | 1 |
| WRC50 | REXMONT | breeding | America | A | I | 1 |
| WRC51 | URASAN 1 | landrace | Japan | A | I | 1 |
| WRC52 | KHAU TAN CHIEM | landrace | Vietnam | A | I | 3 |
| WRC53 | TIMA | landrace | Bhutan | A | I | 1 |
| WRC55 | TUPA 729 | landrace | Bangladesh | A | I | 1 |
| WRC57 | MILYANG 23 | breeding | Korea | — | I | 5 |
| WRC58 | NEANG MENH | landrace | Cambodia | C | II | 8 |
| WRC59 | NEANG PHTONG | landrace | Cambodia | C | II | 7 |
| WRC61 | RADIN GOI SESAT | landrace | Malaysia | C | II | 7 |
| WRC62 | KEMASIN | landrace | Malaysia | C | II | 6 |
| WRC63 | BLEIYO | landrace | Thailand | C | II | 7 |
| WRC64 | PADI KUNING | landrace | Indonesia | C | II | 7 |
| WRC65 | RAMBHONG | landrace | Indonesia | C | II | 7 |
| WRC66 | BINGALA | landrace | Myanmar | C | II | 7 |
| WRC67 | PHULBA | landrace | India | A | I | 1 |
| WRC68 | KHAO NAM JEN | landrace | Laos | A | I | 1 |

[1])Kojima et al. (2005)

Two deletions, one insertion and one non-synonymous substitution arose in the gene coding region. All the deletions and insertions in the signal region arose as 3n by in-frame mutations. One non-synonymous substitution was detected in Nipponbare alone. Haplotypes 9 and 10 appear to have been obtained from intragenic recombinations between Haplogroups I and II.

Figure 38:
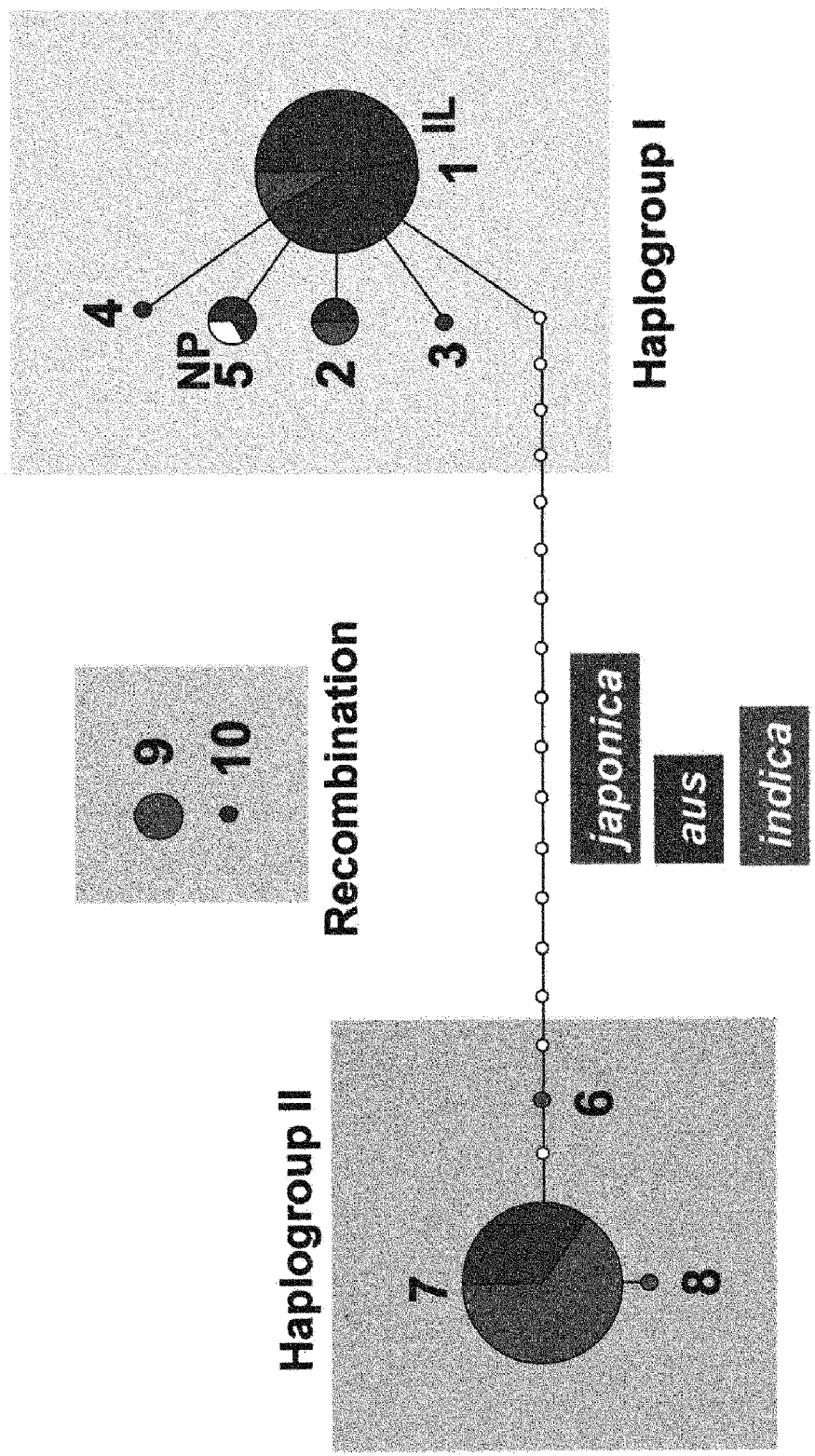
FIG. 38 shows the network of haplotypes for qLTG-3-1. The sizes of the circles are proportional to the number of lines within a given haplotype. The open circles between the closed circles represent unidentified haplotypes. The lines between haplotypes represent steps in the mutations between the respective haplotypes. The haplotype composition is indicated as the percentages of the number of lines. The blue (*japonica*), red (*aus*) and orange (*indica*) colors respectively indicate Groups A, B and C of the rice core collection.

A haplotype network was constructed from the gene mutations in the entire qLTG-3-1 gene. Because two haplotypes arose from intragenic recombinations, these were not included in the network. The network was composed of the two Haplogroups I and II (FIG. 38). This network was strongly supported by the gene sequence phylogenetic tree results.

These haplogroups were mutually segregated in 18 mutation steps. Haplogroup I containing five haplotypes was composed of 31 varieties, most of which were from Groups A and B of the core collection of rice. Haplogroup II containing three haplotypes was composed of 25 varieties, most of which were from Groups B and C.

The qLTG-3-1 sequences of relative rices in the AA genome were compared with the qLTG-3-1 functional allele (Haplotype I) of Italica Livorno. Numerous nucleotide changes, including insertions, deletions and substitutions, were detected. However, these were not detected in cultivated rices. Most of these nucleotide changes arose in *O. longistaminata* (W1413 and W1508), which clearly differed from the other lines.

Thirteen synonymous substitutions, 6 deletions and 11 insertions were detected in the gene coding region. All the deletions and insertions arose in-frame within the GRP region (FIGS. 26 to 34). Twenty-six insertions and deletions were detected in the entire qLTG-3-1 gene, excluding transposons and gene coding regions. Ten of these nucleotide changes were 3n, and the remaining were not 3n. In addition to the conservation of the qLTG-3-1 gene in cultivated rices, these wild rice results suggest that the qLTG-3-1 protein sequence is completely conserved owing to the importance of its functions in rice.

INDUSTRIAL APPLICABILITY

As described above, the present invention relates to a gene for low temperature germinability in rice, and a method for its use. Through this invention, there can be provided both a gene for a low temperature germinability isolated from the rice line Italica Livorno, and the base sequence of the gene. The present invention also makes it possible to provide a technique for utilizing the foregoing gene that employs the functions of the above gene alone for the low temperature germinability, e.g., the germinability-improving properties under low temperature, salt and osmotic pressure stresses; to provide a transgenic plant in which the above gene has been transformed to improve the low temperature germinability; and to differentiate between the levels of low temperature germinability in cultivated varieties by identifying gene mutations based on the sequence of the gene for the low temperature germinability. In the past, from QTL analysis, the high level of low temperature germinability recognized in Italica Livorno was thought to be a quantitative trait in which a plurality of genes participated. The present invention is useful in that it provides an isolated gene alone for the low temperature germinability as a substance, as well as the base sequence thereof, and also provides a technique for the use of the gene.

The invention claimed is:

1. An isolated nucleic acid which encodes a protein comprising the amino acid sequence set forth in SEQ ID NO: 20.

2. A method for producing a plant having low temperature germinability under an environment that suppresses germination of the plant, the method comprising,
   i) transforming a plant with a nucleic acid which encodes a protein comprising the amino acid sequence set forth in SEQ ID NO: 20; and
   ii) selecting a plant having improved low temperature germinability relative to a plant not transformed with a nucleic acid encoding the amino acid sequence set forth in SEQ ID NO: 20.

3. The method for producing a plant according to claim 2, wherein the environment for suppressing germination of the plant is low temperature, high concentration of salt, or high osmotic pressure.

4. The method according to claim 2, wherein the plant is rice.

5. The method according to claim 3, wherein the plant is rice.

6. A plant having low temperature germinability under an environment that suppresses germination of a plant,
   wherein the plant is produced by introducing a nucleic acid which encodes a protein comprising the amino acid sequence set forth in SEQ ID NO: 20 into a plant.

7. The plant according to claim 6, wherein the environment for suppressing germination of the plant is low temperature, high concentration of salts, or high osmotic pressure.

8. The plant according to claim 6, wherein the plant is rice.

9. The plant according to claim 7, wherein the plant is rice.

10. A seed collected from the plant produced by claim 6 wherein the seed comprises the nucleic acid encoding the protein comprising the amino acid sequence set forth in SEQ ID NO: 20.

11. A seed collected from the plant produced by claim 7, wherein the seed comprises the nucleic acid encoding the protein comprising the amino acid sequence set forth in SEQ ID NO: 20.

* * * * *